United States Patent
O'Toole et al.

(10) Patent No.: US 7,491,513 B2
(45) Date of Patent: Feb. 17, 2009

(54) COMPOSITION AND METHOD FOR TREATING LUPUS NEPHRITIS

(75) Inventors: Margot O'Toole, Newton, MA (US); William Martin Mounts, Andover, MA (US); Negin Shojaee, San Jose, CA (US)

(73) Assignee: Wyeth, Madison, NJ (US)

( * ) Notice: Subject to any disclaimer, the term of this patent is extended or adjusted under 35 U.S.C. 154(b) by 33 days.

(21) Appl. No.: 11/355,297

(22) Filed: Feb. 15, 2006

(65) Prior Publication Data

US 2006/0228356 A1   Oct. 12, 2006

Related U.S. Application Data

(62) Division of application No. 10/719,385, filed on Nov. 21, 2003, now Pat. No. 7,060,797.

(60) Provisional application No. 60/428,094, filed on Nov. 21, 2002.

(51) Int. Cl.
C12P 21/02    (2006.01)
C07H 21/04    (2006.01)

(52) U.S. Cl. .................. 435/69.1; 435/320.1; 435/328; 536/23.5; 530/350

(58) Field of Classification Search .................. None
See application file for complete search history.

(56) References Cited

U.S. PATENT DOCUMENTS

| | | | |
|---|---|---|---|
| 6,313,264 | B1 | 11/2001 | Caggiano et al. |
| 2002/0197679 | A1 | 12/2002 | Tang et al. |
| 2003/0049804 | A1 | 3/2003 | Pompejus et al. |
| 2004/0258678 | A1 | 12/2004 | Bodary et al. |

OTHER PUBLICATIONS

Balow, J.E. et al., " New Prospects for treatment of lupus nephritis," *Semin. Nephrol.*, 20(1):32-39 (2000).

Davis, J.C. et al., "Lupus nephritis," *Current Opin. Rheumatol.*, 8(5):415-423 (1996).

Mercada, L. and Deray, G., "Lupus nephritis, review of the current pharmacological treatments," *Expert Opin. Pharmacother.*, 5(11):2263-2277 (2004).

Rahman, Z.S.M. et al., A novel susceptibility locus on chromosome 2 in the (New Zealand black×New Zealand white) $F_1$ hybrid mouse model of systematic lupus erythematosus, *J. Immunol.*, 168(6):3042-3049 (2002).

Tsao, B.P., "Genetic susceptibility to lupus nephritis," *Lupus*, 7(9):585:590 (1998).

Ngo, Thomas J. et al., *The Protein Folding Problem and Tertiary Structure Prediction*, 1994, 492-494.

Metzler et al., *Nature Structural Biol.*, 1997, 4:527-531.

Attwood, *Science*, 2000, 290:471-473.

Skolnick et al., *Trends in Biotech.*, 2000, 18(1):34-39.

Whisstock et al., *Quarterly reviews of Biophysics*, 2003, 36:307-340.

Drake et al., "Genetic analysis of the NZB contribution to lupus-like autoimmune disease in (NZB×NZW) F1 mice," *Pro Natl. Acad. Sci. USA*, 91:4062-66, 1994.

Guglielmotti et al., "Bindarit prolongs survival and reduces renal damage of NSB/W lupus mice," *Clin. Exp. Rheumatol.*, 16:149, 1998.

Finck et al., "Interleukin 6 promotes murine lupus in NZB/NZW $F_1$ Mice," *The J. Clin. Invest.*, 94:585-591, 1994.

Yang et al., "Dietary conjugated linoleic acid protects against end stage disease of systemic lupus erythematosus in the NZB/W F1 mouse," *Immunopharmacol. Immunotoxicol.*, 22:433-49, 2000.

*Primary Examiner*—Eileen B. O'Hara
*Assistant Examiner*—Yunsoo Kim
(74) *Attorney, Agent, or Firm*—Maria Restrepo-Hartwig

(57) ABSTRACT

The present invention provides novel isolated BFLP0169 polynucleotides and polypeptides encoded by the BFLP0169 polynucleotides. Also provided are the antibodies that immunospecifically bind to a BFLP0169 polypeptide or any derivative (including fusion derivative), variant, mutant or fragment of the BFLP0169 polypeptide, polynucleotide or antibody. The invention additionally provides methods in which the BFLP0169 polypeptide, polynucleotide and antibody are utilized in the detection and treatment of a broad range of pathological states, as well as to other uses.

22 Claims, 1 Drawing Sheet

COMPOSITION AND METHOD FOR TREATING LUPUS NEPHRITIS

RELATED APPLICATIONS

This application is a divisional application of U.S. patent application Ser. No. 10/719,385, filed Nov. 21, 2003 now U.S. Pat. No. 7,060,797, which claims priority to U.S. provisional patent application 60/428,094, filed Nov. 21, 2002. The entire contents of these applications are incorporated herein by reference in their entireties.

FIELD OF THE INVENTION

The invention relates generally to nucleic acids and polypeptides and more specifically to nucleic acids and polypeptides encoding polypeptides useful for detecting and treating lupus nephritis, as well as for identifying therapeutic agents for treating the same.

BACKGROUND OF THE INVENTION

Lupus nephritis is an example of a "classical" auto-immune disease in which the patient's immune system attacks his/her own organs. It has been estimated that 45-75% of lupus patients eventually suffer from some form or other of kidney damage. Lupus varies greatly in severity from mild cases requiring minimal intervention to those in which significant damage occurs to vital organs such as lungs, kidneys, heart and brain, and which ultimately can be fatal. Lupus is predominantly a female disease, with an approximate female to male ratio being 9:1. In North America, it is estimated to affect 1 in 500 females mainly between the age of 20 to 40 years.

There is no known cure for lupus. Treatment is typically directed at controlling the symptoms with the hope of putting the disease into remission. Recently, the antibiotic rapamycin has been demonstrated to be an effective therapy in treating lupus nephritis in a murine model of the disease.

SUMMARY OF THE INVENTION

The invention is based, in part, upon the discovery of a gene, named BFLP0169, whose expression is increased in kidney tissue in mice with lupus nephritis; however, the expression level of the gene does not decrease markedly in response to treatment with rapamycin. This expression profile indicates that the product of the BFLP0169 gene interacts with rapamycin when this antibiotic is administered to ameliorate the symptoms of lupus nephritis. In the absence of rapamycin, the gene product is free to bring about the diseased state, and its effects can include the activation of genes required to bring about the diseased state. In the presence of rapamycin, the BFLP0169 gene product is inactive and the diseased state diminishes. Accordingly, the BFLP0169 protein is useful as a target for identifying agents that, like rapamycin, are useful in treating symptoms of lupus nephritis.

In one aspect, the invention provides an isolated nucleic acid molecule that includes the sequence of a nucleotide sequence encoding a BFLP0169 gene product. In a preferred embodiment, the nucleotide sequence includes the sequence of SEQ ID NO:1, or a fragment, homolog, analog or derivative thereof. The nucleic acid can include, e.g., a nucleic acid sequence encoding a polypeptide at least 70%, e.g., 80%, 85%, 90%, 95%, 98%, or even 99% or more identical to a polypeptide that includes the amino acid sequences of SEQ ID NO:2. The nucleic acid can be, e.g., a genomic DNA fragment, or a cDNA molecule.

Also included in the invention is a vector containing one or more of the nucleic acids described herein, and a cell containing the vectors or nucleic acids described herein.

The invention is also directed to host cells transformed with a vector comprising any of the nucleic acid molecules described above.

In another aspect, the invention includes a pharmaceutical composition that includes a BFLP0169 nucleic acid and a pharmaceutically acceptable carrier or diluent.

In a further aspect, the invention includes a substantially purified BFLP0169 polypeptide, e.g., any of the BFLP0169 polypeptides encoded by a BFLP0169 nucleic acid, and fragments, homologs, analogs, and derivatives thereof. The invention also includes a pharmaceutical composition that includes a BFLP0169 polypeptide and a pharmaceutically acceptable carrier or diluent.

In a still further aspect, the invention provides an antibody that binds specifically to a BFLP0169 polypeptide. The antibody can be, e.g., a monoclonal or polyclonal antibody, and fragments, homologs, analogs, and derivatives thereof. The invention also includes a pharmaceutical composition including BFLP0169 antibody and a pharmaceutically acceptable carrier or diluent. The invention is also directed to isolated antibodies that bind to an epitope on a polypeptide encoded by any of the nucleic acid molecules described above.

The invention also includes kits comprising in one or more containers one or more of a compound that is a BFLP0169 nucleic acid, a BFLP0169 polypeptide and/or an antibody to a BFLP0169 polypeptide. The kit is preferably provided with instructions for use. If desired, the compounds in the kits are provided along with a pharmaceutically acceptable carrier.

The invention further provides a method for producing a BFLP0169 polypeptide by providing a cell containing a BFLP0169 nucleic acid, e.g., a vector that includes a BFLP0169 nucleic acid, and culturing the cell under conditions sufficient to express the BFLP0169 polypeptide encoded by the nucleic acid. The expressed BFLP0169 polypeptide is then recovered from the cell. Preferably, the cell produces little or no endogenous BFLP0169 polypeptide. The cell can be, e.g., a prokaryotic cell or eukaryotic cell.

The invention is also directed to methods of identifying a BFLP0169 polypeptide or nucleic acid in a sample by contacting the sample with a compound that specifically binds to the polypeptide or nucleic acid, and detecting complex formation, if present.

The invention further provides methods of identifying a compound that modulates the activity of a BFLP0169 polypeptide by contacting a BFLP0169 polypeptide with a compound and determining whether the BFLP0169 polypeptide activity is modified.

The invention is also directed to compounds that modulate BFLP0169 polypeptide activity identified by contacting a BFLP0169 polypeptide with the compound and determining whether the compound modifies activity of the BFLP0169 polypeptide, binds to the BFLP0169 polypeptide, or binds to a nucleic acid molecule encoding a BFLP0169 polypeptide.

In another aspect, the invention provides a method of determining the presence of or predisposition of a BFLP0169-associated disorder in a subject. The method includes providing a sample from the subject and measuring the amount of BFLP0169 polypeptide in the subject sample. The amount of BFLP0169 polypeptide in the subject sample is then compared to the amount of BFLP0169 polypeptide in a control sample. An alteration in the amount of BFLP0169 polypeptide in the subject protein sample relative to the amount of BFLP0169 polypeptide in the control protein sample indicates the subject has a tissue proliferation-associated condition. A control sample is preferably taken from a matched individual, i.e., an individual of similar age, sex, or other general condition but who is not suspected of having a tissue proliferation-associated condition. Alternatively, the control sample may be taken from the subject at a time when the subject is not suspected of having a tissue proliferation-associated disorder. In some embodiments, the BFLP0169 is detected using a BFLP0169 antibody.

In a further aspect, the invention provides a method of determining the presence of or predisposition of a BFLP0169-associated disorder in a subject. The method includes providing a nucleic acid sample, e.g., RNA or DNA, or both, from the subject and measuring the amount of the BFLP0169 nucleic acid in the subject nucleic acid sample. The amount of BFLP0169 nucleic acid sample in the subject nucleic acid sample is then compared to the amount of a BFLP0169 nucleic acid in a control sample. An alteration in the amount of BFLP0169 nucleic acid in the sample relative to the amount of BFLP0169 in the control sample indicates the subject has a tissue proliferation-associated disorder.

In a still further aspect, the invention provides a method of treating or preventing or delaying a BFLP0169-associated disorder. The method includes administering to a subject in which such treatment or prevention or delay is desired a BFLP0169 nucleic acid, a BFLP0169 polypeptide, or a BFLP0169 antibody in an amount sufficient to treat, prevent, or delay a tissue proliferation-associated disorder in the subject. Examples of such disorders include rheumatoid arthritis and multiple sclerosis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
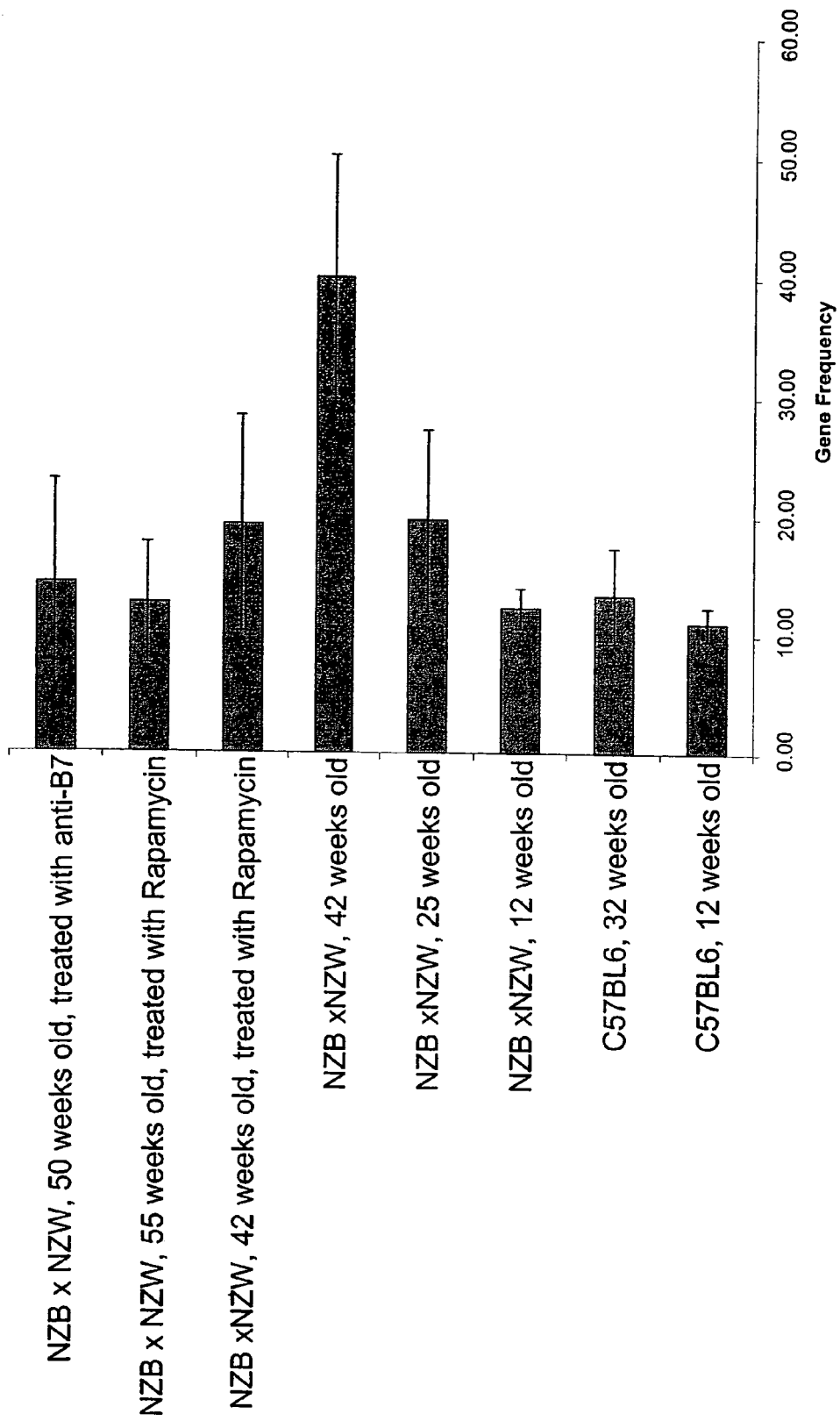
FIG. 1 is a histogram showing relative levels of gene expression in the mouse ortholog of the human BFLP0169 gene in NZBxNZWF1 kidneys before, during, and after rapamycin treatment, as well as in various control mouse strains and conditions.

The BFLP0169 nucleic acid sequences disclosed herein were identified based on changes in expression of the gene in kidneys of a lupus nephritis model mouse as compared to expression of the gene in kidneys from non non-diseased mice. More particularly, the gene is expressed at relatively low levels in young mice and mice that do not show symptoms of lupus nephritis. Gene expression is elevated in mice with lupus nephritis, and is lower in mice that have been successfully treated with rapamycin or anti-B7 antibodies. The observation that expression levels return to normal when kidney function is normal indicates that elevated levels are related to, and diagnostic of, disease progression. Blocking the function of these genes may inhibit or retard disease progression. Expression levels can also to used to assess and compare effectiveness of various therapeutic interventions.

Accordingly, the BFLP0169 nucleic acid sequences are useful for detecting the presence of lupus nephritis in a subject. Elevated levels of BFLP0169 transcripts orpolypeptides relative to levels in control samples indicate the presence of lupus nephritis in the subject. BFLP0169 nucleic acid sequences can also be used to monitor the effectiveness of treatments for lupus nephritis: a decrease in expression of BFLP0169 genes relative to levels in diseased treatments demonstrates that the treatment is effective.

The BFLP0169 sequences can additionally be used to identify therapeutic agents for treating or preventing lupus nephritis in a subject. For example, a BFLP0169 polypeptide can be contacted with a test agent. Binding of the BFLP0169 polypeptide to the test agent reveals that the test agent modulates BFLP0169 activity. The BFLP0169-binding agent can be further tested to determine if it acts to promote or inhibit lupus symptoms in a test organism (e.g., a NZBxNZW mouse). Inhibition of lupus symptoms reveals that the agent is useful for treating or preventing lupus nephritis, or symptoms associated with lupus nephritis. Additional utilities are disclosed herein.

A 5987 nucleotide sequence that includes a human BFLP0169 nucleic acid is shown in Table 1 (SEQ ID NO:1). The human sequence was identified as the human ortholog of a murine gene whose expression is increased in a NZBxNZW mouse with lupus nephritis-like symptoms.

Nucleotides 1-5259 of the sequence shown in Table 1 encode a polypeptide of 1753 amino acids, whose sequence is shown in Table 2 (SEQ ID NO:2).

TABLE 1

ATGATCAGAAAGAGCAAAATTACCTCTGTTCTCTCATTTTGCAGGAGCAG

TAGAGAACTGTGGACTATTCTGCTTGGAAGGTCAGCTCTGAGAGAGCTGA

GTCAGATTGAGGCAGAACTGAATAAACATTGGCGGCGATTGTTAGAGGGG

CTTTCTTACTACAAACCTCCCAGTCCAAGTTCAGCTGAAAAAGTGAAAGC

TAATAAAGATGTAGTTCACCATTGAAGGAACTGGGTTTAAGAATCAGCAA

GTTTTTGGGTCTTGATGAAGAACAGAGTGTGCAGTTACTCCAGTGTTACC

TGCAAGAGGACTACAGGGGTACTCGGGACTCAGTAAAGACAGTACTGCAA

GATGAGAGGCAGAGCCAGGCCTTAATCCTGAAGATTGCAAGATTATTATT

ATGAAGAAGAACCTGTATTCTTCGTTGTGTCTTACACCTTCTCACTTACT

TCCAAGATGAAAGACACCCCTATAGGGTTGAATATGCAGACTGTGTTGAT

AAATTGGAGAAGGAACTAGTTTCAAAATACAGACAGCAGTTCGAAGAGCT

TTATAAAACTGAAGCACCAACTTGGGAGACACATGGAAATCTCATGACAG

AGCGCCAAGTGTCTCGCTGGTTTGTTCAGTGCCTTCGGGAACAGTCCATG

CTGCTAGAAATTATTTTCCTTTATTATGCATACTTTGAGATGGCACCCAG

TGACTTACTTGTATTACCAAGATGTTTAAAGAGCAAGGATTTGGTAGTAG

GCAGACCAATAGGCACCTGGTGGATGAGACTATGGATCCTTTTGTAGATC

GGATTGGCTACTTCAGTGCCCTCATCCTGGTGGAGGGCATGGATATCGAG

TCCTTGCATAAGTGTGCTTTGGATGACAGAAGAGAACTGCATCAGTTTGC

GCAGGATGGGCTTATTTGTCAGGATATGGACTGTTTAATGTTGACCTTTG

TABLE 1-continued

```
GGGACATTCCACATCATGCCCCAGTGCTTTTGGCCTGGGCTCTCCTCCGT
CACACTCTGAACCCAGAAGAGACAAGCAGTGTGGTCCGGAAGATAGGTGG
CACAGCCATCCAGCTGAATGTGTTTCAGTACTTGACCCGATTGCTCCAGT
CCCTTGCCAGTGGGGGAAATGATTGCACCACCAGCACTGCATGCATGTGT
GTCTATGGACTGCTCTCTTTCGTTCTGACCTCGTTGGAGCTGCACACCCT
GGGCAATCAGCAGGATATAATTGATACAGCATGTGAAGTATTGGCCGACC
CTTCTCTTCCGGAACTGTTCTGGGGAACAGAGCCAACTTCTGGCCTTGGG
ATCATTCTGGACAGTGTGTGTGGAATGTTTCCCCACCTTCTCTCCCCACT
CCTGCAACTGCTCCGAGCCCTGGTATCAGGGAAGTCCACAGCCAAAAAGG
TGTATAGCTTCTTGGATAAGATGTCTTTCTACAATGAACTTTATAAACAC
AAGCCTCATGATGTGATCTCCCATGAAGATGGAACTCTTTGGCGGAGACA
AACACCCAAACTCCTTTATCCCCTTGGGGGTCAAACCAACCTTCGCATAC
CTCAAGGCACTGTGGGCCAAGTAATGTTGGATGATAGGGCATACCTGGTA
CGCTGGGAATACTCCTATAGCAGCTGGACCCTCTTTACCTGCGAGATTGA
AATGTTGCTTCATGTTGTTTCAACTGCAGATGTGATTCAGCACTGCCAGC
GAGTCAAACCCATCATTGATCTCGTCCATAAGGTCATCAGTACAGACCTG
TCGATAGCAGACTGTCTCCTGCCCATCACATCTCGCATCTACATGCTGCT
GCAGCGGTTAACGACAGTGATCTCCCCACCTGTGGATGTCATTGCTTCTT
GTGTCAACTGCTTAACTGTTTTGGCTGCCCGCAATCCAGCAAAGGTCTGG
ACTGATCTTCGTCACACAGGTTTTTTACCATTTGTGGCCCATCCTGTCTC
CAGCCTGAGTCAGATGATTAGTGCGGAAGGGATGAATGCTGGAGGGTACG
GAAACCTCTTGATGAACAGTGAACAGCCTCAGGGCGAGTATGGGGTTACT
ATTGCCTTTCTGCGCTTGATCACCACCCTTGTCAAGGGGCAACTTGGTAG
TACCCAGAGCCAAGGACTTGTACCCTGTGTAATGTTTGTGCTGAAGGAGA
TGCTTCCCAGCTACCATAAGTGGCGCTACAACTCTCATGGAGTGAGGGAA
CAGATTGGTTGCCTGATCTTGGAGCTGATTCATGCGATACTGAACCTGTG
CCACGAGACAGACCTGCACAGCAGTCATACTCCCAGCCTGCAGTTTCTCT
GCATCTGCAGCCTGGCATACACAGAAGCAGGACAGACAGTTATCAATATC
ATGGGCATTGGCGTGGACACCATTGACATGGTGATGGCTGCTCAGCCTCG
AAGTGATGGGCAGAGGGCCAGGGGCAGGGCCAGCTGCTGATCAAGACAG
TGAAACTGGCATTCTCCGTCACCAACAATGTTATTCGGCTGAAACCTCCT
TCTAATGTGGTGTCCCCCCTGGAACAGGCTCTCTCACAACATGGTGCTCA
TGGAAACAACCTCATTGCTGTTCTAGCCAAATACATCTACCACAAACATG
ACCCTGCTTTGCCACGTCTTGCCATTCAGCTGCTGAAACGTCTGGCCACG
GTGGCCCCAATGTCAGTGTATGCTTGTCTGGGCAATGATGCGGCTGCCAT
TCGTGATGCCTTCCTGACCCGATTGCAGAGCAAAATTGAGGACATGCGCA
TCAAAGTCATGATTCTAGAGTTCCTCACTGTTGCAGTAGAGACCCAGCCA
GGCCTCATCGAACTGTTTCTGAACCTGGAAGTTAAGGATGGCAGTGATGG
CTCAAAGGAATTCAGCCTTGGGATGTGGAGCTGTCTCCATGCAGTGCTGG
AGCTGATTGATTCCCAACAGCAAGATCGATACTGGTGCCCACCCCTGCTG
CATCGTGCCGCCATTGCCTTTTTGCATGCTCTGTGGCAGGATCGGAGGGA
CAGTGCCATGCTGGTCCTCCGAACCCAAACCCAAGTTTTGGGAAAATTTAA
CCAGTCCGCTGTTTGGAACCCTTTCTCCTCCCTCTGACAAATCAGAGCCC
AGCATCCTGGAAACCTGTGCCCTAATCATGAAGATAATTTGCTTGGAGAT
ATACTATGTAGTAAAGGGTTCATTAGACCAGTCATTAAAGGATACACTGA
AGAAATTTTCCATCGAGAAACGCTTTGCCTACTGGTCAGGGTATGTCAAG
TCATTGGCAGTTCACGTGGCCGAAACAGAAGGCAGCAGCTGCACCTCCTT
GTTAGAGTACCAGATGCTGGTGTCCGCCTGGAGGATGCTTCTCATCATTG
CCACCACTCATGCAGATATAATGCACCTGACTGACTCTGTGGTGCGTCGC
CAGCTCTTTCTTGACGTGCTTGATGGAACCAAAGCATTACTCCTAGTTCC
AGCCTCAGTGAACTGCCTTCGCCTTGGCTCCATGAAGTGCACTCTGCTGC
TTATCCTCCTCCGGCAGTGGAAGAGAGAGTTAGGTTCTGTGGATGAAATC
CTTGGACCCTTGACGGAGATCCTGGAGGGAGTGCTGCAGGCCGACCAGCA
ACTCATGGAGAAGACCAAGGCCAAGGTGTTCTCAGCATTCATCACAGTGT
TGCAAATGAAGGAGATGAAGTAAGTGACATCCCCCAGTACTCCCAGCTGG
TGCTGAATGTCTGTGAGACCCTCCAAGAGGAAGTGATTGCACTCTTCGAC
CAGACCCGCCACAGTCTGGCATTAGGCAGTGCCACAGAGGACAAGGACAG
CATGGAGACTGACGACTGTTCTCGGTCCCGGCACAGGGACCAGCGTGATG
GGGTGTGTGTCCTGGGCCTGCACCTGGCCAAGGAGCTGTGTGAGGTAGAC
GAGGATGGTGACTCCTGGCTGCAGGTAACCCGCAGGCTCCCATCCTACC
CACCCTCCTCACCACTCTAGAGGTGAGCCTTCGCATGAAGCAGAACCTGC
ATTTCACTGAGGCCACATTGCATCTGCTCCTCACCCTGGCTCGCACTCAG
CAGGGAGCCACAGCAGTGGCTGGAGCTGGCATCACCCAGAGCATTTGTTT
GCCCCTTCTGAGTGTGTACCAGCTGAGCACCAACGGCACAGCACAGACAC
CTAGTGCCTCTCGGAAGTCCCTGGATGCCCCTCTTGGCCAGGAGTCTAC
CGCCTGTCCATGTCCCTGATGGAGCAGCTGCTCAAACTCTGCGCTACAAC
TTCCTGCCTGAGGCCCTGGACTTCGTGGGTGTCCACCAGGAGCGGACCTT
ACAGTGCCTCAACGCAGTGAGGACAGTGCAGAGTCTGGCCTGCCTGGAGG
AGGCGGACCACACCGTGGGTTTTATTCTGCAGCTCTCTAACTTCATGAAG
GAGTGGCACTTCCACCTGCCTCAGCTCATGCGTGATATCCAGGTCAACCT
GGGTTACTTGTGCCAGGCATGTACCTCTCTCCTGCACAGTCGAAAGATGC
TGCAGCATTACTTACAGAACAAAAATGGGGATGGCCTCCCCTCAGCTGTT
GCCCAGCGAGTCCAGAGGCCACCGTCTGCTGCTTCTGCTGCCCCCTCCTC
CTCAAAGCAGCCCGCTGCTGACACAGAGGCATCAGAGCAGCAGGCCTTGC
ACACAGTCCAGTATGGCCTTCTCAAGATCCTCAGCAAGACGCTGGCAGCC
CTGCGCCACTTCACCCCAGATGTCTGCCAGATTCTGCTGGATCAGTCCCT
GGACCTTGCTGAATACAACTTCCTGTTTGCCCTGAGCTTTACCACTCCCA
CCTTTGACTCCGAAGTGGCCCCCTCCTTCGGGACCCTTCTGGCCACAGTG
AATGTGGCCCTCAACATGCTTGGAGAGCTGGACAAGAAAAAGGAGCCCCT
CACCCAGGCAGTGGGGCTCAGCACACAGGCAGAAGGGACCAGGACGTTAA
```

TABLE 1-continued

```
AGTCCCTCCTGATGTTTACCATGGAAAACTGCTTCTACCTGCTCATCTCT
CAGGCGATGCGGTACCTTAGGGACCCGGCTGTGCACCCCGGGACAAACA
GCGGATGAAGCAGGAGCTCAGCTCTGAGTTGAGCACGCTGCTGTCCAGCC
TCTCGCGCTACTTCCGCCGGGGAGCCCCAGCTCCCCTGCCACTGGTGTC
CTCCCCTCGCCGCAGGGCAAGTCCACCTCTCTCTCCAAAGCCAGCCCTGA
GAGTCAGGAGCCTCTGATCCAGTTGGTGCAGGCGTTTGTCCGGCATATGC
AAAGATAGGGCAGTGCTGTTCTGCCCACCTACCCCTCTCCACCAGCCTAC
ACTGCACCCTGGCTGGCAGGGGTGCTGCTGGCTGCTAGGGCCTATACAAT
GGAGGGCACCTCCTGTCACCCCCCTCCCGGAGTAGCCACGACTCCAGCCA
CCACCCACTGACGTTATTTTTATACTAGATGAAGAGGTCAACAGCAGGCA
TGGGGAGCCGAGTCTTCTGTGCTCAGGTCCTCACGCTGCAGACGCCCCT
AGAGGAACTTTCCTTCCTTTCCAGCATTCCCCACAGCACTGCCGGCCAGG
GGAGAGGCGGCAGCCCAGCAGAGGGCTCTATGCACGGGTTTCAAACCTGT
TTTCCACACTCTGTCTTTGCAGTTTTGGTAATTCTGTGGTCTATTTATAC
AGATATTAAAATCTTGTTTATAGACAGCTGTGTGATGTTTAACTTCAAAG
CCCAGGGATGACAACGTGGCTCTCAGAACCTAGAAAACTCCCCTGGCCAG
GCGCCTGGGAGTGGGGCTGCAGCCTCGGGGGAAGGCAGGTACTGATGGAT
GGCTAGTTCACCAGCATCTCCTCATTCCTGTCCTTGGGCTGAGGGTTTGG
CTGGGTGGGCGCTGTCAGATATTCCCTTCCTTGGCCTGCGCTGGTCCTGT
CCTTGACCCTGCTTTCATTGGCCCAGTGGGCTGAGCTCATCCCTGGGTGA
GCCTTTCTTGAAGCTCTGTGCCTTCCTATTTAT (SEQ ID NO:1)
```

TABLE 2

```
MIRKSKITSVLSFCRSSRELWTILLGRSALRELSQIEAELNKHWRRLLEG
LSYYKPPSPSSAEKVKANKDVASPLKELGLRISKFLGLDEEQSVQLLQCY
LQEDYRGTRDSVKTVLQDERQSQALILKIADYYYEERTCILRCVLHLLTY
FQDERHPYRVEYADCVDKLEKELVSKYRQQFEELYKTEAPTWETHGNLMT
ERQVSRWFVQCLREQSMLLEIIFLYYAYFEMAPSDLLVLTKMFKEQGFGS
RQTNRHLVDETMDPFVDRIGYFSALILVEGMDIESLHKCALDDRRELHQF
AQDGLICQDMDCLMLTFGDIPHHAPVLLAWALLRHTLNPEETSSVVRKIG
GTAIQLNVFQYLTRLLQSLASGGNDCTTSTACMCVYGLLSFVLTSLELHT
LGNQQDIIDTACEVLADPSLPELFWGTEPTSGLGIILDSVCGMFPHLLSP
LLQLLRALVSGKSTAKKVYSFLDKMSFYNELYKHKPHDVISHEDGTLWRR
QTPKLLYPLGGQTNLRIPQGTVGQVMLDDRAYLVRWEYSYSSWTLFTCEI
EMLLHVVSTADVIQHCQRVKPIIDLVHKVISTDLSIADCLLPITSRIYML
LQRLTTVISPPVDVIASCVNCLTVLAARNPAKVWTDLRHTGFLPFVAHPV
SSLSQMISAEGMNAGGYGNLLMNSEQPQGEYGVTIAFLRLITTLVKGQLG
STQSQGLVPCVMFVLKEMLPSYHKWRYNSHGVREQIGCLILELIHAILNL
CHETDLHSSHTPSLQFLCICSLAYTEAGQTVINIMGIGVDTIDMVMAAQP
```

TABLE 2-continued

```
RSDGAEGQGQGQLLIKTVKLAFSVTNNVIRLKPPSNVVSPLEQALSQHGA
HGNNLIAVLAKYIYHKHDPALPRLAIQLLKRLATVAPMSVYACLGNDAAA
IRDAFLTRLQSKIEDMRIKVMILEFLTVAVETQPGLIELFLNLEVKDGSD
GSKEFSLGMWSCLHAVLELIDSQQQDRYWCPPLLHRAAIAFLHALWQDRR
DSAMLVLRTKPKFWENLTSPLFGTLSPPSETSEPSILETCALIMKIICLE
IYYVVKGSLDQSLKDTLKKFSIEKRFAYWSGYVKSLAVHVAETEGSSCTS
LLEYQMLVSAWRMLLIIATTHADIMHLTDSVVRRQLFLDVLDGTKALLLV
PASVNCLRLGSMKCTLLLILLRQWKRELGSVDEILGPLTEILEGVLQADQ
QLMEKTKAKVFSAFITVLQMKEMKVSDIPQYSQLVLNVCETLQEEVIALF
DQTRHSLALGSATEDKDSMETDDCSRSRHRDQRDGVCVLGLHLAKELCEV
DEDGDSWLQVTRRLPILPTLLTTLEVSLRMKQNLHFTEATLHLLLTLART
QQGATAVAGAGITQSICLPLLSVYQLSTNGTAQTPSASRKSLDAPSWPGV
YRLSMSLMEQLLKTLRYNFLPEALDFVGVHQERTLQCLNAVRTVQSLACL
EEADHTVGFILQLSNFMKEWHFHLPQLMRDIQVNLGYLCQACTSLLHSRK
MLQHYLQNKNGDGLPSAVAQRVQRPPSAASAAPSSSKQPAADTEASEQQA
LHTVQYGLLKILSKTLAALRHFTPDVCQILLDQSLDLAEYNFLFALSFTT
PTFDSEVAPSFGTLLATVNVALNMLGELDKKKEPLTQAVGLSTQAEGTRT
LKSLLMFTMENCFYLLISQAMRYLRDPAVHPRDKQRMKQELSSELSTLLS
SLSRYFRRGAPSSPATGVLPSPQGKSTSLSKASPESQEPLIQLVQAFVRH
MQR (SEQ ID NO:2)
```

BFLP0169-like nucleic acids and polypeptides of the invention (including those shown in Table 1) are referred to herein as "BFLP0169" nucleic acids and polypeptides.

A BFLP0169 nucleic acid, and the encoded polypeptide, according to the invention are useful in a variety of applications and contexts.

BFLP0169 shows homolgy to other proteins as shown in the BLAST results decribed in Table 3. KIAA0169, IMAGE: 3461492, and 3598686, and cDNA: FLJ21639 are all proteins encoded from partial reading frames (expressed sequence tags (ESTs)) found in genomic DNA. Because BFLP0169 has homology to these proteins, it is also encoded from either an entire open reading frame, or part of a larger open reading frame (EST).

TABLE 3

Blast Results for BFLP0169

| Gene Index/ Identifier | Protein/ Organism | Length (aa) | Identity (%) | Positives (%) | Expect |
|---|---|---|---|---|---|
| gi\|1136397\|dbj\| D79991.1\| | *Homo sapiens* mRNA for KIAA0169 protein, partial cds | 1745 | 1635/1739 (94%) | 1635/1739 (94%) | 0.0 |
| gi\|22046118\|ref\| XP_052725.6\| (XM_052725) | similar to KIAA0169 protein [*Homo sapiens*] | 1767 | 1635/1743 (93%) | 1635/1743 (93%) | 0.0 |
| gi\|23618434\|ref\| XP_130085.2\| (XM_130085) | similar to KIAA0169 protein [*Homo sapiens*] | 1111 | 949/1111 (85%) | 982/1111 (87%) | 0.0 |
| gi\|13529308\|gb\| AAH05407.1\|AAH05407 (BC005407) | Unknown (protein for IMAGE: 3461492) [*Homo sapiens*] | 853 | 740/801 (92%) | 740/801 (92%) | 0.0 |
| gi\|19343754\|gb\| AAH25526.1\| (BC025526) | Similar to KIAA0169 protein [*Mus musculus*] | 525 | 411/522 (78%) | 422/522 (80%) | 0.0 |

Table 4 shows a ClustalW alignment of BFLP0169 (SEQ ID NO:2) against the proteins described above in Table 3.

TABLE 4

ClustalW Analysis of SEQ ID NO: 2

1) SEQ ID NO: 2
2) gi|1136397|dbj|D79991.1| (SEQ ID NO: 21)
3) gi|22046118|ref|XP_052725.6| (XM_052725) (SEQ ID NO: 22)
4) gi|23618434|ref|XP_130085.2| (XM_130085) (SEQ ID NO: 23)
5) gi|13529308|gb|AAH05407.1|AAH05407 (BC005407) (SEQ ID NO: 24)
6) gi|19343754|gb|AAH25526.1| (BC025526) (SEQ ID NO: 25)

```
                            10         20         30         40         50         60
                   ....|....|....|....|....|....|....|....|....|....|....|....|
SEQ ID NO: 2       --------------------MIRKSKITSVLSFCRSSRELWTILLGRSALRELSQIEAELNKHWRRLLEG  50
gi|1136398|dbj|    ----------------------------AGGPCVRSSRELWTILLGRSALRELSQIEAELNKHWRRLLEG  42
gi|22046118|ref|   MASGGGVRASGRAKMAAAAGGPCVRSSRELWTILLGRSALRELSQIEAELNKHWRRLLEG  60
gi|23618434|ref|   ------------------------------------------------------------   1
gi|13529308|gb|    ------------------------------------------------------------   1
gi|19343754|gb|    ------------------------------------------------------------   1

70         80         90        100        110        120
                   ....|....|....|....|....|....|....|....|....|....|....|....|
SEQ ID NO: 2       LSYYKPPSPSSAEKVKANKDVASPLKELGLRISKFLGLDEEQSVQLLQCYLQEDYRGTRD 110
gi|1136398|dbj|    LSYYKPPSPSSAEKVKANKDVASPLKELGLRISKFLGLDEEQSVQLLQCYLQEDYRGTRD 102
gi|22046118|ref|   LSYYKPPSPSSAEKVKANKDVASPLKELGLRISKFLGLDEEQSVQLLQCYLQEDYRGTRD 120
gi|23628434|ref|   ------------------------------------------------------------   1
gi|13529308|gb|    ------------------------------------------------------------   1
gi|19343754|gb|    ------------------------------------------------------------   1

130        140        150        160        170        180
                   ....|....|....|....|....|....|....|....|....|....|....|....|
SEQ ID NO: 2       SVKTVLQDERQSQALILKIADYYYEERTCILRCVLHLLTYFQDERHPYRVEYADCVDKLE 170
gi|1136398|dbj|    SVKTVLQDERQSQALILKIADYYYEERTCILRCVLHLLTYFQDERHPYRVEYADCVDKLE 162
gi|22046118|ref|   SVKTVLQDERQSQALILKIADYYYEERTCILRCVLHLLTYFQDERHPYRVEYADCVDKLE 180
gi|23618434|ref|   ------------------------------------------------------------   1
gi|13529308|gb|    ------------------------------------------------------------   1
gi|19343754|gb|    ------------------------------------------------------------   1

190        200        210        220        230        240
                   ....|....|....|....|....|....|....|....|....|....|....|....|
SEQ ID NO: 2       KELVSKYRQQFEELYKTEAPTWETHGNLMTERQVSRWFVQCLREQSMLLEIIFLYYAYFE 230
gi|1136398|dbj|    KELVSKYRQQFEELYKTEAPTWETHGNLMTERQVSRWFVQCLREQSMLLEIIFLYYAYFE 222
gi|22046118|ref|   KELVSKYRQQFEELYKTEAPTWETHGNLMTERQVSRWFVQCLREQSMLLEIIFLYYAYFE 240
gi|23618434|ref|   ------------------------------------------------------------   1
gi|13529308|gb|    ------------------------------------------------------------   1
gi|19343754|gb|    ------------------------------------------------------------   1
```

TABLE 4-continued

ClustalW Analysis of SEQ ID NO: 2

```
                    250       260       270       280       290       300
               ....|....|....|....|....|....|....|....|....|....|....|....|
SEQ ID NO: 2       MAPSDLLVLTKMFKEQGFGSRQTNRHLVDETMDPFVDRIGYFSALILVEGMDIESLHKCA 290
gi|1136398|dbj|    MAPSDLLVLTKMFKEQGFGSRQTNRHLVDETMDPFVDRIGYFSALILVEGMDIESLHKCA 282
gi|22046118|ref    MAPSDLLVLTKMFKEQGFGSRQTNRHLVDETMDPFVDRIGYFSALILVEGMDIESLHKCA 300
gi|23618434|ref    ------------------------------------------------------------ 1
gi|13529308|gb|    ------------------------------------------------------------ 1
gi|19343754|gb|    ------------------------------------------------------------ 1

310       320       330       340       350       360
                    ....|....|....|....|....|....|....|....|....|....|....|....|
SEQ ID NO: 2       LDDRRELHQFAQDGLICQDMDCLMLTFGDIPHHAPVLLAWALLRHTLNPEETSSVVRKIG 350
gi|1136398|dbj|    LDDRRELHQFAQDGLICQDMDCLMLTFGDIPHHAPVLLAWALLRHTLNPEETSSVVRKIG 342
gi|22046118|ref    LDDRRELHQFAQDGLICQDMDCLMLTFGDIPHHAPVLLAWALLRHTLNPEETSSVVRKIG 360
gi|23618434|ref    ------------------------------------------------------------ 1
gi|13529308|gb|    ------------------------------------------------------------ 1
gi|19343754|gb|    ------------------------------------------------------------ 1

370       380       390       400       410       420
                    ....|....|....|....|....|....|....|....|....|....|....|....|
SEQ ID NO: 2       GTAIQLNVFQYLTRLLQSLASGGNDCTTSTACMCVYGLLSFVLTSLELHTLGNQQDIIDT 410
gi|1136398|dbj|    GTAIQLNVFQYLTRLLQSLASGGNDCTTSTACMCVYGLLSFVLTSLELHTLGNQQDIIDT 402
gi|22046118|ref    GTAIQLNVFQYLTRLLQSLASGGNDCTTSTACMCVYGLLSFVLTSLELHTLGNQQDIIDT 420
gi|23618434|ref    ------------------------------------------------------------ 1
gi|13529308|gb|    ------------------------------------------------------------ 1
gi|19343754|gb|    ------------------------------------------------------------ 1

430       440       450       460       470       480
                    ....|....|....|....|....|....|....|....|....|....|....|....|
SEQ ID NO: 2       ACEVLADPSLPELFWGTEPTSGLGIILDSVCGMFPHLLSPLLQLLRALVSGKSTAKKVYS 470
gi|1136398|dbj|    ACEVLADPSLPELFWGTEPTSGLGIILDSVCGMFPHLLSPLLQLLRALVSGKSTAKKVYS 462
gi|22046118|ref    ACEVLADPSLPELFWGTEPTSGLGIILDSVCGMFPHLLSPLLQLLRALVSGKSTAKKVYS 480
gi|23618434|ref    ------------------------------------------------------------ 1
gi|13529308|gb|    ------------------------------------------------------------ 1
gi|19343754|gb|    ------------------------------------------------------------ 1

490       500       510       520       530       540
                    ....|....|....|....|....|....|....|....|....|....|....|....|
SEQ ID NO: 2       FLDKMSFYNELYKHKPHDVISHEDGTLWRRQTPKLLYPLGGQTNLRIPQGTVGQVMLDDR 530
gi|1136398|dbj|    FLDKMSFYNELYKHKPHDVISHEDGTLWRRQTPKLLYPLGGQTNLRIPQGTVGQVMLDDR 522
gi|22046118|ref    FLDKMSFYNELYKHKPHDVISHEDGTLWRRQTPKLLYPLGGQTNLRIPQGTVGQVMLDDR 540
gi|23618434|ref    ------------------------------------------------------------ 1
gi|13529308|gb|    ------------------------------------------------------------ 1
gi|19343754|gb|    ------------------------------------------------------------ 1

550       560       570       580       590       600
                    ....|....|....|....|....|....|....|....|....|....|....|....|
SEQ ID NO: 2       AYLVRWEYSYSSWTLFTCEIEMLLHVVSTADVIQHCQRVKPIIDLVHKVISTDLSIADCL 590
gi|1136398|dbj|    AYLVRWEYSYSSWTLFTCEIEMLLHVVSTADVIQHCQRVKPIIDLVHKVISTDLSIADCL 582
gi|22046118|ref    AYLVRWEYSYSSWTLFTCEIEMLLHVVSTADVIQHCQRVKPIIDLVHKVISTDLSIADCL 600
gi|23618434|ref    ------------------------------------------------------------ 1
gi|13529308|gb|    ------------------------------------------------------------ 1
gi|19343754|gb|    ------------------------------------------------------------ 1

610       620       630       640       650       660
                    ....|....|....|....|....|....|....|....|....|....|....|....|
SEQ ID NO: 2       LPITSRIYMLLQRLTTVISPPVDVIASCVNCLTVLAARNPAKYWTDLRHTGFLPFVAHPV 650
gi|1136398|dbj|    LPITSRIYMLLQRLTTVISPPVDVIASCVNCLTVLAARNPAKVWTDLRHTGFLPFVAHPV 642
gi|22046118|ref    LPITSRIYMLLQRLTTVISPPVDVIASCVNCLTVLAARNPAKVWTDLRHTGFLPFVAHPV 660
gi|23618434|ref    ------------------------------------------------------------ 1
gi|13529308|gb|    ------------------------------------------------------------ 1
gi|19343754|gb|    ------------------------------------------------------------ 1

670       680       690       700       710       720
                    ....|....|....|....|....|....|....|....|....|....|....|....|
SEQ ID NO: 2       SSLSQMISAEGMNAGGYGNLLMNSEQPQGEYGVTIAFLRLITTLVKGQLGSTQSQGLVPC 710
gi|1136398|dbj|    SSLSQMISAEGMNAGGYGNLLMNSEQPQGEYGVTIAFLRLITTLVKGQLGSTQSQGLVPC 702
gi|22046118|ref    SSLSQMISAEGMNAGGYGNLLMNSEQPQGEYGVTIAFLRLITTLVKGQLGSTQSQGLVPC 720
gi|23618434|ref    ------MIQMISAEGMNAGGYGSLLMNSEQPQGEYGVTIAFLRLVTTLMKGQLGSTQSQG 54
gi|13529308|gb|    --------------------------------VTIAFLRLITTLVKGQLGSTQSQGLVPC 28
gi|19343754|gb|    ------------------------------------------------------------ 1
```

TABLE 4-continued

ClustalW Analysis of SEQ ID NO: 2

```
                      730        740        750        760        770        780
                 ....|....|....|....|....|....|....|....|....|....|....|....|
SEQ ID NO: 2     VMFVLKEMLPSYHKWRYNSHGVREQIGCLILELIHAILNLCHETDLHSSHTPSLQFLCIC  770
gi|1136398|dbj|  VMFVLKEMLPSYHKWRYNSHGVREQIGCLILELIHAILNLCHETDLHSSHTPSLQFLCIC  762
gi|22046118|ref| VMFVLKEMLPSYHKWRYNSHGVREQIGCLILELIHAILNLCHETDLHSSHTPSLQFLCIC  780
gi|23618434|ref| ENVPCVMFVLKEMLPSYHKWRYNSHGVRELIGCLILELIHAILNLCQETELHSSHTPSLPS 114
gi|13529308|gb|  VMFVLKEMLPSYHKWRYNSHGVREQIGCLILELIHAILNLCHETDLHSSHTPSLQFLCIC   88
gi|19343754|gb|  ------------------------------------------------------------    1

790        800        810        820        830        840
                 ....|....|....|....|....|....|....|....|....|....|....|....|
SEQ ID NO: 2     SLAYTEAGQTVINIMGIGVDTIDMVMAAQPRSDGAEGQGQGQLLIKTVKLAFSVTNNVIR  830
gi|1136398|dbj|  SLAYTEAGQTVINIMGIGVDTIDMVMAAQPRSDGAEGQGQGQLLIKTVKLAFSVTNNVIR  822
gi|22046118|ref| SLAYTEAGQTVINIMGIGVDTIDMVMAAQPRSDGAEGQGQGQLLIKTVKLAFSVTNNVIR  840
gi|23618434|ref| LCICSSLAYTEACQTVISIMGIGVDTIDDMVMAAQPRSDGPEGQGQGQGQLIKTVKLEAFSVIN 174
gi|13529308|gb|  SLAYTEAGQTVINIMGIGVDTIDMVMAAQPRSDGAEGQGQGQLLIKTVKLAFSVTNNVIR  148
gi|19343754|gb|  ------------------------------------------------------------    1

850        860        870        880        890        900
                 ....|....|....|....|....|....|....|....|....|....|....|....|
SEQ ID NO: 2     LKPPSNVVSPLEQALSQHGAHGNNLIAVLAKYIYHKHDPALPRLAIQLLKRLATVARMSV  890
gi|1136398|dbj|  LKPPSNVVSPLEQALSQHGAHGNNLIAVLAKYIYHKHDPALPRLAIQLLKRLATVAPMSV  882
gi|22046118|ref| LKPPSNVVSPLEQALSQHGAHGNNLIAVLAKYIYHKHDPALPRLAIQLLKRLATVAPMSV  900
gi|23618434|ref| NVIRLKPPSNVVSPLEQALTQHGAHGNNLIAVEAKYIYHRHDPALPRLAIQLLKRLATVA 234
gi|13529308|gb|  LKPPSNVVSPLEQALSQHGAHGNNLIAVLAKYIYHKHDPALPRLAIQLLKRLATVAPMSV  208
gi|19343754|gb|  ------------------------------------------------------------    1

910        920        930        940        950        960
                 ....|....|....|....|....|....|....|....|....|....|....|....|
SEQ ID NO: 2     YACLGNDAAAIRDAFLTRLQSKIEDMRIKVMILEFLTVAVETQPGLIELFLNLEVKDGSD  950
gi|1136398|dbj|  YACLGNDAAAIRDAFLTRLQSKIEDMRIKVMILEFLTVAVETQPGLIELFLNLEVKDGSD  942
gi|22046118|ref| YACLGNDAAAIRDAFLTRLQSKIEDMRIKVMILEFLTVAVETQPGLIELFLNLEVKDGSD  960
gi|23618434|ref| PMSVYACLGSDAAAIRDAFLTRLQSKIEDMRIKVMILEFGTVAVETQPGLIELFENLEVK 294
gi|13529308|gb|  YACLGNDAAAIRDAFLTRLQSKIEDMRIKVMILEFLTVAVETQPGLIELFLNLEVKDGSD  268
gi|19343754|gb|  ------------------------------------------------------------    1

970        980        990       1000       1010       1020
                 ....|....|....|....|....|....|....|....|....|....|....|....|
SEQ ID NO: 2     GSKEFSLGMWSCLHAVLELIDSQQQDRYWCPPLLHRAAIAFLHALWQDRRDSAMLVLRTK 1010
gi|1136398|dbj|  GSKEFSLGMWSCLHAVLELIDSQQQDRYWCPPLLHRAAIAFLHALWQDRRDSAMLVLRTK 1002
gi|22046118|ref| GSKEFSLGMWSCLHAVLELIDSQQQDRYWCPPLLHRAAIAFLHALWQDRRDSAMLVLRTK 1020
gi|23618434|ref| DGSNGSKEFSLGVWSCLHVVLELIDSQQQDRYWCPPLLHRAAIAFLHALWQDRRDSAMLV 354
gi|13529308|gb|  GSKEFSLGMWSCLHAVLELIDSQQQDRYWCPPLLHRAAIAFLHALWQDRRDSAMLVLRTK  328
gi|19343754|gb|  ------------------------------------------------------------    1

1030       1040       1050       1060       1070       1080
                 ....|....|....|....|....|....|....|....|....|....|....|....|
SEQ ID NO: 2     PKFWENLTSPLFGTLSPPSETSEPSILETCALIMKIICLEIYYVVKGSLDQSLKDTLKKF 1070
gi|1136398|dbj|  PKFWENLTSPLFGTLSPPSETSEPSILETCALIMKIICLEIYYVVKGSLDQSLKDTLKKF 1062
gi|22046118|ref| PKFWENLTSPLFGTLSPPSETSEPSILETCALIMKIICLEIYYVVKGSLDQSLKDTLKKF 1080
gi|23618434|ref| LRLKPKFWENLTSPLFGTLSPPSESSEPSVLETCAIIMKIICLEIYYVVKGSLDQSLKDT 414
gi|13529308|gb|  PKFWENLTSPLFGTLSPPSETSEPSILETCALIMKIICLEIYYVVKGSLDQSLKDTLKKF  388
gi|19343754|gb|  ------------------------------------------------------------    1

1090       1100       1110       1120       1130       1140
                 ....|....|....|....|....|....|....|....|....|....|....|....|
SEQ ID NO: 2     SIEKRFAYWSGYVKSLAVHVAETEGSSCTSLLEYQMLVSAWRMLLIIATTHADIMHLTDS 1130
gi|1136398|dbj|  SIEKRFAYWSGYVKSLAVHVAETEGSSCTSLLEYQMLVSAWRMLLIIATTHADIMHLTDS 1122
gi|22046118|ref| SIEKRFAYWSGYVKSLAVHVAETEGSSCTSLLEYQMLVSAWRMLLIIATTHADIMHLTDS 1140
gi|23618434|ref| LKKESSEKREAYWSGYVKSLAVYMADTEGSSCTSLLEYQMLVSAWRLLLILAASHADVMH 474
gi|13529308|gb|  SIEKRFAYWSGYVKSLAVHVAETEGSSCTSLLEYQMLVSAWRMLLIIATTHADIMHLTDS  448
gi|19343754|gb|  ------------------------------------------------------------    1

1150       1160       1170       1180       1190       1200
                 ....|....|....|....|....|....|....|....|....|....|....|....|
SEQ ID NO: 2     VVRRQLFLDVLDGTKALLLVPASVNCLRLGSMKCTLLLILLRQWK----RELGSVDEILG 1186
gi|1136398|dbj|  VVRRQLFLDVLDGTKALLLVPASVNCLRLGSMKCTLLLILLRQWK----RELGSVDEILG 1178
gi|22046118|ref| VVRRQLFLDVLDGTKALLLVPASVNCLRLGSMKCTLLLILLRQWKSILSRELGSVDEILG 1200
gi|23618434|ref| LTDMAVRRQLFLDVLDGTKALLLVAASVNCLRLGSMKCTLLLILLRQWKRELGSVEDILG  534
gi|13529308|gb|  VVRRQLFLDVLDGTKALLLVPASVNCLRLGSMKCTLLLILLRQWK----RELGSVDEILG  504
gi|19343754|gb|  ------------------------------------------------------------    1
```

TABLE 4-continued

ClustalW Analysis of SEQ ID NO: 2

```
                    1210       1220       1230       1240       1250       1260
                ....|....|....|....|....|....|....|....|....|....|....|....|
SEQ ID NO: 2    PLTEILEGVLQADQQLMEKTKAKVFSAFITVLQMKEMKVSDIPQYSQLVLNVCETLQEEV  1246
gi|1136398|dbj| PLTEILEGVLQADQQLMEKTKAKVFSAFITVLQMKEMKVSDIPQYSQLVLNVCETLQEEV  1238
gi|22046118|ref|PLTEILEGVLQADQQLMEKTKAKVFSAFITVLQMKEMKVSDIPQYSQLVLNVCETLQEEV  1260
gi|23618434|ref|PLTEILEGVLQADQQLMEKTKAKVFSAFITVLQMKERVGDIPQYSQLVLNVCETLQEEV   594
gi|13529308|gb| PLTEILEGVLQADQQLMEKTKAKVFSAFITVLQMKEMKVSDIPQYSQLVLNVCETLQEEV   564
gi|19343754|gb| ------------------------------------------------TRPLQEEV         8

1270       1280       1290       1300       1310       1320
                ....|....|....|....|....|....|....|....|....|....|....|....|
SEQ ID NO: 2    IALFDQTRHSLALGSATEDKDSMETDDCSRSRHRDQRDGVCVLGLHLAKELCEVDEDGDS  1306
gi|1136398|dbj| IALFDQTRHSLALGSATEDKDSMETDDCSRSRHRDQRDGVCVLGLHLAKELCEVDEDGDS  1298
gi|22046118|ref|IALFDQTRHSLALGSATEDKDSMETDDCSRSRHRDQRDGVCVLGLHLAKELCEVDEDGDS  1320
gi|23618434|ref|IALFDQTRHSLASDSAAEDKDSMETDDCRPRHRDQRDGVCVLGLHLAKELCEVDEDGDS   654
gi|13529308|gb| IALFDQTRHSLALGSATEDKDSMETDDCSRSRHRDQRDGVCVLGLHLAKELCEVDEDGDS   624
gi|19343754|gb| IALFDQTRHSLASDSAAEDKDSMETDDCPRPRHRDQRDGVCVLGLHLAKELCEVDEDGDS    68

1330       1340       1350       1360       1370       1380
                ....|....|....|....|....|....|....|....|....|....|....|....|
SEQ ID NO: 2    WLQVTRRLPILPTLLTTLEVSLRMKQNLHFTEATLHLLLTLARTQQGATAVAGAGITQSI  1366
gi|1136398|dbj| WLQVTRRLPILPTLLTTLEVSLRMKQNLHFTEATLHLLLTLARTQQGATAVAGAGITQSI  1358
gi|22046118|ref|WLQVTRRLPILPTLLTTLEVSLRMKQNLHFTEATLHLLLTLARTOQGATAVAGAGITQSI  1380
gi|23618434|ref|WLQVTRRLPILPTLLTTLEVSLRMKQNLHFTEAALHLLLTLARTQQGATAVAGAGITQSI   714
gi|13529308|gb| WLQVTRRLPILPTLLTTLEVSLRMKQNLHFTEATLHLLLTLARTQQGATAVAGAGITQSI   684
gi|19343754|gb| WLQVTRRLPILPTLLTTLEVSLRMKQNLHFTEAALHLLLTLARTQQGATAVAGAGITQSI   128

1390       1400       1410       1420       1430       1440
                ....|....|....|....|....|....|....|....|....|....|....|....|
SEQ ID NO: 2    CLPLLSVYQLSTNGTAQTPSASRKSLDAPSWPGVYRLSMSLMEQLLKTLRYNFLPEALDF  1426
gi|1136398|dbj| CLPLLSVYQLSTNGTAQTPSASRKSLDAPSWPGVYRLSMSLMEQLLKTLRYNFLPEALDF  1418
gi|22046118|ref|CLPLLSVYQLSTNGTAQTPSASRKSLDAPSWPGVYRLSMSLMEQLLKTLRYNFLPEALDF  1440
gi|23618434|ref|CLPLLSVYQLSSNGTGQTPSTSRKSLDAPSWPGVYRLSMSLMERLLKTLRYNFLTEALDF   774
gi|13529308|gb| CLPLLSVYQLSTNGTAQTPSASRKSLDAPSWPGVYRLSMSLMEQLLKTLRYNFLPEALDF   744
gi|19343754|gb| CLPLLSVYQLSSNGTGQTPSTSRKSLDAPSWPGVYRLSMSLMERLLKTLRYNFLTEALDF   188

1450       1460       1470       1480       1490       1500
                ....|....|....|....|....|....|....|....|....|....|....|....|
SEQ ID NO: 2    VGVHQERTLQCLNAVRTVQSLACLEEADHTVGFILQLSNFMKEWHFHLPQLMRDIQVNLG  1486
gi|1136398|dbj| VGVHQERTLQCLNAVRTVQSLACLEEADHTVGFILQLSNFMKEWHFHLPQLMRDIQVNLG  1478
gi|22046118|ref|VGVHQERTLQCLNAVRTVQSLACLEEADHTVGFILQLSNFMKEWHFHLPQLMRDIQVNLG  1500
gi|23618434|ref|VGVHQERTLQCLNAVRTVQSLACLEEADHTVGFILQLSHFRKEWHFHLPQLMRDXQVNLG   834
gi|13529308|gb| VGVHQERTLQCLNAVRTVQSLACLEEADHTVGFILQLSNFMKEWHFHLPQLMRDIQV-G-   802
gi|19343754|gb| VGVHQERTLQCLNAVKTVQSLACLEEADHTVGFILQSHFRKEWHFHLPQLMRDXQVNLG   248

1510       1520       1530       1540       1550       1560
                ....|....|....|....|....|....|....|....|....|....|....|....|
SEQ ID NO: 2    YLCQACTSLLHSRKMLQHYLQNKNGDGLPSAVAQRVQRP---PSAASAAPSSSKQPAA--  1541
gi|1136398|dbj| YLCQACTSLLHSRKMLQHYLQNKNGDGLPSAVAQRVQRP---PSAASAAPSSSKQPAA--  1533
gi|22046118|ref|YLCQACTSLLHSRKMLQHYLQNKNGDGLPSAVAQRVQRP---PSAASAAPSSSKQPAA--  1555
gi|23618434|ref|YLCQACTSLLHSRKMLQHYLQNKNGDGLPSAVTPRAQRPSTTTTTTTTTALATPAGCSS   894
gi|13529308|gb| ----AQDGVLESGVMLGDREAVRSHWGIPSEEQDVPER------------------G---   837
gi|19343754|gb| YLCQACTSLLHSRKMLQHYLQNKNGDGLPSAVTPRAQRPSTTTTTTTTTALATPAGCSS   308

1570       1580       1590       1600       1610       1620
                ....|....|....|....|....|....|....|....|....|....|....|....|
SEQ ID NO: 2    -----DTEASEQQALHTVQYGLLKILSKTLAALRHFTPDVCQILLDQSLDLAEYNLFLAL  1596
gi|1136398|dbj| -----DTEASEQQALHTVQYGLLKILSKTLAALRHFTPDVCQILLDQSLDLAEYNLFLAL  1588
gi|22046118|ref|-----DTEASEQRALHTVQYGLLKILSKTLAALRHFTPDVCQILLDQSLDLAEYNLFLAL  1610
gi|23618434|ref|KQPTADTEASEQRALHTVQYGLLKILSKTLAALRHFTPDVCQILLDQSLDLAEYNLFLAL   954
gi|13529308|gb| ------------------LFPWGAQGLSCAYSG---------------------------   853
gi|19343754|gb| KQPTADTEASEQKALHTVQYGLLKILSRTLAALRHFTPDVCQILLDQSLDLAEYNLFLAL   368

1630       1640       1650       1660       1670       1680
                ....|....|....|....|----|....|....|....|....|....|....|....|
SEQ ID NO: 2    SFTTPTFDSEVAPSFGTLLATVNVALNMLGELDKKKEPLTQAVGLSTQAEGTRTLKSLLM  1656
gi|1136398|dbj| SFTTPTFDSEVAPSFGTLLATVNVALNMLGELDKKKEPLTQAVGLSTQAEGTRTLKSLLM  1648
gi|22046118|ref|SFTTPTFDSEVAPSFGTLLATVNVALNMLGELDKKKEPLTQAVGLSTQAEGTRTLKSLLM  1670
gi|23618434|ref|SFTTPTFDSEVAPSFGTLLATVNVALNMLGELDKKKESLTQAVGLSTQAEGTRTLKSLLM  1014
gi|13529308|gb| ------------------------------------------------------------   853
gi|19343754|gb| SFTTPTFDSEVAPSFGTLLATVNVALNMLGELDKKKESLTQAVGLSTQAEGTRTLKSLLM   428
```

TABLE 4-continued

ClustalW Analysis of SEQ ID NO: 2

```
                  1690       1700       1710       1720       1730       1740
              ....|....|....|....|....|....|....|....|....|....|....|....|
SEQ ID NO: 2  FTMENCFYLLISQA.. RYLRDPAVHPRDKQRMKQELSSELSTLLSSLSRYFRRGAPSSPA T  1716
gi|1136398|dbj| FTMENCFYLLISQA.. RYLRDPAVHPRDKQRMKQELSSELSTLLSSLSRYFRRGAPSSPA T  1708
gi|22046118|ref FTMENCFYLLISQA.. RYLRDPAVHPRDKQRMKQELSSELSTLLSSLSRYFRRGAPSSPA T  1730
gi|23618434|ref FTMENCFYLLISQA.. RYLRDPAVHPRDKQRMKQELSSELSTLLSSLSRYFRRGAPSSPA A  1074
gi|13529308|gb| ------------------------------------------------------------  853
gi|19343754|gb| FTMENCFYLLISQA.. RYLRDPAVHPRDKQRMKQELSSELSTLLSSLSRYFRRGAPSSPA A  488

1750       1760       1770
                       ....|....|....|....|....|....|..
SEQ ID NO: 2  GVLPSPQGK. TSLSKASPESQEPLIQLVQAFVRH .QR  1753
gi|1136398|dbj| GVLPSPQGK. TSLSKASPESQEPLIQLVQAFVRH .QR  1745
gi|22046118|ref GVLPSPQGK. TSLSKASPESQEPLIQLVQAFVRH .QR  1767
gi|23618434|ref GVLPSPQGK. TSLSKASPESQEPLIQLVQAFVRH .QR  1111
gi|13529308|gb| ---------------------------------------  853
gi|19343754|gb| GVLPSPQGK. TSLSKASPESQEPLIQLVQAFVRH .QR  525
```

Residues 1-14 of SEQ ID NO:2 are referred to herein as SEQ ID NO:20. The fragment of SEQ ID NO:21 that includes amino acids 1-6 is referred to herein as SEQ ID NO:26.

BFLP0169 Nucleic Acids

The nucleic acids of the invention include those that encode a BFLP0169 polypeptide or protein. As used herein, the terms polypeptide and protein are interchangeable.

In some embodiments, a BFLP0169 nucleic acid encodes a mature BFLP0169 polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The invention includes mutant or variant nucleic acids of SEQ ID NO:1, or a fragment thereof, any of whose bases may be changed from the corresponding bases shown in SEQ ID NO:1, while still encoding a protein that maintains at least one of its BFLP0169-like activities and physiological functions (i.e., modulating angiogenesis, neuronal development).

The invention further includes the complement of the nucleic acid sequence of SEQ ID NO:1, including fragments, derivatives, analogs and homologs thereof. The invention additionally includes nucleic acids or nucleic acid fragments, or complements thereto, whose structures include chemical modifications.

One aspect of the invention pertains to isolated nucleic acid molecules that encode BFLP0169 proteins or biologically active portions thereof. Also included are nucleic acid fragments sufficient for use as hybridization probes to identify BFLP0169-encoding nucleic acids (e.g., BFLP0169 mRNA) and fragments for use as polymerase chain reaction (PCR) primers for the amplification or mutation of BFLP0169 nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BFLP0169 nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, or a complement thereof, can be isolated using standard molecular biology techniques and the sequence information provided herein. Using all or a portion of the nucleic acid sequence of SEQ ID NO:1 as a hybridization probe, BFLP0169 nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to BFLP0169 nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO:1, or a portion of this nucleotide sequence. A nucleic acid molecule that is complementary to the nucleotide sequence shown in SEQ ID NO:1 is one that is sufficiently complementary to the nucleotide sequence shown in SEQ ID NO:1 that it can hydrogen bond with little or no mismatches to the nucleotide sequence shown in SEQ ID NO:1, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, e.g., a fragment that can be used as a probe or primer, or a fragment encoding a biologically active portion of BFLP0169 . Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a BFLP0169 polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a BFLP0169 polypeptide of species other than humans, including, but not limited to, mammals, and thus can include, e.g., mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human BFLP0169 protein. Homologous nucleic acid sequences include those nucleic acid sequences that encode conservative amino acid substitutions (see below) in SEQ ID NO:2, as well as a polypeptide having BFLP0169 activity. Biological activities of the BFLP0169 proteins are described below. A homologous amino acid sequence does not encode the amino acid sequence of a human BFLP0169 polypeptide.

The nucleotide sequence determined from the cloning of the human BFLP0169 gene allows for the generation of probes and primers designed for use in identifying and/or cloning BFLP0169 homologues in other cell types, e.g., from other tissues, as well as BFLP0169 homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1; or an anti-sense strand nucleotide sequence of SEQ ID NO:1; or of a naturally occurring mutant of SEQ ID NO:1.

Probes based on the human BFLP0169 nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a BFLP0169 protein, such as by measuring a level of a BFLP0169-encoding nucleic acid in a sample of cells from a subject e.g., detecting BFLP0169 mRNA levels or determining whether a genomic BFLP0169 gene has been mutated or deleted.

A "polypeptide having a biologically active portion of BFLP0169" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of BFLP0169" can be prepared by isolating a portion of SEQ ID NO:1 that encodes a polypeptide having a BFLP0169 biological activity (biological activities of the BFLP0169 proteins are described below), expressing the encoded portion of BFLP0169 protein (e.g., by recombinant expression in vitro) and assessing the activity of the encoded portion of BFLP0169.

The invention also provides polymorphic forms of BFLP0169 nucleic acid sequences as well as methods of detecting polymorphic sequences in BFLP0169 sequences The polymorphic forms include genomic sequences corresponding to exons and/or introns associated with BFLP0169.

Individuals carrying polymorphic alleles of the invention may be detected at either the DNA, the RNA, or the protein level using a variety of techniques that are well known in the art. The present methods usually employ pre-characterized polymorphisms. That is, the genotyping location and nature of polymorphic forms present at a site have already been determined. The availability of this information allows sets of probes to be designed for specific identification of the known polymorphic forms.

The genomic DNA used for the diagnosis may be obtained from any nucleated cells of the body, such as those present in peripheral blood, urine, saliva, buccal samples, surgical specimen, and autopsy specimens. The DNA may be used directly or may be amplified enzymatically in vitro through use of PCR or other in vitro amplification methods such as the ligase chain reaction (LCR), strand displacement amplification (SDA), self-sustained sequence replication (3SR), prior to mutation analysis.

The detection of polymorphisms in specific DNA sequences, can be accomplished by a variety of methods including, but not limited to, restriction-fragment-length-polymorphism detection based on allele-specific restriction-endonuclease cleavage, hybridization with allele-specific oligonucleotide probes, including immobilized oligonucleotides or oligonucleotide arrays, allele-specific PCR, mismatch-repair detection (MRD), binding of MutS protein, denaturing-gradient gel electrophoresis (DGGE), single-strand-conformation-polymorphism detection, RNAase cleavage at mismatched base-pairs, chemical or enzymatic cleavage of heteroduplex DNA, methods based on allele specific primer-extension, genetic bit analysis (GBA), the oligonucleotide-ligation assay (OLA), the allele-specific ligation chain reaction (LCR), gap-LCR, radioactive and/or fluorescent DNA sequencing using standard procedures well known in the art, and peptide nucleic acid (PNA) assays.

BFLP0169 Variants

The invention further encompasses nucleic acid molecules that differ from the nucleotide sequences shown in SEQ ID NO:1 due to the degeneracy of the genetic code. These nucleic acids thus encode the same BFLP0169 protein as that encoded by the nucleotide sequence shown in SEQ ID NO:1, e.g., the polypeptide of SEQ ID NO:2. In another embodiment, an isolated nucleic acid molecule of the invention has a nucleotide sequence encoding a protein having an amino acid sequence shown in SEQ ID NO:2.

In addition to the human BFLP0169 nucleotide sequence shown in SEQ ID NO:1, it will be appreciated by those skilled in the art that DNA sequence polymorphisms that lead to changes in the amino acid sequences of BFLP0169 may exist within a population (e.g., the human population). Such genetic polymorphism in the BFLP0169 gene may exist among individuals within a population due to natural allelic variation. As used herein, the terms "gene" and "recombinant gene" refer to nucleic acid molecules comprising an open reading frame encoding a BFLP0169 protein, preferably a mammalian BFLP0169 protein. Such natural allelic variations can typically result in 1-5% variance in the nucleotide sequence of the BFLP0169 gene. Any and all such nucleotide variations and resulting amino acid polymorphisms in BFLP0169 that are the result of natural allelic variation and that do not alter the functional activity of BFLP0169 are intended to be within the scope of the invention.

Moreover, nucleic acid molecules encoding BFLP0169 proteins from other species, and thus that have a nucleotide sequence that differs from the human sequence of SEQ ID NO:1 are intended to be within the scope of the invention. Nucleic acid molecules corresponding to natural allelic variants and homologues of the BFLP0169 cDNAs of the invention can be isolated based on their homology to the human BFLP0169 nucleic acids disclosed herein using the human cDNAs, or a portion thereof, as a hybridization probe according to standard hybridization techniques under stringent hybridization conditions. For example, a soluble human BFLP0169 cDNA can be isolated based on its homology to human membrane-bound BFLP0169. Likewise, a membrane-bound human BFLP0169 cDNA can be isolated based on its homology to soluble human BFLP0169.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding BFLP0169 proteins derived from species other than human) or other related sequences (e.g., paralogs) can be obtained by low, moderate or high stringency hybridization with all or a portion of the particular human sequence as a probe using methods well known in the art for nucleic acid hybridization and cloning. Thus, the present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 4

Stringency Conditions

| Stringency Condition | Polynucleotide Hybrid | Hybrid Length (bp)[1] | Hybridization Temperature and Buffer[H] | Wash Temperature and Buffer[H] |
|---|---|---|---|---|
| A | DNA:DNA | ≥50 | 65° C.; 1 × SSC -or- 42° C.; 1 × SSC, 50% formamide | 65° C.; 0.3 × SSC |
| B | DNA:DNA | <50 | $T_B^*$; 1 × SSC | $T_B^*$; 1 × SSC 67° C.; 0.3 × SSC |
| C | DNA:RNA | ≥50 | 67° C.; 1 × SSC -or- 45° C.; 1 × SSC, 50% formamide | |
| D | DNA:RNA | <50 | $T_D^*$; 1 × SSC | $T_D^*$; 1 × SSC 70° C.; 0.3 × SSC |
| E | RNA:RNA | ≥50 | 70° C.; 1 × SSC -or- 50° C.; 1 × SSC, 50% formamide | |
| F | RNA:RNA | <50 | $T_F^*$; 1 × SSC | $T_F^*$; 1 × SSC 65° C.; 1 × SSC |
| G | DNA:DNA | ≥50 | 65° C.; 4 × SSC -or- 42° C.; 4 × SSC, 50% formamide | |
| H | DNA:DNA | <50 | $T_H^*$; 4 × SSC | $T_H^*$; 4 × SSC 67° C.; 1 × SSC |
| I | DNA:RNA | ≥50 | 67° C.; 4 × SSC -or- 45° C.; 4 × SSC, 50% formamide | |
| J | DNA:RNA | <50 | $T_J^*$; 4 × SSC | $T_J^*$; 4 × SSC 67° C.; 1 × SSC |
| K | RNA:RNA | ≥50 | 70° C.; 4 × SSC -or- 50° C.; 4 × SSC, 50% formamide | |
| L | RNA:RNA | <50 | $T_L^*$; 2 × SSC | $T_L^*$; 2 × SSC 50° C.; 2 × SSC |
| M | DNA:DNA | >50 | 50° C.; 4 × SSC -or- 40° C.; 6 × SSC, 50% formamide | |
| N | DNA:DNA | <50 | $T_N^*$; 6 × SSC | $T_N^*$; 6 × SSC 55° C.; 2 × SSC |
| O | DNA:RNA | >50 | 55° C.; 4 × SSC -or- 42° C.; 6 × SSC, 50% formamide | |
| P | DNA:RNA | <50 | $T_P^*$; 6 × SSC | $T_P^*$; 6 × SSC 60° C.; 2 × SSC |
| Q | RNA:RNA | >50 | 60° C.; 4 × SSC -or- 45° C.; 6 × SSC, 50% formamide | |
| R | RNA:RNA | <50 | $T_R^*$; 4 × SSC | $T_R^*$; 4 × SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1 × SSPE is 0.15 M NaCl, 10 mM NaH$_2$PO$_4$, and 1.25 mM EDTA, pH 7.4) can be substituted for SSC (1 × SSC is 0.15 M NaCl and 15 mM sodium citrate) in the hybridization and wash buffers; washes are performed for 15 minutes after hybridization is complete.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6(log$_{10}$Na$^+$) + 0.41(% G + C) − (600/N), where N is the number of bases in the hybrid, and Na$^+$ is the concentration of sodium ions in the hybridization buffer (Na$^+$ for 1 × SSC = 0.165 M).

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C.

In a third embodiment, a nucleic acid that is hybridizable to the nucleic acid molecule comprising the nucleotide sequence of SEQ ID NO:1, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C.

Conservative Mutations

In addition to naturally-occurring allelic variants of the BFLP0169 sequence that may exist in the population, the skilled artisan will further appreciate that changes can be introduced by mutation into the nucleotide sequence of SEQ ID NO:1, thereby leading to changes in the amino acid sequence of the encoded BFLP0169 protein, without altering the functional ability of the BFLP0169 protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of BFLP0169 without altering the biological activity, whereas an "essential" amino acid residue is required for biological activity. For example, altering amino acid residues that are conserved among the BFLP0169 proteins of the present invention, is likely to result in loss of activity of the BFLP0169 protein.

Another aspect of the invention pertains to nucleic acid molecules encoding BFLP0169 proteins that contain changes in amino acid residues that are not essential for activity. Such BFLP0169 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:2. Preferably, the protein encoded by the nucleic acid is at least about 80% homologous to SEQ ID NO:2, more preferably at least about 90%, 95%, 98%, and most preferably at least about 99% homologous to SEQ ID NO:2.

An isolated nucleic acid molecule encoding a BFLP0169 protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein.

Mutations can be introduced into the nucleotide sequence of SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in BFLP0169 is replaced with another amino acid residue from the same side chain family. Alternatively, in another embodiment, mutations can be introduced randomly along all or part of a BFLP0169 coding sequence, such as by saturation mutagenesis, and the resultant mutants can be screened for BFLP0169 biological activity to identify mutants that retain activity. Following mutagenesis of SEQ ID NO:1 the encoded protein can be expressed by any recombinant technology known in the art and the activity of the protein can be determined.

In one embodiment, a mutant BFLP0169 protein can be assayed for (1) the ability to form protein:protein interactions with other BFLP0169 proteins, other cell-surface proteins, or biologically active portions thereof, (2) complex formation between a mutant BFLP0169 protein and a BFLP0169 receptor; (3) the ability of a mutant BFLP0169 protein to bind to an intracellular target protein or biologically active portion thereof; (e.g., avidin proteins); (4) the ability to bind BFLP0169 protein; or (5) the ability to specifically bind an anti-BFLP0169 protein antibody.

Antisense BFLP0169 Nucleic Acids

Another aspect of the invention pertains to isolated antisense nucleic acid molecules that are hybridizable to or complementary to the nucleic acid molecule comprising the nucleotide sequence of SEQ ID NO:1, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire BFLP0169 coding strand, or to only a portion thereof. Nucleic acid molecules encoding fragments, homologs, derivatives and analogs of a BFLP0169 protein of SEQ ID NO:2, or antisense nucleic acids complementary to a BFLP0169 nucleic acid sequence of SEQ ID NO:1 are additionally provided.

In one embodiment, an antisense nucleic acid molecule is antisense to a "coding region" of the coding strand of a nucleotide sequence encoding BFLP0169. The term "coding region" refers to the region of the nucleotide sequence comprising codons which are translated into amino acid residues (e.g., the protein coding region of human BFLP0169 corresponds to SEQ ID NO:2). In another embodiment, the antisense nucleic acid molecule is antisense to a "noncoding region" of the coding strand of a nucleotide sequence encoding BFLP0169. The term "noncoding region" refers to 5' and 3' sequences which flank the coding region that are not translated into amino acids (i.e., also referred to as 5' and 3' untranslated regions).

Given the coding strand sequences encoding BFLP0169 disclosed herein (e.g., SEQ ID NO:1), antisense nucleic acids of the invention can be designed according to the rules of Watson and Crick or Hoogsteen base pairing. The antisense nucleic acid molecule can be complementary to the entire coding region of BFLP0169 mRNA, but more preferably is an oligonucleotide that is antisense to only a portion of the coding or noncoding region of BFLP0169 mRNA. For example, the antisense oligonucleotide can be complementary to the region surrounding the translation start site of BFLP0169 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BFLP0169 protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-o-methylribonucleotide.

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

BFLP0169 Ribozymes and PNA Moieties

In still another embodiment, an antisense nucleic acid of the invention is a ribozyme.

Ribozymes are catalytic RNA molecules with ribonuclease activity that are capable of cleaving a single-stranded nucleic acid, such as a mRNA, to which they have a complementary region. Thus, ribozymes (e.g., hammerhead ribozymes) can be used to catalytically cleave BFLP0169 mRNA transcripts to thereby inhibit translation of BFLP0169 mRNA. A ribozyme having specificity for a BFLP0169-encoding nucleic acid can be designed based upon the nucleotide sequence of a BFLP0169 DNA disclosed herein (i.e., SEQ ID NO:1). For example, a derivative of a Tetrahymena L-19 IV S RNA can be constructed in which the nucleotide sequence of the active site is complementary to the nucleotide sequence to be cleaved in a BFLP0169-encoding mRNA. Alternatively, BFLP0169 mRNA can be used to select a catalytic RNA having a specific ribonuclease activity from a pool of RNA molecules.

Alternatively, BFLP0169 gene expression can be inhibited by targeting nucleotide sequences complementary to the regulatory region of the BFLP0169 (e.g., the BFLP0169 promoter and/or enhancers) to form triple helical structures that prevent transcription of the BFLP0169 gene in target cells.

In various embodiments, the nucleic acids of BFLP0169 can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols.

PNAs of BFLP0169 can be used in therapeutic and diagnostic applications. For example, PNAs can be used as antisense or antigene agents for sequence-specific modulation of gene expression by, e.g., inducing transcription or translation arrest or inhibiting replication. PNAs of BFLP0169 can also be used, e.g., in the analysis of single base pair mutations in a gene by, e.g., PNA directed PCR clamping; as artificial restriction enzymes when used in combination with other enzymes, e.g., S1 nucleases; or as probes or primers for DNA sequence and hybridization.

In another embodiment, PNAs of BFLP0169 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of BFLP0169 can be generated that may combine the advantageous properties of PNA and DNA.

The oligonucleotide may include other appended groups such as peptides (e.g., for targeting host cell receptors in vivo), or agents facilitating transport across the cell membrane or the blood-brain barrier. In addition, oligonucleotides can be modified with hybridization triggered cleavage agents or intercalating agents. To this end, the oligonucleotide may be conjugated to another molecule, e.g., a peptide, a hybridization triggered cross-linking agent, a transport agent, a hybridization-triggered cleavage agent, etc.

BFLP0169 Interfering Nucleic Acids

Also provided by the invention is an isolated double-stranded nucleic acid (DNA or RNA) that is capable of mediating specific inhibition of BFLP0169 gene expression. In preferred embodiments, one or both strands of the double-stranded molecule is an RNA molecule. Preferably, each RNA strand has a length from 19-25, particularly from 19-23 nucleotides, more particularly from 20-22 nucleotides, and is capable of mediating BFLP0169 target-specific nucleic acid modifications, particularly RNA interference and/or DNA methylation. The double-stranded BFLP0169 molecule may be double stranded or have an overhang at one or both the 5' and/or 3' terminus. For example, the molecule may have a 3' overhang. The length of the 3'-overhang can be, e.g., 1-6 nucleotides, 2-5 nucleotides, 3-4 nucleotides, or 2 nucleotides. The length of the overhang may be the same or different for each strand. In one embodiment, dsRNAs are composed of two 21 nucleotide strands that are paired such that 1, 2, or 3 nucleotide overhangs are present on both ends of the double-stranded RNA.

The RNA strands preferably have 3'-hydroxyl groups. The 5'-terminus preferably includes a phosphate, diphosphate, triphosphate or hydroxyl group. If desired, the 3'-overhangs may be stabilized against degradation. For example, they may be selected such that they consist of purine nucleotides, particularly adenosine or guanosine nucleotides. Alternatively, pyrimidine nucleotides may be replaced with modified analogues, e.g. substitution of uridine-2 nucleotide 3' overhangs by 2'-deoxythymidine is tolerated, and does not affect the efficiency of RNA interference. The RNA molecule may contain at least one modified nucleotide analogue. The nucleotide analogues may be located at positions where the target-specific activity, e.g. the RNAi mediating activity is not substantially affected. The modified nucleotide is preferably present in a region at the 5'-end and/or the 3'-end of the double-stranded RNA molecule. In some embodiments, overhangs are stabilized by incorporating modified nucleotide analogues.

Nucleotide analogues can include sugar- or backbone-modified ribonucleotides. Other suitable nucleotides include a non-naturally occurring nucleobase instead of a naturally occurring nucleobases. For example, analogues can include uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. In preferred sugar-modified ribonucleotides the 2' OH-group is replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. In a preferred embodiment, where backbone-modified ribonucleotides are used as the phosphoester group connecting to adjacent ribonucleotides, they are replaced by a modified group, e.g. a phosphothioate group. It should be noted that the above modifications may be combined.

The BFLP0169 interfering RNA molecule can be a naturally isolated RNA molecule or can a synthetic RNA molecule. Preferably, the BFLP0169 interfering RNA molecule is substantially free from contaminants occurring in cell extracts, e.g. from *Drosophila* embryos. Further, the BFLP0169 interfering RNA molecule is preferably substantially free from any non-target-specific contaminants, particularly non-target-specific RNA molecules e.g. from contaminants occurring in cell extracts.

Isolated double-stranded BFLP0169 interfering molecules can be used for mediating BFLP0169 target-specific nucleic acid modifications, particularly RNAi, in mammalian cells, particularly in human cells.

The sequence of the double-stranded BFLP0169 interfering molecule of the present invention is of sufficient identity to a nucleic acid BFLP0169 target molecule in order to effect target-specific interference of BFLP0169 gene expression and/or DNA methylation. Preferably, the sequence has an identity of at least 50%, particularly of at least 70% to the desired target molecule in the double-stranded portion of the RNA molecule. More preferably, the identity is at least 85% and most preferably 100% in the double-stranded portion of the RNA molecule. The identity of a BFLP0169 double-stranded interfering RNA molecule to a predetermined nucleic acid target molecule, e.g. an BFLP0169 mRNA target molecule with the sequence shown in SEQ ID NO:1, may be determined using the equation: $I=(n/L)\times100$, wherein I is the identity in percent, n is the number of identical nucleotides in the double-stranded portion of the ds RNA and the target and L is the length of the sequence overlap of the double-stranded portion of the dsRNA and the target.

Alternatively, the identity of the double-stranded RNA molecule relative to the target sequence may also be defined including the 3' overhang, particularly an overhang having a length from 1-3 nucleotides. In this case the sequence identity is preferably at least 50%, more preferably at least 70% and most preferably at least 85% to the target sequence. For example, the nucleotides from the 3' overhang and up to 2 nucleotides from the 5' and/or 3' terminus of the double strand may be modified without significant loss of activity.

A double-stranded BFLP0169 RNA molecule may be prepared by a method that includes synthesizing two RNA strands each having a length from 19-25, e.g. from 19-23 nucleotides, wherein said RNA strands are capable of forming a double-stranded RNA molecule, wherein preferably at least one strand has a 3'-overhang from 1-5 nucleotides, and (b) combining the synthesized RNA strands under conditions, wherein a a double-stranded RNA molecule is formed. The double-stranded RNA molecule is capable of mediating target-specific nucleic acid modifications, particularly RNA interference and/or DNA methylation.

Methods of synthesizing RNA molecules are known in the art. The single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase.

A further aspect of the present invention relates to a method of mediating BFLP0169-specific nucleic acid modifications, particularly RNA interference and/or DNA methylation in a cell or an organism by contacting the cell or organism with the double-stranded RNA molecule of the invention under conditions wherein target-specific nucleic acid modifications may occur and mediating a target-specific nucleic acid modification effected by the double-stranded RNA towards a BFLP0169 target nucleic acid.

BFLP0169 Polypeptides

A BFLP0169 polypeptide of the invention includes the BFLP0169-like protein whose sequence is provided in SEQ ID NO:2. The invention also includes a mutant or variant form of the disclosed BFLP0169 polypeptide, or of any of the fragments of the herein disclosed BFLP0169 polypeptide sequences.

Thus, a BFLP0169 polypeptide includes one in which any residues may be changed from the corresponding residue shown in SEQ ID NO:2 while still encoding a protein that maintains its BFLP0169-like activities and physiological functions, or a functional fragment thereof. In some embodiments, up to 20% or more of the residues may be so changed in the mutant or variant protein. In some embodiments, the BFLP0169 polypeptide according to the invention is a mature polypeptide.

Rapamycin Binding Domains

To identify regions of a BFLP0169 polypeptide sequence (e.g., a polypeptide including all or a portion of SEQ ID NO:2) containing rapamycin binding domains, the entire coding sequence, or a fragment of a BFLP0169 polypeptide sequence, is tested for its ability to bind rapamycin. Any technique known in the art for determining binding of a polypeptide to a small molecule can be used. For example, rapamycin can be labeled (i.e., with a non-radioactive label or with a radiolabel (e.g., $^{14}C$, $^{32}P$, $^{3}H$, or $^{125}I$), and mixed with a polypeptide containing some or all of a BFLP0169 polypeptide sequence. The polypeptide optionally includes a moiety that facilitates detection, e.g., the polypeptide can be a fusion polypeptide that includes a BFLP0169 sequence and a non-BFLP0169 polypeptide sequence.

A reagent specific for the polypeptide containing the BFLP0169 polypeptide sequence (e.g., an antibody specific for BFLP0169 or a probe specific for the non-BFLP0169 polypeptide in the case of a fusion polypeptide) is added to the mixture. Complexes that bind to the reagent are isolated, and the presence of label, which reveals the presence of rapamycin, is determined.

In general, a BFLP0169-like variant that preserves BFLP0169-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated BFLP0169 proteins, and biologically active portions thereof, or derivatives, fragments, analogs or homologs thereof. Fragments can comprise contiguous stretches of SEQ ID NO:2, or interspersed segments of SEQ ID NO:2. Also provided are polypeptide fragments suitable for use as immunogens to raise anti-BFLP0169 antibodies. In one embodiment, native BFLP0169 proteins can be isolated from cells or tissue sources by an appropriate purification scheme using standard protein purification techniques. In another embodiment, BFLP0169 proteins are produced by recombinant DNA techniques. Alternative to recombinant expression, a BFLP0169 protein or polypeptide can be synthesized chemically using standard peptide synthesis techniques.

A "purified" protein or biologically active portion thereof is substantially free of cellular material or other contaminating proteins from the cell or tissue source from which the BFLP0169 protein is derived, or substantially free from chemical precursors or other chemicals when chemically synthesized. The language "substantially free of cellular material" includes preparations of BFLP0169 protein in which the protein is separated from cellular components of the cells from which it is isolated or recombinantly produced. In one embodiment, the language "substantially free of cellular material" includes preparations of BFLP0169 protein having less than about 30% (by dry weight) of non-BFLP0169 protein (also referred to herein as a "contaminating protein"), more preferably less than about 20% of non-BFLP0169 protein, still more preferably less than about 10% of non-BFLP0169 protein, and most preferably less than about 5% non-BFLP0169 protein. When the BFLP0169 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BFLP0 169 protein in which the protein is separated from chemical precursors or other chemicals that are involved in the synthesis of the protein. In one embodiment, the language "substantially free of chemical precursors or other chemicals" includes preparations of BFLP0169 protein having less than about 30% (by dry weight) of chemical precursors or non-BFLP0 169 chemicals, more preferably less than about 20% chemical precursors or non-BFLP0169 chemicals, still more preferably less than about 10% chemical precursors or non-BFLP0169 chemicals, and most preferably less than about 5% chemical precursors or non-BFLP0169 chemicals.

Biologically active portions of a BFLP0169 protein include peptides comprising amino acid sequences sufficiently homologous to or derived from the amino acid sequence of the BFLP0169 protein, e.g., the amino acid sequence shown in SEQ ID NO:2 that include fewer amino acids than the full length BFLP0169 proteins, and exhibit at least one activity of a BFLP0169 protein. Typically, biologically active portions comprise a domain or motif with at least one activity of the BFLP0169 protein. A biologically active portion of a BFLP0169 protein can be a polypeptide which is, for example, 10, 25, 50, 100 or more amino acids in length.

A biologically active portion of a BFLP0169 protein of the present invention may contain at least one of the above-identified domains conserved between the BFLP0169 proteins. Moreover, other biologically active portions, in which other regions of the protein are deleted, can be prepared by recombinant techniques and evaluated for one or more of the functional activities of a native BFLP0169 protein.

In an embodiment, the BFLP0169 protein has an amino acid sequence shown in SEQ ID NO:2. In other embodiments, the BFLP0169 protein is substantially homologous to SEQ ID NO:2 and retains the functional activity of the protein of SEQ ID NO:2, yet differs in amino acid sequence due to natural allelic variation or mutagenesis, as described in detail below. Accordingly, in another embodiment, the BFLP0169 protein is a protein that comprises an amino acid sequence at least about 45% homologous to the amino acid sequence of SEQ ID NO:2 and retains the functional activity of the BFLP0169 proteins of SEQ ID NO:2.

Determining Homology Between Two or More Sequences

To determine the percent homology of two amino acid sequences or of two nucleic acid sequences, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides BFLP0169 chimeric or fusion proteins. As used herein, a BFLP0169 "chimeric protein" or "fusion protein" comprises a BFLP0169 polypeptide operatively linked to a non-BFLP0169 polypeptide. A "BFLP0169 polypeptide" refers to a polypeptide having an amino acid sequence corresponding to BFLP0169, whereas a "non-BFLP0169 polypeptide" refers to a polypeptide having an amino acid sequence corresponding to a protein that is not substantially homologous to the BFLP0169 protein, e.g., a protein that is different from the BFLP0169 protein and that is derived from the same or a different organism. Within a BFLP0169 fusion protein the BFLP0169 polypeptide can correspond to all or a portion of a BFLP0169 protein. An example of a BFLP0169 fusion polypeptide is one that includes amino acids 21-230 of SEQ ID NO:2 (e.g., a polypeptide that includes amino acids 1-246 or amino acids 21-246 of SEQ ID NO:2). In one embodiment, a BFLP0169 fusion protein comprises at least one biologically active portion of a BFLP0169 protein. In another embodiment, a BFLP0169 fusion protein comprises at least two biologically active portions of a BFLP0169 protein. Within the fusion protein, the term "operatively linked" is intended to indicate that the BFLP0169 polypeptide and the non-BFLP0169 polypeptide are fused in-frame to each other. The non-BFLP0169 polypeptide can be fused to the N-terminus or C-terminus of the BFLP0169 polypeptide.

For example, in one embodiment a BFLP0169 fusion protein comprises a BFLP0169 polypeptide operably linked to either an extracellular domain of a second protein, i.e., non-BFLP0169 protein, or to the transmembrane and intracellular domain of a second protein, i.e., non-BFLP0169 protein. Such fusion proteins can be further utilized in screening assays for compounds that modulate BFLP0169 activity (such assays are described in detail below).

In another embodiment, the fusion protein is a GST-BFLP0169 fusion protein in which the BFLP0169 sequences are fused to the C-terminus of the GST (i.e., glutathione S-transferase) sequences. Such fusion proteins can facilitate the purification of recombinant BFLP0169.

In another embodiment, the fusion protein is a BFLP0169-immunoglobulin fusion protein in which the BFLP0169 sequences comprising one or more domains are fused to sequences derived from a member of the immunoglobulin protein family.

Inhibition of the BFLP0169 ligand/BFLP0169 interaction can be used therapeutically for both the treatment of proliferative and differentiative disorders, e.g., cancer, modulating (e.g., promoting or inhibiting) cell survival as well as immunomodulatory disorders, autoimmunity, transplantation, and inflammation by alteration of cyotokine and chemokine cascade mechanisms. Moreover, the BFLP0169-immunoglobulin fusion proteins of the invention can be used as immunogens to produce anti-BFLP0169 antibodies in a subject, to purify BFLP0169 ligands, and in screening assays to identify molecules that inhibit the interaction of BFLP0169 with a BFLP0169 ligand.

A BFLP0169 chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence. Moreover, many expression vectors are commercially available that already encode a fusion moiety (e.g., a GST polypeptide). A BFLP0169-encoding nucleic acid can be cloned into such an expression vector such that the fusion moiety is linked in-frame to the BFLP0169 protein.

If desired, libraries of fragments of the BFLP0169 protein coding sequence can be used to generate a variegated population of BFLP0169 fragments for screening and subsequent selection of variants of a BFLP0169 protein.

BFLP0169 Antibodies

Also included in the invention are antibodies to BFLP0169 proteins, or fragments of BFLP0169 proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an Fab expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated BFLP0169-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of BFLP0169-related protein that is located on the surface of the protein, e.g., a hydrophilic region. A hydrophobicity analysis of the human BFLP0169-related protein sequence will indicate which regions of a BFLP0169-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation.

The novel nucleic acid encoding the BFLP0169 protein of the invention, or fragments thereof, may further be useful in diagnostic applications, wherein the presence or amount of the nucleic acid or the protein are to be assessed. These materials are further useful in the generation of antibodies that bind immunospecifically to the novel substances of the invention for use in therapeutic or diagnostic methods. The disclosed BFLP0169 protein hasmultiple hydrophilic regions, each of which can be used as an immunogen. In one embodiment, a contemplated BFLP0169 epitope is from about amino acids 20 to 90. In another embodiment, a BFLP0169 epitope is from about amino acids 100 to 130. In additional embodiments, BFLP0169 epitopes are from about amino acids 140 to 220, from about amino acids 240 to 250, from about amino acids 280 to 290, from about amino acids 330 to 340, from about amino acids 370 to 380, from about amino acids 400 to 410, from about amino acids 450 to 520, from about amino acids 530 to 540, from about amino acids 640 to 650, from about amino acids 720 to 730, from about amino acids 800 to 820, from about amino acids 850 to 855, from about amino acids 900 to 910, from about amino acids 920 to 930, from about amino acids 940 to 950, from about amino acids 970 to 990, from about amino acids 1000 to 1030, from about amino acids 1060 to 1080, from about amino acids 1100 to 1110, from about amino acids 1170 to 1180, from about amino acids 1190 to 1210, from about amino acids 1250 to 1280, from about amino acids 1310 to 1320, from about amino acids 1350 to 1370, from about amino acids 1400 to 1420, from about amino acids 1430 to 1440, from about amino acids 1500 to 1560, from about amino acids 1600 to 1610, from about amino acids 1650 to 1690, from about amino acids 1700 to 1710, and from about amino acids 1720 to 1730.

Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof. The term "monoclonal antibody" (MAb) or "monoclonal antibody composition", as used herein, refers to a population of antibody molecules that contain only one molecular species of antibody molecule consisting of a unique light chain gene product and a unique heavy chain gene product.

The antibodies directed against the protein antigens of the invention can further comprise humanized antibodies or human antibodies. The humanized forms of antibodies include chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin.

The antibodies can also be human antibodies, e.g., antibody molecules in which essentially the entire sequences of both the light chain and the heavy chain, including the CDRs, arise from human genes. Human monoclonal antibodies can be prepared by the trioma technique; the human B-cell hybridoma technique and the EBV hybridoma technique.

Human antibodies can also be produced using phage display libraries, or by introducing human immunoglobulin loci into transgenic animals, e.g., mice in which the endogenous immunoglobulin genes have been partially or completely inactivated. Human antibodies may additionally be produced using transgenic nonhuman animals that are modified so as to produce fully human antibodies rather than the animal's endogenous antibodies in response to challenge by an antigen.

The invention also provides single-chain antibodies specific to an antigenic protein of the invention. In addition, methods can be adapted for the construction of $F_{ab}$ expression libraries to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab)2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Also provided by the invention are bispecific antibodies. Bispecific antibodies are monoclonal, preferably human or humanized, antibodies that have binding specificities for at least two different antigens. One of the binding specificities is for an antigenic protein of the invention. The second binding target is any other antigen, and advantageously is a cell-surface protein or receptor or receptor subunit.

If desired, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions.

Bispecific antibodies can be provided as full length antibodies or antibody fragments (e.g. F(ab')$_2$ bispecific antibodies).

Also within the invention are antibodies with more than two valencies (such as trispecific antibodies).

Exemplary bispecific antibodies bind to two different epitopes, at least one of which originates in the protein antigen of the invention.

The invention also includes heteroconjugate antibodies, which include two covalently joined antibodies.

The antibody of the invention can be modified to alter (e.g., enhance or diminish) its function. For example, cysteine residue(s) can be introduced into the Fc region, thereby allowing interchanging disulfide bond formation in this region. The invention also includes immunoconjugates that include an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

The antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

BFLP0169 Recombinant Expression Vectors and Host Cells

Another aspect of the invention pertains to vectors, preferably expression vectors, containing a nucleic acid encoding a BFLP0169 protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genomic sequence into which they have integreated. Moreover, certain vectors are capable of directing the expression of genes to which they are operatively-linked. Such vectors are referred to herein as "expression vectors". "Plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).The term "regulatory sequence" is intended to include promoters, enhancers and other expression control elements (e.g., polyadenylation signals). Regulatory sequences include those that direct constitutive expression of a nucleotide sequence in many types of host cell and those that direct expression of the nucleotide sequence only in certain host cells (e.g., tissue-specific regulatory sequences). The expression vectors of the invention can be introduced into host cells to thereby produce proteins or peptides, including fusion proteins or peptides, encoded by nucleic acids as described herein (e.g., BFLP0169 proteins, mutant forms of BFLP0169 proteins, fusion proteins, etc.).

The recombinant expression vectors of the invention can be designed for expression of BFLP0169 proteins in prokaryotic or eukaryotic cells. For example, BFLP0169 proteins can be expressed in bacterial cells such as *Escherichia coli*, insect cells (using baculovirus expression vectors) yeast cells or mammalian cells. Alternatively, the recombinant expression vector can be transcribed and translated in vitro, for example using T7 promoter regulatory sequences and T7 polymerase.

In yet another embodiment, a nucleic acid of the invention is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific), lymphoid-specific promoters, in particular promoters of T cell receptors and immunoglobulins, neuron-specific promoters (e.g., the neurofilament promoter), pancreas-specific promoters, and mammary gland-specific promoters (e.g., milk whey promoter). Developmentally-regulated promoters are also encompassed, e.g., the murine hox promoters and the α-fetoprotein promoter.

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to BFLP0169 mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, BFLP0169 protein can be expressed in bacterial cells such as E. coli, insect cells, yeast or mammalian cells (such as human, Chinese hamster ovary cells (CHO) or COS cells). Other suitable host cells are known to those skilled in the art.

A gene that encodes a selectable marker (e.g., resistance to antibiotics) is generally introduced into the host cells along with the gene of interest. Various selectable markers include those that confer resistance to drugs, such as G418, hygromycin and methotrexate. A nucleic acid encoding a selectable marker can be introduced into a host cell on the same vector as that encoding BFLP0169 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) BFLP0169 protein. Accordingly, the invention further provides methods for producing BFLP0169 protein using the host cells of the invention. In one embodiment, the method comprises culturing the host cell of invention (into which a recombinant expression vector encoding BFLP0169 protein has been introduced) in a suitable medium such that BFLP0169 protein is produced. In another embodiment, the method further comprises isolating BFLP0169 protein from the medium or the host cell.

Transgenic BFLP0169 Animals

The host cells of the invention can also be used to produce non-human transgenic animals. For example, in one embodiment, a host cell of the invention is a fertilized oocyte or an embryonic stem cell into which BFLP0169 protein-coding sequences have been introduced. Such host cells can then be used to create non-human transgenic animals in which exogenous BFLP0169 sequences have been introduced into their genome or homologous recombinant animals in which endogenous BFLP0169 sequences have been altered. Such animals are useful for studying the function and/or activity of BFLP0169 protein and for identifying and/or evaluating modulators of BFLP0169 protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BFLP0169 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing BFLP0169-encoding nucleic acid into the male pronuclei of a fertilized oocyte (e.g., by microinjection, retroviral infection) and allowing the oocyte to develop in a pseudopregnant female foster animal. Sequences including SEQ ID NO:1 can be introduced as a transgene into the genome of a non-human animal. Alternatively, a non-human homologue of the human BFLP0169 gene, such as a mouse BFLP0169 gene, can be isolated based on hybridization to the human BFLP0169 cDNA (described further supra) and used as a transgene. Intronic sequences and polyadenylation signals can also be included in the transgene to increase the efficiency of expression of the transgene. A tissue-specific regulatory sequence(s) can be operably-linked to the BFLP0169 transgene to direct expression of BFLP0169 protein to particular cells. Methods for generating transgenic animals via embryo manipulation and microinjection, particularly animals such as mice, have become conventional in the art. Similar methods are used for production of other transgenic animals. A transgenic founder animal can be identified based upon the presence of the BFLP0169 transgene in its genome and/or expression of BFLP0169 mRNA in tissues or cells of the animals. A transgenic founder animal can then be used to breed additional animals carrying the transgene. Moreover, transgenic animals carrying a transgene-encoding BFLP0169 protein can further be bred to other transgenic animals carrying other transgenes.

To create a homologous recombinant animal, a vector is prepared which contains at least a portion of a BFLP0169 gene into which a deletion, addition or substitution has been introduced to thereby alter, e.g., functionally disrupt, the BFLP0169 gene. The BFLP0169 gene can be a human gene (e.g., the DNA of SEQ ID NO:1), but more preferably, is a non-human homologue of a human BFLP0169 gene. For example, a mouse homologue of human BFLP0169 gene of SEQ ID NO:1 can be used to construct a homologous recombination vector suitable for altering an endogenous BFLP0169 gene in the mouse genome. In one embodiment, the vector is designed such that, upon homologous recombination, the endogenous BFLP0169 gene is functionally disrupted (i.e., no longer encodes a functional protein; also referred to as a "knock out" vector).

Alternatively, the vector can be designed such that, upon homologous recombination, the endogenous BFLP0169 gene is mutated or otherwise altered but still encodes functional protein (e.g., the upstream regulatory region can be altered to thereby alter the expression of the endogenous BFLP0169 protein). In the homologous recombination vector, the altered portion of the BFLP0169 gene is flanked at its 5'- and 3'-termini by additional nucleic acid of the BFLP0169 gene to allow for homologous recombination to occur between the exogenous BFLP0169 gene carried by the vector and an endogenous BFLP0169 gene in an embryonic stem cell. The additional flanking BFLP0169 nucleic acid is of sufficient length for successful homologous recombination with the endogenous gene. Typically, several kilobases of flanking DNA (both at the 5'- and 3'-termini) are included in the vector. The vector is then introduced into an embryonic stem cell line (e.g., by electroporation) and cells in which the introduced BFLP0169 gene has homologously-recombined with the endogenous BFLP0169 gene are selected.

The selected cells are then injected into a blastocyst of an animal (e.g., a mouse) to form aggregation chimeras. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system. Another example of a recombinase system is the FLP recombinase system of Saccharomyces cerevisiae. If a cre/loxP recombinase system is used to regulate expression of the transgene, animals containing transgenes encoding both the Cre recombinase and a selected protein are required. Such animals can-be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in the art. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Methods of Detecting BFLP0169 Nucleic Acids and Diagnosing Lupus Nephritis

Reagents that detect BFLP0169 nucleic acids and/or polypeptides can be used to detect levels of BFLP0169 RNA and/or proteins sequences in a sample. Because elevated levels of BFLP0169 RNA are found in animals with lupus nephritis, detection of enhanced levels of BFLP0169 RNA and/or BFLP0169 polypeptides indicates the presence or predisposition to lupus in the subject. In addition, lowered levels of BFLP0169 RNA in treated lupus subjects as compared to untreated lupus indicates a return to a non-lupus state. Thus, the efficacy of lupus treatment can be monitored by comparing BFLP0169 RNA or protein levels in a sample from a treated population to samples in a diseased but untreated sample, (or a sample from an individual that has been treated for a shorter period of time).

Levels of BFLP0169 RNA can be assessed by comparing levels in a test cell population, from a subject whose lupus status is unknown, to levels in a reference cell population whose lupus status is known. Thus, the test cell population will typically include at least one cell that is capable of expressing a BFLP0169 gene. By "capable of expressing" is meant that the gene is present in an intact form in the cell and can be expressed. Expression of the BFLP0169 sequence is then detected, if present, and, preferably, measured using methods known in the art. For example, the BFLP0169 sequences disclosed herein can be used to construct probes for detecting BFLP0169 RNA sequences in, e.g., northern blot hybridization analyses or methods which specifically, and, preferably, quantitatively amplify BFLP0169 specific nucleic acid sequences. Alternatively, the sequences can be used to construct primers for specifically amplifying the BFLP0169 sequences in, e.g., amplification-based detection methods such as reverse-transcription based polymerase chain reaction.

BFLP0169 expression can be also measured at the protein level, i.e., by measuring the levels of BFLP0169 polypeptides. Such methods are well known in the art and include, e.g., immunoassays based on antibodies to proteins encoded by the genes.

Expression of sequences in test and control populations of cells can be compared using any art-recognized method for comparing expression of nucleic acid sequences. Whether or not comparison of the gene expression profile in the test cell population to the reference cell population reveals the presence, or degree, of the measured parameter depends on the composition of the reference cell population. For example, if the reference cell population is composed of cells from a lupus free subject, a similar gene expression level in the test cell population and a reference cell population indicates the test cell population is from a lupus free subject. Conversely, if the reference cell population is made up of cells from a diseased subject, a similar gene expression profile between the test cell population and the reference cell population indicates the test cell population is from a subject with lupus.

In various embodiments, a BFLP0169 sequence in a test cell population is considered comparable in expression level to the expression level of the ADIPO sequence in the reference cell population if its expression level varies within a factor of 2.0, 1.5, or 1.0 fold to the level of the BFLP0169 transcript in the reference cell population. In various embodiments, a BFLP0169 sequence in a test cell population can be considered altered in levels of expression if its expression level varies from the reference cell population by more than 1.0, 1.5, 2.0 or more fold from the expression level of the corresponding BFLP0169 sequence in the reference cell population.

If desired, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations. Suitable control nucleic acids can readily be determined by one of ordinary skill in the art.

In some embodiments, the test cell population is compared to multiple reference cell populations. Each of the multiple reference populations may differ in the known parameter. Thus, a test cell population may be compared to a first reference cell population from a subject known to have lupus, as well as a second reference population known to not have lupus.

The test cell population that is exposed can be any number of cells, i e., one or more cells, and can be provided in vitro, in vivo, or ex vivo.

Preferably, cells in the reference cell population are derived from a tissue type as similar as possible to test cell, e.g., renal tissue. In some embodiments, the control cell is derived from the same subject as the test cell. In other embodiments, the reference cell population is derived from a plurality of cells from multiple subjects. For example, the reference cell population can be a database of expression patterns from previously tested cells.

The subject is preferably a mammal. The mammal can be, e.g., a human, non-human primate, mouse, rat, dog, cat, horse, or cow.

Pharmaceutical Compositions

The BFLP0169 nucleic acid molecules, BFLP0169 proteins, and anti-BFLP0169 antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration.

Pharmaceutical compositions suitable for injectable use include sterile aqueous solutions (where water soluble) or dispersions and sterile powders for the extemporaneous preparation of sterile injectable solutions or dispersion.

Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Screening and Detection Methods

The isolated nucleic acid molecules of the invention can be used to express BFLP0169 protein (e.g., via a recombinant expression vector in a host cell in gene therapy applications), to detect BFLP0169 mRNA (e.g., in a biological sample) or a genetic lesion in a BFLP0169 gene, and to modulate BFLP0169 activity, as described further, below. In addition, the BFLP0169 proteins can be used to screen drugs or compounds that modulate the BFLP0169 protein activity or expression as well as to treat disorders characterized by insufficient or excessive production of BFLP0169 protein or production of BFLP0169 protein forms that have decreased or aberrant activity compared to BFLP0169 wild-type protein. In addition, the anti-BFLP0169 antibodies of the invention can be used to detect and isolate BFLP0169 proteins and modulate BFLP0169 activity. For example, BFLP0169 activity includes T-cell or NK cell growth and differentiation, antibody production, and tumor growth.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to BFLP0169 proteins or have a stimulatory or inhibitory effect on, e.g., BFLP0169 protein expression or BFLP0169 protein activity. The invention also includes compounds identified in the screening assays described herein.

In one embodiment, the screening assays are used to identify therapeutic agents for treating autoimmune diseases. The autoimmune disease can be, e.g., lupus, including lupus nephtitis.

In one embodiment, the invention provides assays for screening candidate or test compounds which bind to or modulate the activity of the membrane-bound form of a BFLP0169 protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds.

A "small molecule" as used herein, is meant to refer to a composition that has a molecular weight of less than about 5 kD and most preferably less than about 4 kD. Small molecules can be, e.g., rapamycin, nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. The libraries of compounds may be presented in solution, or on beads, on chips, bacteria, spores, plasmids or on phage In one embodiment, an assay is a cell-based assay in which a cell which expresses a membrane-bound form of BFLP0169 protein, or a biologically-active portion thereof, on the cell surface is contacted with a test compound and the ability of the test compound to bind to a BFLP0169 protein determined. The cell, for example, can be of mammalian origin or a yeast cell. Determining the ability of the test compound to bind to the BFLP0169 protein can be accomplished, for example, by coupling the test compound with a radioisotope or enzymatic label such that binding of the test compound to the BFLP0169 protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of BFLP0169 protein, or a biologically-active portion thereof, on the cell surface with a known compound which binds BFLP0169 to form an assay mixture, contacting the assay mixture with a test compound, and determining the ability of the test compound to interact with a BFLP0169 protein, wherein determining the ability of the test compound to interact with a BFLP0169 protein comprises determining the ability of the test compound to preferentially bind to BFLP0169 or a biologically-active portion thereof as compared to the known compound.

In another embodiment, an assay is a cell-based assay comprising contacting a cell expressing a membrane-bound form of BFLP0169 protein, or a biologically-active portion thereof, on the cell surface with a test compound and determining the ability of the test compound to modulate (e.g., stimulate or inhibit) the activity of the BFLP0169 protein or biologically-active portion thereof. Determining the ability of the test compound to modulate the activity of BFLP0169 or a biologically-active portion thereof can be accomplished, for example, by determining the ability of the BFLP0169 protein to bind to or interact with a BFLP0169 target molecule. As used herein, a "target molecule" is a molecule with which a BFLP0169 protein binds or interacts in nature, for example, a molecule on the surface of a cell which expresses a BFLP0169 interacting protein, a molecule on the surface of a second cell, a molecule in the extracellular milieu, a molecule associated with the internal surface of a cell membrane or a cytoplasmic molecule. A BFLP0169 target molecule can be a non-BFLP0169 molecule or a BFLP0169 protein or polypeptide of the invention In one embodiment, a BFLP0169 target molecule is a component of a signal transduction pathway that facilitates transduction of an extracellular signal (e.g. a signal generated by binding of a compound to a membrane-bound BFLP0169 molecule) through the cell membrane and into the cell. The target, for example, can be a second intercellular protein that has catalytic activity or a protein that facilitates the association of downstream signaling molecules with BFLP0169.

Determining the ability of the BFLP0169 protein to bind to or interact with a BFLP0169 target molecule can be accomplished by one of the methods described above for determining direct binding. In one embodiment, determining the ability of the BFLP0169 protein to bind to or interact with a BFLP0169 target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a BFLP0169-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a BFLP0169 protein or biologically-active portion thereof with a test compound and determining the ability of the test compound to bind to the BFLP0169 protein or biologically-active portion thereof. Binding of the test compound to the BFLP0169 protein can be determined either directly or indirectly as described above. In one such embodiment, the assay comprises contacting the BFLP0169 protein or biologically-active portion thereof with a known compound which binds BFLP0169 to form an assay mixture, contacting the assay mixture with a test compound, and determining the ability of the test compound to interact with a BFLP0169 protein, wherein determining the ability of the test compound to interact with a BFLP0169 protein comprises determining the ability of the test compound to preferentially bind to BFLP0169 or a biologically-active portion thereof as compared to the known compound.

In still another embodiment, an assay is a cell-free assay comprising contacting BFLP0169 protein or a biologically-active portion thereof with a test compound and determining the ability of the test compound to modulate (e.g. stimulate or inhibit) the activity of the BFLP0169 protein or a biologically-active portion thereof. Determining the ability of the test compound to modulate the activity of BFLP0169 can be accomplished, for example, by determining the ability of the BFLP0169 protein to bind to a BFLP0169 target molecule by one of the methods described above for determining direct binding. In an alternative embodiment, determining the ability of the test compound to modulate the activity of BFLP0169 protein can be accomplished by determining the ability of the BFLP0169 protein further modulate a BFLP0169 target molecule. For example, the catalytic/enzymatic activity of the target molecule on an appropriate substrate can be determined as described above.

In yet another embodiment, the cell-free assay comprises contacting the BFLP0169 protein or a biologically-active portion thereof with a known compound which binds BFLP0169 protein to form an assay mixture, contacting the assay mixture with a test compound, and determining the ability of the test compound to interact with a BFLP0169 protein, wherein determining the ability of the test compound to interact with a BFLP0169 protein comprises determining the ability of the BFLP0169 protein to preferentially bind to or modulate the activity of a BFLP0169 target molecule.

The cell-free assays of the invention are amenable for use with both the soluble form or the membrane-bound form of BFLP0169 protein. In the case of cell-free assays comprising the membrane-bound form of BFLP0169 protein, it may be desirable to utilize a solubilizing agent such that the membrane-bound form of BFLP0169 protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl--N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either BFLP0169 protein or its target molecule to facilitate separation of complexed from uncomplexed forms of one or both of the proteins, as well as to accommodate automation of the assay. Binding of a test compound to BFLP0169 protein, or interaction of BFLP0169 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-BFLP0169 fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or BFLP0169 protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of BFLP0169 protein binding or activity determined using standard techniques.

Other techniques for immobilizing proteins on matrices can also be used in the screening assays of the invention. For example, either the BFLP0169 protein or its target molecule can be immobilized utilizing conjugation of biotin and streptavidin. Biotinylated BFLP0169 protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with BFLP0169 protein or target molecules, but which do not interfere with binding of the BFLP0169 protein to its target molecule, can be derivatized to the wells of the plate, and unbound target or BFLP0169 protein trapped in the wells by antibody conjugation. Methods for detecting such complexes, in addition to those described above for the GST-immobilized complexes, include immunodetection of complexes using antibodies reactive with the BFLP0169 protein or target molecule, as well as enzyme-linked assays that rely on detecting an enzymatic activity associated with the BFLP0169 protein or target molecule.

In another embodiment, modulators of BFLP0169 protein expression are identified in a method wherein a cell is contacted with a candidate compound and the expression of BFLP0169 mRNA or protein in the cell is determined. The level of expression of BFLP0169 mRNA or protein in the presence of the candidate compound is compared to the level of expression of BFLP0169 mRNA or protein in the absence of the candidate compound. The candidate compound can then be identified as a modulator of BFLP0169 mRNA or protein expression based upon this comparison. For example, when expression of BFLP0169 mRNA or protein is greater (i.e., statistically significantly greater) in the presence of the candidate compound than in its absence, the candidate compound is identified as a stimulator of BFLP0169 mRNA or protein expression. Alternatively, when expression of BFLP0169 mRNA or protein is less (statistically significantly less) in the presence of the candidate compound than in its absence, the candidate compound is identified as an inhibitor of BFLP0169 mRNA or protein expression. The level of BFLP0169 mRNA or protein expression in the cells can be determined by methods described herein for detecting BFLP0169 mRNA or protein.

In yet another aspect of the invention, the BFLP0169 proteins can be used as "bait proteins" in a two-hybrid assay or three hybrid assay, to identify other proteins that bind to or interact with BFLP0169 ("BFLP0169-binding proteins" or "BFLP0169-bp") and modulate BFLP0169 activity. Such BFLP0169-binding proteins are also likely to be involved in the propagation of signals by the BFLP0169 proteins as, for example, upstream or downstream elements of the BFLP0169 pathway.

The two-hybrid system is based on the modular nature of most transcription factors, which consist of separable DNA-binding and activation domains. Briefly, the assay utilizes two different DNA constructs. In one construct, the gene that codes for BFLP0169 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a BFLP0169-dependenht complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with BFLP0169.

The invention further pertains to novel agents identified by the aforementioned screening assays and uses thereof for treatments as described herein.

The invention will be illustrated in the following non-limiting examples.

EXAMPLE 1

Expression Patterns of Murine BFLP0169 Sequence in Disease-free, Lupus Nephritis Simulated Disease, and Rapamycin-treated Diseased Mice The expression of murine BFLP0169 sequences were examined in mice that developed lupus nephritis-like symptoms in the art-recognized NZB X NZW murine model (see, e.g., Drake et al., Genetic analysis of the NZB contribution to lupus-like autoimmune disease in (NZB×NZW)F1 mice, Proc Natl Acad Sci USA 91:4062-66, 1994; Finck et al., Interleukin 6 promotes murine lupus in NZB/NZWF1 mice, J. Clin. Invest 94:585-91, 1994; Guglielmotti et al., Bindarit prolongs survival and reduces renal damage of NSB/W lupus mice. Clin. Exp. Rheumatol. 16:149, 1998; Yang et al., Dietary conjugated linoleic acid protects against end stage disease of systemic lupus erythematosus in the NZB/W F1 mouse, Immunopharmacol. Immunotoxicol. 22:433-49, 2000. Expression in diseased mice was compared to expression of the sequences in non-diseased mice of varying ages, and in mice whose lupus nephritis-like symptoms diminished following treatment with rapamycin or anti-B7 antibodies.

Mice were obtained from Jackson Laboratories at 6 to 8 weeks of age and aged on site. Data were obtained from kidneys of mice and harvested at the indicated time point: C57BL/6 female mice at 8, and 32 weeks, FI(NZB×NZW) female mice 12, 25, and 42 weeks, mice treated with rapamycin at 42 and 55 weeks, mice treated with antibodies to B7.1 and B7.2 at 52 weeks. Each group contained three mice.

Rapamycin treated mice received 5 mg/kg rapamycin subcutaneous injection 3 times per week for 8 weeks staring at 29 weeks of age. Control mice received injections of vehicle (methyl cellulose) on the same schedule. Effectiveness of therapy was determined by normalization of proteinuria and kidney histology (data not shown). Gene expression analysis was preformed on mice sacrificed at the end of the treatment course (36 weeks of age, data not shown), and at 42 weeks (6 weeks after treatment) and 55 weeks (20 weeks after treatment).

Mice treated with anti-B7 received 200 µg of anti-B7.1 (1G10F9 monoclonal) and 200 µg of anti-B7.2 (GL1 monoclonal) by intra-peritoneal injections 3 times per week for two weeks starting at 29 weeks of age. Gene expression analysis was performed 21 weeks after treatment.

RNA Isolation and Hybridization to Oligonucleotide Arrays

Kidneys from both male and female mice were collected and snap frozen for RNA isolation. One half each kidney was used. A longitudinal section of the left kidney and a cross section of the right kidney was used in for each individual animal.

Snap frozen mouse kidney tissue was homogenized using homogenizer suspended in RLT buffer plus 2ME for 30 to 45 seconds. Total RNA was prepared using the Qiagen Midi Kit following the manufacturer's protocol. RNA was suspended in DEPC treated H2O and quantified by OD 280.

cDNA was synthesized from 5 ug of total RNA using the Superscript Kit (BRL). cDNA was purified using phenol:cloroform:isoamyl alcohol (25:24:1) with a Phage lock gel tube following the Phage lock protocol. Supernatant was collected and cleaned up using EtOH. Sample was resuspended in DEPC treated H2O.

In vitro T7 polymerase driven transcription reactions for synthesis and biotin labeling of antisense cRNA. Qiagen RNeasy spin column purification used used to purify the cRNA. GeneChip hybridization mixtures contained 15 ug fragmented cRNA, 0.5 mg/ml acetylated BSA, 0.1 mg/ml herring sperm DNA, in 1×MES buffer in a total volume of 200 ul as per manufactures instructions. Reaction mixtures were hybridized for 16 hr at 45° C. to Affymetrix Mu11KsubA and Mu11KsubB oligonucleotide arrays. The hybridization mixtures were removed and the arrays were washed and stained with Streptavidin R-phycoerthrin (Molecular Probes) using GeneChip Fluidics Station 400 and scanned with a Hewlett Packard GeneArray Scanner following manufactures instructions. Fluorescent data was collected and converted to gene specific difference average using MicroArray Suite software.

Analysis of Oligonucleotide Array Data

An eleven member standard curve, comprised of gene fragments derived from cloned bacterial and bacteriophage sequences were spiked into each hybridization mixture at concentrations ranging from 0.5 pM to 150 pM representing RNA frequencies of approximately 3.3 to 1000 parts per million (ppm). The biotinylated standard curve fragments were synthesized by T7-polymerase driven IVT reactions from plasmid-based templates. The spiked biotinylated RNA fragments serve both as an internal standard to assess chip sensitivity and as standard curve to convert measured fluorescent difference averages from individual genes into RNA frequencies in ppm as described by Hill et al.

Gene expression frequencies from each individual mouse kidney were measured and the expression data subjected to statistical analysis. Frequency values determined from individual measurements for a given group of mice were averaged. Genes whose frequencies differed significantly between C57B16 kidneys at 12 and 32 weeks of age were classified as changing as a result of the normal aging process, and not due to a disease process.

Expression frequencies in young (disease-free), old (diseased), and effectively treated old (disease-free) F1(NZB×NZW) mice and C57BL6 control mice of oligonucleotide sequence identified on the Affymetrix Murine 11K chip by the qualifier aa002653_s_at are shown. This sequence represents an unknown mouse gene.

The results are shown in FIG. 1. Shown is a histogram showing gene expression levels in kidneys from the indicated mice. Expression levels of BFLP0169 do not vary significantly between C57BL/6 kidneys at 12 weeks of age and kidney at 32 weeks of age, indicating that expression levels do not increase with age in kidneys of non-diseased mice. In (NXB×NZW)F1 kidneys, the gene is expressed at normal levels prior to disease onset (12 weeks of age). As the mice age and disease progresses, increasing expression levels are observed at 25 weeks, 36 weeks (data not shown for 36 weeks), and 42 weeks. By 55 weeks of age, the mice have died due to kidney failure. Mice treated with rapamycin for 8 weeks with treatment starting at 29 weeks of age, remain healthy past 55 weeks of age. Kidneys of mice that have received effective therapy (either rapamycin therapy or anti-B7 therapy) express normal levels of BFLP0169, and these normal levels persist in asymptomatic kidney 20 weeks after cessation of rapamycin therapy and 15 weeks after cessation of anti-B7 therapy. The observation that expression levels return to normal when kidney function is normal indicates that elevated levels are related to, and diagnostic of, disease progression. Blocking the function of these genes may inhibit or retard disease progression. Expression levels may also to used to assess and compare effectiveness of various therapeutic interventions.

EXAMPLE 2

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the L at position 78 of the BFLP0169 sequence shown in Table 2 has been replaced by a V, which is shown in bold font.

```
                                              (SEQ ID NO:3)
MIRKSKITSVLSFCRSSRELWTILLGRSALRELSQIEAELNKHWRRLLEG
LSYYKPPSPSSAEKVKANKDVASPLKEVGLRISKFLGLDEEQSVQLLQCY
LQEDYRGTRDSVKTVLQDERQSQALILKIADYYYEERTCILRCVLHLLTY
FQDERHPYRVEYADCVDKLEKELVSKYRQQFEELYKTEAPTWETHGNLMT
ERQVSRWFVQCLREQSMLLEIIFLYYAYFEMAPSDLLVLTKMFKEQGFGS
RQTNRHLVDETMDPFVDRIGYFSALILVEGMDIESLHKCALDDRRELHQF
AQDGLICQDMDCLMLTFGDIPHHAPVLLAWALLRHTLNPEETSSVVRKIG
GTAIQLNVFQYLTRLLQSLASGGNDCTTSTACMCVYGLLSFVLTSLELHT
LGNQQDIIDTACEVLADPSLPELFWGTEPTSGLGIILDSVCGMFPHLLSP
LLQLLRALVSGKSTAKKVYSFLDKMSFYNELYKHKPHDVISHEDGTLWRR
QTPKLLYPLGGQTNLRIPQGTVGQVMLDDRAYLVRWEYSYSSWTLFTCEI
EMLLHVVSTADVIQHCQRVKPIIDLVHKVISTDLSIADCLLPITSRIYML
LQRLTTVISPPVDVIASCVNCLTVLAARNPAKVWTDLRHTGFLPFVAHPV
SSLSQMISAEGMNAGGYGNLLMNSEQPQGEYGVTIAFLRLITTLVKGQLG
STQSQGLVPCVMFVLKEMLPSYHKWRYNSHGVREQIGCLILELIHAILNL
CHETDLHSSHTPSLQFLCICSLAYTEAGQTVINIMGIGVDTIDMVMAAQP
RSDGAEGQGQGQLLIKTVKLAFSVTNNVIRLKPPSNVVSPLEQALSQHGA
HGNNLIAVLAKYIYHKHDPALPRLAIQLLKRLATVAPMSVYACLGNDAAA
IRDAFLTRLQSKIEDMRIKVMILEFLTVAVETQPGLIELFLNLEVKDGSD
GSKEFSLGMWSCLHAVLELIDSQQQDRYWCPPLLHRAAIAFLHALWQDRR
DSAMLVLRTKPKFWENLTSPLFGTLSPPSETSEPSILETCALIMKIICLE
IYYVVKGSLDQSLKDTLKKFSIEKRFAYWSGYVKSLAVHVAETEGSSCTS
LLEYQMLVSAWRMLLIIATTHADIMHLTDSVVRRQLFLDVLDGTKALLLV
PASVNCLRLGSMKCTLLLILLRQWKRELGSVDEILGPLTEILEGVLQADQ
QLMEKTKAKVFSAFITVLQMKEMKVSDIPQYSQLVLNVCETLQEEVIALF
DQTRHSLALGSATEDKDSMETDDCSRSRHRDQRDGVCVLGLHLAKELCEV
DEDGDSWLQVTRRLPILPTLLTTLEVSLRMKQNLHFTEATLHLLLTLART
QQGATAVAGAGITQSICLPLLSVYQLSTNGTAQTPSASRKSLDAPSWPGV
YRLSMSLMEQLLKTLRYNFLPEALDFVGVHQERTLQCLNAVRTVQSLACL
EEADHTVGFILQLSNFMKEWHFHLPQLMRDIQVNLGYLCQACTSLLHSRK
MLQHYLQNKNGDGLPSAVAQRVQRPPSAASAAPSSSKQPAADTEASEQQA
LHTVQYGLLKILSKTLAALRHFTPDVCQILLDQSLDLAEYNFLFALSFTT
PTFDSEVAPSFGTLLATVNVALNMLGELDKKKEPLTQAVGLSTQAEGTRT
LKSLLMFTMENCFYLLISQAMRYLRDPAVHPRDKQRMKQELSSELSTLLS
SLSRYFRRGAPSSPATGVLPSPQGKSTSLSKASPESQEPLIQLVQAFVRH
MQR
```

EXAMPLE 3

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the L at position 198 of the BFLP0169 sequence shown in Table 2 has been replaced by an 1, which is shown in bold font.

```
                                              (SEQ ID NO:4)
MIRKSKITSVLSFCRSSRELWTILLGRSALRELSQIEAELNKHWRRLLEG
LSYYKPPSPSSAEKVKANKDVASPLKELGLRISKFLGLDEEQSVQLLQCY
LQEDYRGTRDSVKTVLQDERQSQALILKIADYYYEERTCILRCVLHLLTY
FQDERHPYRVEYADCVDKLEKELVSKYRQQFEELYKTEAPTWETHGNIMT
ERQVSRWFVQCLREQSMLLEIIFLYYAYFEMAPSDLLVLTKMFKEQGFGS
RQTNRHLVDETMDPFVDRIGYFSALILVEGMDIESLHKCALDDRRELHQF
AQDGLICQDMDCLMLTFGDIPHHAPVLLAWALLRHTLNPEETSSVVRKIG
GTAIQLNVFQYLTRLLQSLASGGNDCTTSTACMCVYGLLSFVLTSLELHT
LGNQQDIIDTACEVLADPSLPELFWGTEPTSGLGIILDSVCGMFPHLLSP
LLQLLRALVSGKSTAKKVYSFLDKMSFYNELYKHKPHDVISHEDGTLWRR
QTPKLLYPLGGQTNLRIPQGTVGQVMLDDRAYLVRWEYSYSSWTLFTCEI
EMLLHVVSTADVIQHCQRVKPIIDLVHKVISTDLSIADCLLPITSRIYML
LQRLTTVISPPVDVIASCVNCLTVLAARNPAKVWTDLRHTGFLPFVAHPV
SSLSQMISAEGMNAGGYGNLLMNSEQPQGEYGVTIAFLRLITTLVKGQLG
STQSQGLVPCVMFVLKEMLPSYHKWRYNSHGVREQIGCLILELIHAILNL
CHETDLHSSHTPSLQFLCICSLAYTEAGQTVINIMGIGVDTIDMVMAAQP
RSDGAEGQGQGQLLIKTVKLAFSVTNNVIRLKPPSNVVSPLEQALSQHGA
HGNNLIAVLAKYIYHKHDPALPRLAIQLLKRLATVAPMSVYACLGNDAAA
IRDAFLTRLQSKIEDMRIKVMILEFLTVAVETQPGLIELFLNLEVKDGSD
GSKEFSLGMWSCLHAVLELIDSQQQDRYWCPPLLHRAAIAFLHALWQDRR
DSAMLVLRTKPKFWENLTSPLFGTLSPPSETSEPSILETCALIMKIICLE
IYYVVKGSLDQSLKDTLKKFSIEKRFAYWSGYVKSLAVHVAETEGSSCTS
LLEYQMLVSAWRMLLIIATTHADIMHLTDSVVRRQLFLDVLDGTKALLLV
PASVNCLRLGSMKCTLLLILLRQWKRELGSVDEILGPLTEILEGVLQADQ
QLMEKTKAKVFSAFITVLQMKEMKVSDIPQYSQLVLNVCETLQEEVIALF
DQTRHSLALGSATEDKDSMETDDCSRSRHRDQRDGVCVLGLHLAKELCEV
```

-continued

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 4

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the R at position 267 of the BFLP0169 sequence shown in Table 2 has been replaced by a K, which is shown in bold font.

(SEQ ID NO:5)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDKIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

-continued

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 5

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the Q at position 355 of the BFLP0169 sequence shown in Table 2 has been replaced by an N, which is shown in bold font.

(SEQ ID NO:6)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAINLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

-continued
HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 6

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the H at position 446 of the BFLP0169 sequence shown in Table 2 has been replaced by an R, which is shown in bold font.

(SEQ ID NO:7)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPRLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

-continued
SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 7

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the L at position 553 of the BFLP0169 sequence shown in Table 2 has been replaced by an I, which is shown in bold font.

(SEQ ID NO:8)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

```
LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMILHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR
```

EXAMPLE 8

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the W at position 634 of the BFLP0169 sequence shown in Table 2 has been replaced by a F, which is shown in bold font.

```
                                          (SEQ ID NO:9)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVFTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR
```

EXAMPLE 9

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the N at position 749 of the BFLP0169 sequence shown in Table 2 has been replaced by a D, which is shown in bold font.

(SEQ ID NO:10)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILDL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 10

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the V at position 838 of the BFLP0169 sequence shown in Table 2 has been replaced by a M, which is shown in bold font.

(SEQ ID NO:11)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVMSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

```
-continued
LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR
```

EXAMPLE 11

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the G at position 958 of the BFLP0169 sequence shown in Table 2 has been replaced by a T, which is shown in bold font.

```
                                              (SEQ ID NO:12)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLTMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL
```

```
-continued
EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR
```

EXAMPLE 12

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the K at position 1084 of the BFLP0169 sequence shown in Table 2 has been replaced by a R, which is shown in bold font.

```
                                              (SEQ ID NO:13)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVRSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ
```

-continued

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 13

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the A at position 1152 of the BFLP0169 sequence shown in Table 2 has been replaced by a S, which is shown in bold font.

(SEQ ID NO:14)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQQSGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

-continued

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PSSVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 14

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the I at position 1247 of the BFLP0169 sequence shown in Table 2 has been replaced by a V, which is shown in bold font.

(SEQ ID NO:15)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQQSGLVPCVMFVLKEMLPSYHKWRYNSHGVREQIGCLILELIHAILNL

```
CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVVALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR
```

EXAMPLE 15

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the K at position 1331 of the BFLP0169 sequence shown in Table 2 has been replaced by a R, which is shown in bold font.

```
                                              (SEQ ID NO:16)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI
```

```
                                               -continued
EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMRQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR
```

EXAMPLE 16

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the C at position 1449 of the BFLP0169 sequence shown in Table 2 has been replaced by a Y, which is shown in bold font.

```
                                              (SEQ ID NO:17)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF
```

-continued

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PASVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLAYL

EEADHTVGFILQLSNFMKEWHFHLPQLMRDIQVNLGYLCQACTSLLHSRK

MLQHYLQNKNGDGLPSAVAQRVQRPPSAASAAPSSSKQPAADTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 17

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the D at position 1542 of the BFLP0169 sequence shown in Table 2 has been replaced by a Q, which is shown in bold font.

(SEQ ID NO:18)
MIRKSKITSVLSFCRSSRELWTILLGRSALRELSQIEAELNKHWRRLLEG

LSYYKPPSPSSAEKVKANKDVASPLKELGLRISKFLGLDEEQSVQLLQCY

LQEDYRGTRDSVKTVLQDERQSQALILKIADYYYEERTCILRCVLHLLTY

FQDERHPYRVEYADCVDKLEKELVSKYRQQFEELYKTEAPTWETHGNLMT

ERQVSRWFVQCLREQSMLLEIIFLYYAYFEMAPSDLLVLTKMFKEQGFGS

RQTNRHLVDETMDPFVDRIGYFSALILVEGMDIESLHKCALDDRRELHQF

AQDGLICQDMDCLMLTFGDIPHHAPVLLAWALLRHTLNPEETSSVVRKIG

GTAIQLNVFQYLTRLLQSLASGGNDCTTSTACMCVYGLLSFVLTSLELHT

LGNQQDIIDTACEVLADPSLPELFWGTEPTSGLGIILDSVCGMFPHLLSP

LLQLLRALVSGKSTAKKVYSFLDKMSFYNELYKHKPHDVISHEDGTLWRR

QTPKLLYPLGGQTNLRIPQGTVGQVMLDDRAYLVRWEYSYSSWTLFTCEI

EMLLHVVSTADVIQHCQRVKPIIDLVHKVISTDLSIADCLLPITSRIYML

LQRLTTVISPPVDVIASCVNCLTVLAARNPAKVWTDLRHTGFLPFVAHPV

SSLSQMISAEGMNAGGYGNLLMNSEQPQGEYGVTIAFLRLITTLVKGQLG

STQSQGLVPCVMFVLKEMLPSYHKWRYNSHGVREQIGCLILELIHAILNL

CHETDLHSSHTPSLQFLCICSLAYTEAGQTVINIMGIGVDTIDMVMAAQP

RSDGAEGQGQGQLLIKTVKLAFSVTNNVIRLKPPSNVVSPLEQALSQHGA

HGNNLIAVLAKYIYHKHDPALPRLAIQLLKRLATVAPMSVYACLGNDAAA

IRDAFLTRLQSKIEDMRIKVMILEFLTVAVETQPGLIELFLNLEVKDGSD

GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE

IYYVVKGSLDQSLKDTLKKFSIEKRFAYWSGYVKSLAVHVAETEGSSCTS

LLEYQMLVSAWRMLLIIATTHADIMHLTDSVVRRQLFLDVLDGTKALLLV

PSSVNCLRLGSMKCTLLLILLRQWKRELGSVDEILGPLTEILEGVLQADQ

QLMEKTKAKVFSAFITVLQMKEMKVSDIPQYSQLVLNVCETLQEEVIALF

DQTRHSLALGSATEDKDSMETDDCSRSRHRDQRDGVCVLGLHLAKELCEV

DEDGDSWLQVTRRLPILPTLLTTLEVSLRMKQNLHFTEATLHLLLTLART

QQGATAVAGAGITQSICLPLLSVYQLSTNGTAQTPSASRKSLDAPSWPGV

YRLSMSLMEQLLKTLRYNFLPEALDFVGVHQERTLQCLNAVRTVQSLACL

EEADHTVGFILQLSNFMKEWHFHLPQLMRDIQVNLGYLCQACTSLLHSRK

MLQHYLQNKNGDGLPSAVAQRVQRPPSAASAAPSSSKQPAAQTEASEQQA

LHTVQYGLLKILSKTLAALRHFTPDVCQILLDQSLDLAEYNFLFALSFTT

PTFDSEVAPSFGTLLATVNVALNMLGELDKKKEPLTQAVGLSTQAEGTRT

LKSLLMFTMENCFYLLISQAMRYLRDPAVHPRDKQRMKQELSSELSTLLS

SLSRYFRRGAPSSPATGVLPSPQGKSTSLSKASPESQEPLIQLVQAFVRH

MQR

EXAMPLE 18

A Variant of the Human BFLP0169 Polypeptide Sequence Shown in Table 2

A polypeptide sequence varying by one amino acid from the BFLP0169 amino acid sequence presented in Table 2 is shown below. For the sequence shown, the F at position 1706 of the BFLP0169 sequence shown in Table 2 has been replaced by a H, which is shown in bold font.

(SEQ ID NO:18)
MIRKSKITSVLSFCRSSRELWTILLGRSALRELSQIEAELNKHWRRLLEG
LSYYKPPSPSSAEKVKANKDVASPLKELGLRISKFLGLDEEQSVQLLQCY
LQEDYRGTRDSVKTVLQDERQSQALILKIADYYYEERTCILRCVLHLLTY
FQDERHPYRVEYADCVDKLEKELVSKYRQQFEELYKTEAPTWETHGNLMT
ERQVSRWFVQCLREQSMLLEIIFLYYAYFEMAPSDLLVLTKMFKEQGFGS
RQTNRHLVDETMDPFVDRIGYFSALILVEGMDIESLHKCALDDRRELHQF
AQDGLICQDMDCLMLTFGDIPHHAPVLLAWALLRHTLNPEETSSVVRKIG
GTAIQLNVFQYLTRLLQSLASGGNDCTTSTACMCVYGLLSFVLTSLELHT
LGNQQDIIDTACEVLADPSLPELFWGTEPTSGLGIILDSVCGMFPHLLSP
LLQLLRALVSGKSTAKKVYSFLDKMSFYNELYKHKPHDVISHEDGTLWRR
QTPKLLYPLGGQTNLRIPQGTVGQVMLDDRAYLVRWEYSYSSWTLFTCEI
EMLLHVVSTADVIQHCQRVKPIIDLVHKVISTDLSIADCLLPITSRIYML
LQRLTTVISPPVDVIASCVNCLTVLAARNPAKVWTDLRHTGFLPFVAHPV
SSLSQMISAEGMNAGGYGNLLMNSEQPQGEYGVTIAFLRLITTLVKGQLG
STQSQGLVPCVMFVLKEMLPSYHKWRYNSHGVREQIGCLILELIHAILNL
CHETDLHSSHTPSLQFLCICSLAYTEAGQTVINIMGIGVDTIDMVMAAQP
RSDGAEGQGQGQLLIKTVKLAFSVTNNVIRLKPPSNVVSPLEQALSQHGA
HGNNLIAVLAKYIYHKHDPALPRLAIQLLKRLATVAPMSVYACLGNDAAA
IRDAFLTRLQSKIEDMRIKVMILEFLTVAVETQPGLIELFLNLEVKDGSD
GSKEFSLGMWSCLHAVLELIDSQQQDRYWCPPLLHRAAIAFLHALWQDRR

DSAMLVLRTKPKFWENLTSPLFGTLSPPSETSEPSILETCALIMKIICLE
IYYVVKGSLDQSLKDTLKKFSIEKRFAYWSGYVKSLAVHVAETEGSSCTS
LLEYQMLVSAWRMLLIIATTHADIMHLTDSVVRRQLFLDVLDGTKALLLV
PASVNCLRLGSMKCTLLLILLRQWKRELGSVDEILGPLTEILEGVLQADQ
QLMEKTKAKVFSAFITVLQMKEMKVSDIPQYSQLVLNVCETLQEEVIALF
DQTRHSLALGSATEDKDSMETDDCSRSRHRDQRDGVCVLGLHLAKELCEV
DEDGDSWLQVTRRLPILPTLLTTLEVSLRMKQNLHFTEATLHLLLTLART
QQGATAVAGAGITQSICLPLLSVYQLSTNGTAQTPSASRKSLDAPSWPGV
YRLSMSLMEQLLKTLRYNFLPEALDFVGVHQERTLQCLNAVRTVQSLACL
EEADHTVGFILQLSNFMKEWHFHLPQLMRDIQVNLGYLCQACTSLLHSRK
MLQHYLQNKNGDGLPSAVAQRVQRPPSAASAAPSSSKQPAADTEASEQQA
LHTVQYGLLKILSKTLAALRHFTPDVCQILLDQSLDLAEYNFLFALSFTT
PTFDSEVAPSFGTLLATVNVALNMLGELDKKKEPLTQAVGLSTQAEGTRT
LKSLLMFTMENCFYLLISQAMRYLRDPAVHPRDKQRMKQELSSELSTLLS
SLSRYHRRGAPSSPATGVLPSPQGKSTSLSKASPESQEPLIQLVQAFVRH
MQR

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. An isolated nucleic acid molecule encoding a polypeptide comprising the amino acid sequence selected from the group, consisting of SEQ ID NOs:2 through 19.

2. A vector comprising the nucleic acid molecule of claim 1.

3. An isolated cell comprising the vector of claim 2.

4. A method of producing a polypeptide, said method comprising culturing a cell comprising the nucleic acid molecule of claim 1 under conditions allowing for expression of the polypeptide encoded by said nucleic acid molecule.

5. The isolated nucleic acid molecule of claim 1 wherein the nucleic acid molecule encodes the amino acid sequence set forth in SEQ ID NO:2.

6. The isolated nucleic acid molecule of claim 1 wherein the nucleic acid molecule encodes the amino acid sequence set forth in SEQ ID NO:3.

7. The isolated nucleic acid molecule of claim 1 wherein the nucleic acid molecule encodes the amino acid sequence set forth in SEQ ID NO:4.

8. The isolated nucleic acid molecule of claim 1 wherein the nucleic acid molecule encodes the amino acid sequence set forth in SEQ ID NO:5.

9. The isolated nucleic acid molecule of claim 1 wherein the nucleic acid molecule encodes the amino acid sequence set forth in SEQ ID NO:6.

10. The isolated nucleic acid molecule of claim 1 wherein the nucleic acid molecule encodes the amino acid sequence set forth in SEQ ID NO:7.

11. The isolated nucleic acid molecule of claim 1 wherein the nucleic acid molecule encodes the amino acid sequence set forth in SEQ ID NO:8.

12. The isolated nucleic acid molecule of claim 1 wherein the nucleic acid molecule encodes the amino acid sequence set forth in SEQ ID NO:9.

13. The isolated nucleic acid molecule of claim 1 wherein the nucleic acid molecule encodes the amino acid sequence set forth in SEQ ID NO:10.

14. The isolated nucleic acid molecule of claim 1 wherein the nucleic acid molecule encodes the amino acid sequence of SEQ ID NO:11.

15. The isolated nucleic acid molecule of claim 1 wherein the nucleic acid molecule encodes the amino acid sequence set forth in SEQ ID NO:12.

16. The isolated nucleic acid molecule of claim 1 wherein the nucleic acid molecule encodes the amino acid sequence set forth in SEQ ID NO:13.

17. The isolated nucleic acid molecule of claim 1 wherein the nucleic acid molecule encodes the amino acid sequence set forth in SEQ ID NO:14.

18. The isolated nucleic acid molecule of claim 1 wherein the nucleic acid molecule encodes the amino acid sequence set forth in SEQ ID NO:15.

19. The isolated nucleic acid molecule of claim 1 wherein the nucleic acid molecule encodes the amino acid sequence set forth in SEQ ID NO:16.

20. The isolated nucleic acid molecule of claim 1 wherein the nucleic acid molecule encodes the amino acid sequence set forth in SEQ ID NO:17.

21. The isolated nucleic acid molecule of claim 1 wherein the nucleic acid molecule encodes the amino acid sequence set forth in SEQ ID NO:18.

22. The isolated nucleic acid molecule of claim 1 wherein the nucleic acid molecule encodes the amino acid sequence set forth in SEQ ID NO:19.

* * * * *

SEQUENCE LISTING

```
<160> NUMBER OF SEQ ID NOS: 26

<210> SEQ ID NO 1
<211> LENGTH: 5987
<212> TYPE: DNA
<213> ORGANISM: Homo sapiens

<400> SEQUENCE: 1
atgatcagaa agagcaaaat tacctctgtt ctctcatttt gcaggagcag tagagaactg      60
tggactattc tgcttggaag gtcagctctg agagagctga gtcagattga ggcagaactg     120
aataaacatt ggcggcgatt gttagagggg ctttcttact acaaacctcc cagtccaagt     180
tcagctgaaa aagtgaaagc taataaagat gtagcttcac cattgaagga actgggttta     240
agaatcagca gttttttggg tcttgatgaa gaacagagtg tgcagttact ccagtgttac     300
ctgcaagagg actacagggg tactcgggac tcagtaaaga cagtactgca agatgagagg     360
cagagccagg ccttaatcct gaagattgca gattattatt atgaagaaag aacctgtatt     420
cttcgttgtg tcttacacct tctcacttac ttccaagatg aaagacaccc ctatagggtt     480
gaatatgcag actgtgttga taaattggag aaggaactag tttcaaaata cagacagcag     540
ttcgaagagc tttataaaac tgaagcacca acttgggaga cacatggaaa tctcatgaca     600
```

```
gagcgccaag tgtctcgctg gtttgttcag tgccttcggg aacagtccat gctgctagaa    660
attattttcc tttattatgc atactttgag atggcaccca gtgacttact tgtattaacc    720
aagatgttta aagagcaagg atttggtagt aggcagacca ataggcacct ggtggatgag    780
actatggatc cttttgtaga tcggattggc tacttcagtg ccctcatcct ggtggagggc    840
atggatatcg agtccttgca taagtgtgct ttggatgaca aagagaact gcatcagttt     900 gcgcaggatg ggcttatttg tcaggatatg gactgtttaa tgttgacctt ggggacatt     960 ccacatcatg ccccagtgct tttggcctgg gctctcctcc gtcacactct gaacccagaa    1020
gagacaagca gtgtggtccg aagataggt ggcacagcca tccagctgaa tgtgtttcag      1080
tacttgaccc gattgctcca gtcccttgcc agtgggggaa atgattgcac caccagcact    1140
gcatgcatgt gtgtctatgg actgctctct ttcgttctga cctcgttgga gctgcacacc    1200
ctgggcaatc agcaggatat aattgataca gcatgtgaag tattggccga cccttctctt    1260
ccggaactgt tctggggaac agagccaact tctggccttg ggatcattct ggacagtgtg    1320
tgtggaatgt tccccaccct tctctcccca ctcctgcaac tgctccgagc cctggtatca    1380
gggaagtcca cagccaaaaa ggtgtatagc ttcttggata agatgtcttt ctacaatgaa    1440
ctttataaac acaagcctca tgatgtgatc tcccatgaag atggaactct tggcggaga    1500 caaacaccca aactcctta tccccttggg ggtcaaacca accttcgcat acctcaaggc     1560
actgtgggcc aagtaatgtt ggatgatagg gcatacctgg tacgctggga atactcctat    1620
agcagctgga ccctctttac ctgcgagatt gaaatgttgc ttcatgttgt ttcaactgca    1680
gatgtgattc agcactgcca gcgagtcaaa cccatcattg atctcgtcca taggtcatc    1740 agtacagacc tgtcgatagc agactgtctc ctgcccatca catctcgcat ctacatgctg    1800
ctgcagcggt taacgacagt gatctcccca cctgtggatg tcattgcttc ttgtgtcaac    1860
tgcttaactg ttttggctgc ccgcaatcca gcaaaggtct ggactgatct tcgtcacaca    1920 ggtttttta catttgtggc ccatcctgtc tccagcctga gtcagatgat tagtgcggaa     1980
gggatgaatg ctggagggta cggaaaacctc ttgatgaaca gtgaacagcc tcagggcgag   2040
tatggggtta ctattgcctt tctgcgcttg atcaccaccc ttgtcaaggg gcaacttggt    2100
agtacccaga gccaaggact tgtaccctgt gtaatgtttg tgctgaagga gatgcttccc    2160
agctaccata agtggcgcta caactctcat ggagtgaggg aacagattgg ttgcctgatc    2220
ttggagctga ttcatgcgat actgaacctg tgccacgaga cagacctgca cagcagtcat    2280
actcccagcc tgcagtttct ctgcatctgc agcctggcat acacagaagc aggacagaca    2340
gttatcaata tcatgggcat tggcgtggac accattgaca tggtgatggc tgctcagcct    2400
cgaagtgatg gggcagaggg ccaggggcag ggccagctgc tgatcaagac agtgaaactg    2460
gcattctccg tcaccaacaa tgttattcgg ctgaaacctc cttctaatgt ggtgtccccc    2520
ctggaacagg ctctctcaca acatggtgct catggaaaca acctcattgc tgttctagcc    2580
aaatacatct accacaaaca tgaccctgct tgccacgtc ttgccattca gctgctgaaa     2640
cgtctggcca cggtggcccc aatgtcagtg tatgcttgtc tgggcaatga tgcggctgcc    2700
attcgtgatg ccttcctgac ccgattgcag agcaaaattg aggacatgcg catcaaagtc    2760
atgattctag agttcctcac tgttgcagta gagacccagc caggcctcat cgaactgttt    2820
ctgaacctgg aagttaagga tggcagtgat ggctcaaagg aattcagcct tgggatgtgg    2880
agctgtctcc atgcagtgct ggagctgatt gattcccaac agcaagatcg atactggtgc    2940 ccaccccctgc tgcatcgtgc cgccattgcc ttttgcatg ctctgtggca ggatcggagg    3000
```

```
gacagtgcca tgctggtcct ccgaaccaaa cccaagtttt gggaaaattt aaccagtccg   3060
ctgtttggaa ccctttctcc tccctctgaa acatcagagc ccagcatcct ggaaacctgt   3120
gccctaatca tgaagataat ttgcttggag atatactatg tagtaaaggg ttcattagac   3180
cagtcattaa aggatacact gaagaaattt ccatcgaga aacgctttgc ctactggtca    3240
gggtatgtca agtcattggc agttcacgtg gccgaaacag aaggcagcag ctgcacctcc   3300
ttgttagagt accagatgct ggtgtccgcc tggaggatgc ttctcatcat tgccaccact   3360
catgcagata taatgcacct gactgactct gtggtgcgtc gccagctctt tcttgacgtg   3420
cttgatggaa ccaaagcatt actcctagtt ccagcctcag tgaactgcct tcgccttggc   3480
tccatgaagt gcactctgct gcttatcctc ctccggcagt ggaagagaga gttaggttct   3540
gtggatgaaa tccttggacc cttgacggag atcctggagg gagtgctgca ggccgaccag   3600
caactcatgg agaagaccaa ggccaaggtg ttctcagcat tcatcacagt gttgcaaatg   3660
aaggagatga agtaagtga catcccccag tactcccagc tggtgctgaa tgtctgtgag    3720
accctccaag aggaagtgat tgcactcttc gaccagaccc gccacagtct ggcattaggc   3780
agtgccacag aggacaagga cagcatggag actgacgact gttctcggtc ccggcacagg   3840
gaccagcgtg atggggtgtg tgtcctgggc ctgcacctgg ccaaggagct gtgtgaggta   3900
gacgaggatg gtgactcctg gctgcaggta acccgcaggc tccccatcct acccaccctc   3960
ctcaccactc tagaggtgag ccttcgcatg aagcagaacc tgcatttcac tgaggccaca   4020
ttgcatctgc tcctcaccct ggctcgcact cagcagggag ccacagcagt ggctggagct   4080
ggcatcaccc agagcatttg tttgcccctt ctgagtgtgt accagctgag caccaacggc   4140
acagcacaga cacctagtgc ctctcggaag tccctggatg cccctcttg gccaggagtc    4200 taccgcctgt ccatgtccct gatggagcag ctgctcaaaa ctctgcgcta caacttcctg   4260
cctgaggccc tggacttcgt gggtgtccac caggagcgga ccttacagtg cctcaacgca   4320
gtgaggacag tgcagagtct ggcctgcctg gaggaggcgg accacaccgt gggttttatt   4380
ctgcagctct ctaacttcat gaaggagtgg cacttccacc tgcctcagct catgcgtgat   4440
atccaggtca acctgggtta cttgtgccag gcatgtacct ctctcctgca cagtcgaaag   4500
atgctgcagc attacttaca gaacaaaaat ggggatggcc tcccctcagc tgttgcccag   4560
cgagtccaga ggccaccgtc tgctgcttct gctgcccct cctcctcaaa gcagcccgct    4620
gctgacacag aggcatcaga gcagcaggcc ttgcacacag tccagtatgg ccttctcaag   4680
atcctcagca agacgctggc agccctgcgc cacttcaccc cagatgtctg ccagattctg   4740
ctggatcagt ccctggacct tgctgaatac aacttcctgt ttgccctgag ctttaccact   4800
cccacctttg actccgaagt ggccccctcc ttcgggaccc ttctggccac agtgaatgtg   4860
gccctcaaca tgcttggaga gctggacaag aaaaaggagc ccctcaccca ggcagtgggg   4920
ctcagcacac aggcagaagg gaccaggacg ttaaagtccc tcctgatgtt taccatggaa   4980
aactgcttct acctgctcat ctctcaggcg atgcggtacc ttagggaccc ggctgtgcac   5040
ccccgggaca acagcggat gaagcaggag ctcagctctg agttgagcac gctgctgtcc    5100
agcctctcgc gctacttccg ccggggagcc cccagctccc ctgccactgg tgtcctcccc   5160
tcgccgcagg gcaagtccac ctctctctcc aaagccagcc ctgagagtca ggagcctctg   5220
atccagttgg tgcaggcgtt tgtccggcat atgcaaagat agggcagtgc tgttctgccc   5280 acctaccccct ctccaccagc ctacactgca ccctggctgg caggggtgct gctggctgct   5340
```

```
agggcctata caatggaggg cacctcctgt caccccctc ccggagtagc cacgactcca    5400
gccaccaccc actgacgtta tttttatact agatgaagag gtcaacagca ggcatgggga    5460
gccgagtctt ctgtgctcag gtcctcacgc tgcagacgcc ccctagagga actttccttc    5520 cttttccagca ttccccacag cactgccggc caggggagag cggcagccc agcagagggc    5580 tctatgcacg ggtttcaaac ctgttttcca cactctgtct ttgcagtttt ggtaattctg    5640
tggtctattt atacagatat taaaatcttg tttatagaca gctgtgtgat gtttaacttc    5700
aaagcccagg gatgacaacg tggctctcag aacctagaaa actcccctgg ccaggcgcct    5760
gggagtgggg ctgcagcctc ggggaaggc aggtactgat ggatggctag ttcaccagca    5820
tctcctcatt cctgtccttg ggctgagggt ttggctgggt gggcgctgtc agatattccc    5880
ttccttggcc tgcgctggtc ctgtccttga ccctgctttc attggcccag tgggctgagc    5940
tcatccctgg gtgagccttt cttgaagctc tgtgccttcc tatttat              5987
```

<210> SEQ ID NO 2
<211> LENGTH: 1753
<212> TYPE: PRT
<213> ORGANISM: Homo sapiens

<400> SEQUENCE: 2

```
Met Ile Arg Lys Ser Lys Ile Thr Ser Val Leu Ser Phe Cys Arg Ser
 1               5                  10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
```

-continued

```
                260                 265                 270
Ser Ala Leu Ile Leu Val Glu Gly Met Asp Ile Glu Ser Leu His Lys
            275                 280                 285
Cys Ala Leu Asp Asp Arg Arg Glu Leu His Gln Phe Ala Gln Asp Gly
            290                 295                 300
Leu Ile Cys Gln Asp Met Asp Cys Leu Met Leu Thr Phe Gly Asp Ile
305                 310                 315                 320
Pro His His Ala Pro Val Leu Leu Ala Trp Ala Leu Arg His Thr
                    325                 330                 335
Leu Asn Pro Glu Glu Thr Ser Ser Val Val Arg Lys Ile Gly Gly Thr
            340                 345                 350
Ala Ile Gln Leu Asn Val Phe Gln Tyr Leu Thr Arg Leu Leu Gln Ser
            355                 360                 365
Leu Ala Ser Gly Gly Asn Asp Cys Thr Thr Ser Thr Ala Cys Met Cys
            370                 375                 380
Val Tyr Gly Leu Leu Ser Phe Val Leu Thr Ser Leu Glu Leu His Thr
385                 390                 395                 400
Leu Gly Asn Gln Gln Asp Ile Ile Asp Thr Ala Cys Glu Val Leu Ala
            405                 410                 415
Asp Pro Ser Leu Pro Glu Leu Phe Trp Gly Thr Glu Pro Thr Ser Gly
            420                 425                 430
Leu Gly Ile Ile Leu Asp Ser Val Cys Gly Met Phe Pro His Leu Leu
            435                 440                 445
Ser Pro Leu Leu Gln Leu Leu Arg Ala Leu Val Ser Gly Lys Ser Thr
            450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
            485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
            515                 520                 525
Asp Arg Ala Tyr Leu Val Arg Trp Glu Tyr Ser Tyr Ser Ser Trp Thr
            530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
                    565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
            595                 600                 605
Ser Pro Pro Val Asp Val Ile Ala Ser Cys Val Asn Cys Leu Thr Val
            610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                    645                 650                 655
Ile Ser Ala Glu Gly Met Asn Ala Gly Gly Tyr Gly Asn Leu Leu Met
            660                 665                 670
Asn Ser Glu Gln Pro Gln Gly Glu Tyr Gly Val Thr Ile Ala Phe Leu
            675                 680                 685
```

```
Arg Leu Ile Thr Thr Leu Val Lys Gly Gln Leu Gly Ser Thr Gln Ser
    690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
                725                 730                 735
Gly Cys Leu Ile Leu Glu Leu Ile His Ala Ile Leu Asn Leu Cys His
            740                 745                 750
Glu Thr Asp Leu His Ser Ser His Thr Pro Ser Leu Gln Phe Leu Cys
        755                 760                 765
Ile Cys Ser Leu Ala Tyr Thr Glu Ala Gly Gln Thr Val Ile Asn Ile
    770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Gln Leu Leu Ile Lys
                805                 810                 815
Thr Val Lys Leu Ala Phe Ser Val Thr Asn Asn Val Ile Arg Leu Lys
            820                 825                 830
Pro Pro Ser Asn Val Val Ser Pro Leu Glu Gln Ala Leu Ser Gln His
        835                 840                 845
Gly Ala His Gly Asn Asn Leu Ile Ala Val Leu Ala Lys Tyr Ile Tyr
    850                 855                 860
His Lys His Asp Pro Ala Leu Pro Arg Leu Ala Ile Gln Leu Leu Lys
865                 870                 875                 880
Arg Leu Ala Thr Val Ala Pro Met Ser Val Tyr Ala Cys Leu Gly Asn
                885                 890                 895
Asp Ala Ala Ile Arg Asp Ala Phe Leu Thr Arg Leu Gln Ser Lys
            900                 905                 910
Ile Glu Asp Met Arg Ile Lys Val Met Ile Leu Glu Phe Leu Thr Val
        915                 920                 925
Ala Val Glu Thr Gln Pro Gly Leu Ile Glu Leu Phe Leu Asn Leu Glu
    930                 935                 940
Val Lys Asp Gly Ser Asp Gly Ser Lys Glu Phe Ser Leu Gly Met Trp
945                 950                 955                 960
Ser Cys Leu His Ala Val Leu Glu Leu Ile Asp Ser Gln Gln Gln Asp
                965                 970                 975
Arg Tyr Trp Cys Pro Pro Leu Leu His Arg Ala Ala Ile Ala Phe Leu
            980                 985                 990
His Ala Leu Trp Gln Asp Arg Arg Asp Ser Ala Met Leu Val Leu Arg
        995                 1000                1005
Thr Lys Pro Lys Phe Trp Glu Asn Leu Thr Ser Pro Leu Phe Gly Thr
    1010                1015                1020
Leu Ser Pro Pro Ser Glu Thr Ser Glu Pro Ser Ile Leu Glu Thr Cys
1025                1030                1035                1040
Ala Leu Ile Met Lys Ile Ile Cys Leu Glu Ile Tyr Tyr Val Lys
                1045                1050                1055
Gly Ser Leu Asp Gln Ser Leu Lys Asp Thr Leu Lys Lys Phe Ser Ile
            1060                1065                1070
Glu Lys Arg Phe Ala Tyr Trp Ser Gly Tyr Val Lys Ser Leu Ala Val
        1075                1080                1085
His Val Ala Glu Thr Glu Gly Ser Ser Cys Thr Ser Leu Leu Glu Tyr
    1090                1095                1100
```

-continued

```
Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ala
        1140                1145                1150

Ser Val Asn Cys Leu Arg Leu Gly Ser Met Lys Cys Thr Leu Leu Leu
    1155                1160                1165

Ile Leu Leu Arg Gln Trp Lys Arg Glu Leu Gly Ser Val Asp Glu Ile
1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

Val Leu Gln Met Lys Glu Met Lys Val Ser Asp Ile Pro Gln Tyr Ser
        1220                1225                1230

Gln Leu Val Leu Asn Val Cys Glu Thr Leu Gln Glu Glu Val Ile Ala
    1235                1240                1245

Leu Phe Asp Gln Thr Arg His Ser Leu Ala Leu Gly Ser Ala Thr Glu
    1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
        1300                1305                1310

Arg Leu Pro Ile Leu Pro Thr Leu Leu Thr Thr Leu Glu Val Ser Leu
    1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
            1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
    1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
            1445                1450                1455

Val Gly Phe Ile Leu Gln Leu Ser Asn Phe Met Lys Glu Trp His Phe
        1460                1465                1470

His Leu Pro Gln Leu Met Arg Asp Ile Gln Val Asn Leu Gly Tyr Leu
    1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
```

-continued

```
                  1525                1530                1535

Lys Gln Pro Ala Ala Asp Thr Glu Ala Ser Glu Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
        1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
        1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
        1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
        1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
        1715                1720                1725

Leu Ser Lys Ala Ser Pro Glu Ser Gln Glu Pro Leu Ile Gln Leu Val
        1730                1735                1740

Gln Ala Phe Val Arg His Met Gln Arg
1745                1750

<210> SEQ ID NO 3
<211> LENGTH: 1753
<212> TYPE: PRT
<213> ORGANISM: Homo sapiens

<400> SEQUENCE: 3

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Ser Pro Ser Ser Ala Glu Lys
    50                  55                  60

Val Lys Ala Asn Lys Asp Val Ala Ser Pro Leu Lys Glu Val Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Tyr Glu Glu Arg Thr Cys Ile Leu Arg Cys Val
    130                 135                 140
```

-continued

```
Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
    290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
    370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
            420                 425                 430

Leu Gly Ile Ile Leu Asp Ser Val Cys Gly Met Phe Pro His Leu Leu
        435                 440                 445

Ser Pro Leu Leu Gln Leu Leu Arg Ala Leu Val Ser Gly Lys Ser Thr
    450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
            500                 505                 510

Thr Asn Leu Arg Ile Pro Gln Gly Thr Val Gly Gln Val Met Leu Asp
        515                 520                 525

Asp Arg Ala Tyr Leu Val Arg Trp Glu Tyr Ser Tyr Ser Ser Trp Thr
    530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
```

-continued

```
                565                 570                 575
His Lys Val Ile Ser Thr Asp Leu Ser Ile Ala Asp Cys Leu Leu Pro
            580                 585                 590

Ile Thr Ser Arg Ile Tyr Met Leu Leu Gln Arg Leu Thr Thr Val Ile
            595                 600                 605

Ser Pro Pro Val Asp Val Ile Ala Ser Cys Val Asn Cys Leu Thr Val
            610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
            645                 650                 655

Ile Ser Ala Glu Gly Met Asn Ala Gly Gly Tyr Gly Asn Leu Leu Met
            660                 665                 670

Asn Ser Glu Gln Pro Gln Gly Glu Tyr Gly Val Thr Ile Ala Phe Leu
            675                 680                 685

Arg Leu Ile Thr Thr Leu Val Lys Gly Gln Leu Gly Ser Thr Gln Ser
            690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
            725                 730                 735

Gly Cys Leu Ile Leu Glu Leu Ile His Ala Ile Leu Asn Leu Cys His
            740                 745                 750

Glu Thr Asp Leu His Ser Ser Thr Pro Ser Leu Gln Phe Leu Cys
            755                 760                 765

Ile Cys Ser Leu Ala Tyr Thr Glu Ala Gly Gln Thr Val Ile Asn Ile
770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Leu Leu Ile Lys
            805                 810                 815

Thr Val Lys Leu Ala Phe Ser Val Thr Asn Asn Val Ile Arg Leu Lys
            820                 825                 830

Pro Pro Ser Asn Val Val Ser Pro Leu Glu Gln Ala Leu Ser Gln His
            835                 840                 845

Gly Ala His Gly Asn Asn Leu Ile Ala Val Leu Ala Lys Tyr Ile Tyr
            850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
            885                 890                 895

Asp Ala Ala Ile Arg Asp Ala Phe Leu Thr Arg Leu Gln Ser Lys
            900                 905                 910

Ile Glu Asp Met Arg Ile Lys Val Met Ile Leu Glu Phe Leu Thr Val
            915                 920                 925

Ala Val Glu Thr Gln Pro Gly Leu Ile Glu Leu Phe Leu Asn Leu Glu
            930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
            965                 970                 975

Arg Tyr Trp Cys Pro Pro Leu Leu His Arg Ala Ala Ile Ala Phe Leu
            980                 985                 990
```

```
His Ala Leu Trp Gln Asp Arg Arg Asp Ser Ala Met Leu Val Leu Arg
    995                 1000                1005

Thr Lys Pro Lys Phe Trp Glu Asn Leu Thr Ser Pro Leu Phe Gly Thr
   1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
           1045                 1050                1055

Gly Ser Leu Asp Gln Ser Leu Lys Asp Thr Leu Lys Lys Phe Ser Ile
        1060                1065                1070

Glu Lys Arg Phe Ala Tyr Trp Ser Gly Tyr Val Lys Ser Leu Ala Val
       1075                 1080                1085

His Val Ala Glu Thr Glu Gly Ser Ser Cys Thr Ser Leu Leu Glu Tyr
    1090                 1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
           1125                1130                1135

Phe Leu Asp Val Leu Asp Gly Thr Lys Ala Leu Leu Leu Val Pro Ala
        1140                1145                1150

Ser Val Asn Cys Leu Arg Leu Gly Ser Met Lys Cys Thr Leu Leu Leu
    1155                1160                1165

Ile Leu Leu Arg Gln Trp Lys Arg Glu Leu Gly Ser Val Asp Glu Ile
       1170                 1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
           1205                1210                1215

Val Leu Gln Met Lys Glu Met Lys Val Ser Asp Ile Pro Gln Tyr Ser
        1220                1225                1230

Gln Leu Val Leu Asn Val Cys Glu Thr Leu Gln Glu Glu Val Ile Ala
    1235                1240                1245

Leu Phe Asp Gln Thr Arg His Ser Leu Ala Leu Gly Ser Ala Thr Glu
   1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
           1285                1290                1295

Leu Cys Glu Val Asp Glu Asp Gly Asp Ser Trp Leu Gln Val Thr Arg
        1300                1305                1310

Arg Leu Pro Ile Leu Pro Thr Leu Leu Thr Leu Glu Val Ser Leu
    1315                1320                1325

Arg Met Lys Gln Asn Leu His Phe Thr Glu Ala Thr Leu His Leu Leu
   1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
           1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
    1395                1400                1405
```

Glu Gln Leu Leu Lys Thr Leu Arg Tyr Asn Phe Leu Pro Glu Ala Leu
            1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
            1445                1450                1455

Val Gly Phe Ile Leu Gln Leu Ser Asn Phe Met Lys Glu Trp His Phe
        1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Asp Thr Glu Ala Ser Glu Gln Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
    1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 4
<211> LENGTH: 1753
<212> TYPE: PRT
<213> ORGANISM: Homo sapiens

<400> SEQUENCE: 4

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

-continued

```
Leu Ser Gln Ile Glu Ala Glu Leu Asn Lys His Trp Arg Arg Leu Leu
            35                  40                  45

Glu Gly Leu Ser Tyr Tyr Lys Pro Pro Ser Pro Ser Ser Ala Glu Lys
        50                  55                  60

Val Lys Ala Asn Lys Asp Val Ala Ser Pro Leu Lys Glu Leu Gly Leu
 65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Glu Arg Thr Cys Ile Leu Arg Cys Val
130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Ile Met Thr Glu Arg Gln Val Ser Arg Trp Phe
        195                 200                 205

Val Gln Cys Leu Arg Glu Gln Ser Met Leu Leu Glu Ile Ile Phe Leu
210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
            420                 425                 430

Leu Gly Ile Ile Leu Asp Ser Val Cys Gly Met Phe Pro His Leu Leu
        435                 440                 445
```

-continued

```
Ser Pro Leu Leu Gln Leu Leu Arg Ala Leu Val Ser Gly Lys Ser Thr
    450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
                485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
        515                 520                 525
Asp Arg Ala Tyr Leu Val Arg Trp Glu Tyr Ser Tyr Ser Ser Trp Thr
    530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
                565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
        595                 600                 605
Ser Pro Pro Val Asp Val Ile Ala Ser Cys Val Asn Cys Leu Thr Val
    610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                645                 650                 655
Ile Ser Ala Glu Gly Met Asn Ala Gly Gly Tyr Gly Asn Leu Leu Met
            660                 665                 670
Asn Ser Glu Gln Pro Gln Gly Glu Tyr Gly Val Thr Ile Ala Phe Leu
        675                 680                 685
Arg Leu Ile Thr Thr Leu Val Lys Gly Gln Leu Gly Ser Thr Gln Ser
    690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
                725                 730                 735
Gly Cys Leu Ile Leu Glu Leu Ile His Ala Ile Leu Asn Leu Cys His
            740                 745                 750
Glu Thr Asp Leu His Ser Ser His Thr Pro Ser Leu Gln Phe Leu Cys
        755                 760                 765
Ile Cys Ser Leu Ala Tyr Thr Glu Ala Gly Gln Thr Val Ile Asn Ile
    770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Leu Leu Ile Lys
                805                 810                 815
Thr Val Lys Leu Ala Phe Ser Val Thr Asn Asn Val Ile Arg Leu Lys
            820                 825                 830
Pro Pro Ser Asn Val Val Ser Pro Leu Glu Gln Ala Leu Ser Gln His
        835                 840                 845
Gly Ala His Gly Asn Asn Leu Ile Ala Val Leu Ala Lys Tyr Ile Tyr
    850                 855                 860
His Lys His Asp Pro Ala Leu Pro Arg Leu Ala Ile Gln Leu Leu Lys
```

```
                              -continued
865                 870                 875                 880
Arg Leu Ala Thr Val Ala Pro Met Ser Val Tyr Ala Cys Leu Gly Asn
                885                 890                 895
Asp Ala Ala Ala Ile Arg Asp Ala Phe Leu Thr Arg Leu Gln Ser Lys
            900                 905                 910
Ile Glu Asp Met Arg Ile Lys Val Met Ile Leu Glu Phe Leu Thr Val
        915                 920                 925
Ala Val Glu Thr Gln Pro Gly Leu Ile Glu Leu Phe Leu Asn Leu Glu
    930                 935                 940
Val Lys Asp Gly Ser Asp Gly Ser Lys Glu Phe Ser Leu Gly Met Trp
945                 950                 955                 960
Ser Cys Leu His Ala Val Leu Glu Leu Ile Asp Ser Gln Gln Gln Asp
                965                 970                 975
Arg Tyr Trp Cys Pro Pro Leu Leu His Arg Ala Ala Ile Ala Phe Leu
            980                 985                 990
His Ala Leu Trp Gln Asp Arg Arg Asp Ser Ala Met Leu Val Leu Arg
        995                 1000                1005
Thr Lys Pro Lys Phe Trp Glu Asn Leu Thr Ser Pro Leu Phe Gly Thr
    1010                1015                1020
Leu Ser Pro Pro Ser Glu Thr Ser Glu Pro Ser Ile Leu Glu Thr Cys
1025                1030                1035                1040
Ala Leu Ile Met Lys Ile Ile Cys Leu Glu Ile Tyr Tyr Val Val Lys
                1045                1050                1055
Gly Ser Leu Asp Gln Ser Leu Lys Asp Thr Leu Lys Lys Phe Ser Ile
            1060                1065                1070
Glu Lys Arg Phe Ala Tyr Trp Ser Gly Tyr Val Lys Ser Leu Ala Val
        1075                1080                1085
His Val Ala Glu Thr Glu Gly Ser Ser Cys Thr Ser Leu Leu Glu Tyr
    1090                1095                1100
Gln Met Leu Val Ser Ala Trp Arg Met Leu Leu Ile Ile Ala Thr Thr
1105                1110                1115                1120
His Ala Asp Ile Met His Leu Thr Asp Ser Val Val Arg Arg Gln Leu
                1125                1130                1135
Phe Leu Asp Val Leu Asp Gly Thr Lys Ala Leu Leu Leu Val Pro Ala
            1140                1145                1150
Ser Val Asn Cys Leu Arg Leu Gly Ser Met Lys Cys Thr Leu Leu Leu
        1155                1160                1165
Ile Leu Leu Arg Gln Trp Lys Arg Glu Leu Gly Ser Val Asp Glu Ile
    1170                1175                1180
Leu Gly Pro Leu Thr Glu Ile Leu Glu Gly Val Leu Gln Ala Asp Gln
1185                1190                1195                1200
Gln Leu Met Glu Lys Thr Lys Ala Lys Val Phe Ser Ala Phe Ile Thr
                1205                1210                1215
Val Leu Gln Met Lys Glu Met Lys Val Ser Asp Ile Pro Gln Tyr Ser
            1220                1225                1230
Gln Leu Val Leu Asn Val Cys Glu Thr Leu Gln Glu Glu Val Ile Ala
        1235                1240                1245
Leu Phe Asp Gln Thr Arg His Ser Leu Ala Leu Gly Ser Ala Thr Glu
    1250                1255                1260
Asp Lys Asp Ser Met Glu Thr Asp Asp Cys Ser Arg Ser Arg His Arg
1265                1270                1275                1280
Asp Gln Arg Asp Gly Val Cys Val Leu Gly Leu His Leu Ala Lys Glu
            1285                1290                1295
```

```
Leu Cys Glu Val Asp Glu Asp Gly Asp Ser Trp Leu Gln Val Thr Arg
            1300                1305                1310

Arg Leu Pro Ile Leu Pro Thr Leu Leu Thr Thr Leu Glu Val Ser Leu
        1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
                1365                1370                1375

Ser Thr Asn Gly Thr Ala Gln Thr Pro Ser Ala Ser Arg Lys Ser Leu
            1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
                1445                1450                1455

Val Gly Phe Ile Leu Gln Leu Ser Asn Phe Met Lys Glu Trp His Phe
            1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
                1525                1530                1535

Lys Gln Pro Ala Ala Asp Thr Glu Ala Ser Glu Gln Gln Ala Leu His
            1540                1545                1550

Thr Val Gln Tyr Gly Leu Leu Lys Ile Leu Ser Lys Thr Leu Ala Ala
        1555                1560                1565

Leu Arg His Phe Thr Pro Asp Val Cys Gln Ile Leu Leu Asp Gln Ser
    1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
                1605                1610                1615

Thr Val Asn Val Ala Leu Asn Met Leu Gly Glu Leu Asp Lys Lys Lys
            1620                1625                1630

Glu Pro Leu Thr Gln Ala Val Gly Leu Ser Thr Gln Ala Glu Gly Thr
        1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
                1685                1690                1695

Thr Leu Leu Ser Ser Leu Ser Arg Tyr Phe Arg Arg Gly Ala Pro Ser
            1700                1705                1710
```

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 5
<211> LENGTH: 1752
<212> TYPE: PRT
<213> ORGANISM: Homo sapiens

<400> SEQUENCE: 5

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Ser Val Gln Leu
            85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
            115                 120                 125

Ile Ala Asp Tyr Tyr Tyr Glu Glu Arg Thr Cys Ile Leu Arg Cys Val
    130                 135                 140

Leu His Leu Leu Thr Tyr Phe Gln Asp Glu Arg Pro Tyr Arg Val Glu
145                 150                 155                 160

Tyr Ala Asp Cys Val Asp Lys Leu Glu Lys Glu Leu Val Ser Lys Tyr
            165                 170                 175

Arg Gln Gln Phe Glu Glu Leu Tyr Lys Thr Glu Ala Pro Thr Trp Glu
            180                 185                 190

Thr His Gly Asn Leu Met Thr Glu Arg Gln Val Ser Arg Trp Phe Val
        195                 200                 205

Gln Cys Leu Arg Glu Gln Ser Met Leu Leu Glu Ile Ile Phe Leu Tyr
    210                 215                 220

Tyr Ala Tyr Phe Glu Met Ala Pro Ser Asp Leu Leu Val Leu Thr Lys
225                 230                 235                 240

Met Phe Lys Glu Gln Gly Phe Gly Ser Arg Gln Thr Asn Arg His Leu
            245                 250                 255

Val Asp Glu Thr Met Asp Pro Phe Asp Lys Ile Gly Tyr Phe Ser
            260                 265                 270

Ala Leu Ile Leu Val Glu Gly Met Asp Ile Glu Ser Leu His Lys Cys
        275                 280                 285

Ala Leu Asp Asp Arg Arg Glu Leu His Gln Phe Ala Gln Asp Gly Leu
    290                 295                 300

Ile Cys Gln Asp Met Asp Cys Leu Met Leu Thr Phe Gly Asp Ile Pro
305                 310                 315                 320

His His Ala Pro Val Leu Leu Ala Trp Ala Leu Leu Arg His Thr Leu
            325                 330                 335

-continued

```
Asn Pro Glu Glu Thr Ser Ser Val Val Arg Lys Ile Gly Gly Thr Ala
            340                 345                 350

Ile Gln Leu Asn Val Phe Gln Tyr Leu Thr Arg Leu Leu Gln Ser Leu
                355                 360                 365

Ala Ser Gly Gly Asn Asp Cys Thr Ser Thr Ala Cys Met Cys Val
        370                 375                 380

Tyr Gly Leu Leu Ser Phe Val Leu Thr Ser Leu Glu Leu His Thr Leu
385                 390                 395                 400

Gly Asn Gln Gln Asp Ile Ile Asp Thr Ala Cys Glu Val Leu Ala Asp
                405                 410                 415

Pro Ser Leu Pro Glu Leu Phe Trp Gly Thr Glu Pro Thr Ser Gly Leu
                420                 425                 430

Gly Ile Ile Leu Asp Ser Val Cys Gly Met Phe Pro His Leu Leu Ser
                435                 440                 445

Pro Leu Leu Gln Leu Leu Arg Ala Leu Val Ser Gly Lys Ser Thr Ala
        450                 455                 460

Lys Lys Val Tyr Ser Phe Leu Asp Lys Met Ser Phe Tyr Asn Glu Leu
465                 470                 475                 480

Tyr Lys His Lys Pro His Asp Val Ile Ser His Glu Asp Gly Thr Leu
                485                 490                 495

Trp Arg Arg Gln Thr Pro Lys Leu Leu Tyr Pro Leu Gly Gly Gln Thr
                500                 505                 510

Asn Leu Arg Ile Pro Gln Gly Thr Val Gly Gln Val Met Leu Asp Asp
        515                 520                 525

Arg Ala Tyr Leu Val Arg Trp Glu Tyr Ser Tyr Ser Ser Trp Thr Leu
        530                 535                 540

Phe Thr Cys Glu Ile Glu Met Leu Leu His Val Val Ser Thr Ala Asp
545                 550                 555                 560

Val Ile Gln His Cys Gln Arg Val Lys Pro Ile Ile Asp Leu Val His
                565                 570                 575

Lys Val Ile Ser Thr Asp Leu Ser Ile Ala Asp Cys Leu Leu Pro Ile
                580                 585                 590

Thr Ser Arg Ile Tyr Met Leu Leu Gln Arg Leu Thr Thr Val Ile Ser
        595                 600                 605

Pro Pro Val Asp Val Ile Ala Ser Cys Val Asn Cys Leu Thr Val Leu
        610                 615                 620

Ala Ala Arg Asn Pro Ala Lys Val Trp Thr Asp Leu Arg His Thr Gly
625                 630                 635                 640

Phe Leu Pro Phe Val Ala His Pro Val Ser Ser Leu Ser Gln Met Ile
                645                 650                 655

Ser Ala Glu Gly Met Asn Ala Gly Gly Tyr Gly Asn Leu Leu Met Asn
            660                 665                 670

Ser Glu Gln Pro Gln Gly Glu Tyr Gly Val Thr Ile Ala Phe Leu Arg
            675                 680                 685

Leu Ile Thr Thr Leu Val Lys Gly Gln Leu Gly Ser Thr Gln Ser Gln
        690                 695                 700

Gly Leu Val Pro Cys Val Met Phe Val Leu Lys Glu Met Leu Pro Ser
705                 710                 715                 720

Tyr His Lys Trp Arg Tyr Asn Ser His Gly Val Arg Glu Gln Ile Gly
                725                 730                 735

Cys Leu Ile Leu Glu Leu Ile His Ala Ile Leu Asn Leu Cys His Glu
            740                 745                 750
```

```
Thr Asp Leu His Ser Ser His Thr Pro Ser Leu Gln Phe Leu Cys Ile
        755                 760                 765

Cys Ser Leu Ala Tyr Thr Glu Ala Gly Gln Thr Val Ile Asn Ile Met
        770                 775                 780

Gly Ile Gly Val Asp Thr Ile Asp Met Val Met Ala Ala Gln Pro Arg
785                 790                 795                 800

Ser Asp Gly Ala Glu Gly Gln Gly Gln Gly Gln Leu Leu Ile Lys Thr
                805                 810                 815

Val Lys Leu Ala Phe Ser Val Thr Asn Asn Val Ile Arg Leu Lys Pro
        820                 825                 830

Pro Ser Asn Val Val Ser Pro Leu Glu Gln Ala Leu Ser Gln His Gly
        835                 840                 845

Ala His Gly Asn Asn Leu Ile Ala Val Leu Ala Lys Tyr Ile Tyr His
        850                 855                 860

Lys His Asp Pro Ala Leu Pro Arg Leu Ala Ile Gln Leu Leu Lys Arg
865                 870                 875                 880

Leu Ala Thr Val Ala Pro Met Ser Val Tyr Ala Cys Leu Gly Asn Asp
                885                 890                 895

Ala Ala Ala Ile Arg Asp Ala Phe Leu Thr Arg Leu Gln Ser Lys Ile
                900                 905                 910

Glu Asp Met Arg Ile Lys Val Met Ile Leu Glu Phe Leu Thr Val Ala
        915                 920                 925

Val Glu Thr Gln Pro Gly Leu Ile Glu Leu Phe Leu Asn Leu Glu Val
        930                 935                 940

Lys Asp Gly Ser Asp Gly Ser Lys Glu Phe Ser Leu Gly Met Trp Ser
945                 950                 955                 960

Cys Leu His Ala Val Leu Glu Leu Ile Asp Ser Gln Gln Gln Asp Arg
                965                 970                 975

Tyr Trp Cys Pro Pro Leu Leu His Arg Ala Ala Ile Ala Phe Leu His
                980                 985                 990

Ala Leu Trp Gln Asp Arg Arg Asp Ser Ala Met Leu Val Leu Arg Thr
        995                 1000                1005

Lys Pro Lys Phe Trp Glu Asn Leu Thr Ser Pro Leu Phe Gly Thr Leu
    1010                1015                1020

Ser Pro Pro Ser Glu Thr Ser Glu Pro Ser Ile Leu Glu Thr Cys Ala
1025                1030                1035                1040

Leu Ile Met Lys Ile Ile Cys Leu Glu Ile Tyr Tyr Val Val Lys Gly
                1045                1050                1055

Ser Leu Asp Gln Ser Leu Lys Asp Thr Leu Lys Lys Phe Ser Ile Glu
                1060                1065                1070

Lys Arg Phe Ala Tyr Trp Ser Gly Tyr Val Lys Ser Leu Ala Val His
        1075                1080                1085

Val Ala Glu Thr Glu Gly Ser Ser Cys Thr Ser Leu Leu Glu Tyr Gln
        1090                1095                1100

Met Leu Val Ser Ala Trp Arg Met Leu Leu Ile Ile Ala Thr Thr His
1105                1110                1115                1120

Ala Asp Ile Met His Leu Thr Asp Ser Val Val Arg Arg Gln Leu Phe
                1125                1130                1135

Leu Asp Val Leu Asp Gly Thr Lys Ala Leu Leu Leu Val Pro Ala Ser
            1140                1145                1150

Val Asn Cys Leu Arg Leu Gly Ser Met Lys Cys Thr Leu Leu Leu Ile
        1155                1160                1165

Leu Leu Arg Gln Trp Lys Arg Glu Leu Gly Ser Val Asp Glu Ile Leu
```

-continued

```
          1170                1175                1180
Gly Pro Leu Thr Glu Ile Leu Glu Gly Val Leu Gln Ala Asp Gln Gln
    1185                1190                1195                1200

Leu Met Glu Lys Thr Lys Ala Lys Val Phe Ser Ala Phe Ile Thr Val
        1205                1210                1215

Leu Gln Met Lys Glu Met Lys Val Ser Asp Ile Pro Gln Tyr Ser Gln
        1220                1225                1230

Leu Val Leu Asn Val Cys Glu Thr Leu Gln Glu Val Ile Ala Leu
    1235                1240                1245

Phe Asp Gln Thr Arg His Ser Leu Ala Leu Gly Ser Ala Thr Glu Asp
    1250                1255                1260

Lys Asp Ser Met Glu Thr Asp Asp Cys Ser Arg Ser His Arg Asp
1265                1270                1275                1280

Gln Arg Asp Gly Val Cys Val Leu Gly Leu His Leu Ala Lys Glu Leu
        1285                1290                1295

Cys Glu Val Asp Glu Asp Gly Asp Ser Trp Leu Gln Val Thr Arg Arg
        1300                1305                1310

Leu Pro Ile Leu Pro Thr Leu Leu Thr Thr Leu Glu Val Ser Leu Arg
    1315                1320                1325

Met Lys Gln Asn Leu His Phe Thr Glu Ala Thr Leu His Leu Leu Leu
    1330                1335                1340

Thr Leu Ala Arg Thr Gln Gln Gly Ala Thr Ala Val Ala Gly Ala Gly
1345                1350                1355                1360

Ile Thr Gln Ser Ile Cys Leu Pro Leu Leu Ser Val Tyr Gln Leu Ser
        1365                1370                1375

Thr Asn Gly Thr Ala Gln Thr Pro Ser Ala Ser Arg Lys Ser Leu Asp
        1380                1385                1390

Ala Pro Ser Trp Pro Gly Val Tyr Arg Leu Ser Met Ser Leu Met Glu
    1395                1400                1405

Gln Leu Leu Lys Thr Leu Arg Tyr Asn Phe Leu Pro Glu Ala Leu Asp
    1410                1415                1420

Phe Val Gly Val His Gln Glu Arg Thr Leu Gln Cys Leu Asn Ala Val
1425                1430                1435                1440

Arg Thr Val Gln Ser Leu Ala Cys Leu Glu Glu Ala Asp His Thr Val
        1445                1450                1455

Gly Phe Ile Leu Gln Leu Ser Asn Phe Met Lys Glu Trp His Phe His
        1460                1465                1470

Leu Pro Gln Leu Met Arg Asp Ile Gln Val Asn Leu Gly Tyr Leu Cys
    1475                1480                1485

Gln Ala Cys Thr Ser Leu Leu His Ser Arg Lys Met Leu Gln His Tyr
    1490                1495                1500

Leu Gln Asn Lys Asn Gly Asp Gly Leu Pro Ser Ala Val Ala Gln Arg
1505                1510                1515                1520

Val Gln Arg Pro Pro Ser Ala Ala Ser Ala Ala Pro Ser Ser Ser Lys
        1525                1530                1535

Gln Pro Ala Ala Asp Thr Glu Ala Ser Glu Gln Gln Ala Leu His Thr
        1540                1545                1550

Val Gln Tyr Gly Leu Leu Lys Ile Leu Ser Lys Thr Leu Ala Ala Leu
    1555                1560                1565

Arg His Phe Thr Pro Asp Val Cys Gln Ile Leu Leu Asp Gln Ser Leu
    1570                1575                1580

Asp Leu Ala Glu Tyr Asn Phe Leu Phe Ala Leu Ser Phe Thr Thr Pro
1585                1590                1595                1600
```

-continued

Thr Phe Asp Ser Glu Val Ala Pro Ser Phe Gly Thr Leu Leu Ala Thr
              1605                1610                1615

Val Asn Val Ala Leu Asn Met Leu Gly Glu Leu Asp Lys Lys Lys Glu
         1620                1625                1630

Pro Leu Thr Gln Ala Val Gly Leu Ser Thr Gln Ala Glu Gly Thr Arg
         1635                1640                1645

Thr Leu Lys Ser Leu Leu Met Phe Thr Met Glu Asn Cys Phe Tyr Leu
    1650                1655                1660

Leu Ile Ser Gln Ala Met Arg Tyr Leu Arg Asp Pro Ala Val His Pro
1665                1670                1675                1680

Arg Asp Lys Gln Arg Met Lys Gln Glu Leu Ser Ser Glu Leu Ser Thr
              1685                1690                1695

Leu Leu Ser Ser Leu Ser Arg Tyr Phe Arg Arg Gly Ala Pro Ser Ser
         1700                1705                1710

Pro Ala Thr Gly Val Leu Pro Ser Pro Gln Gly Lys Ser Thr Ser Leu
         1715                1720                1725

Ser Lys Ala Ser Pro Glu Ser Gln Glu Pro Leu Ile Gln Leu Val Gln
    1730                1735                1740

Ala Phe Val Arg His Met Gln Arg
1745                1750

<210> SEQ ID NO 6
<211> LENGTH: 1753
<212> TYPE: PRT
<213> ORGANISM: Homo sapiens

<400> SEQUENCE: 6

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu

-continued

```
            210                 215                 220
Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
                260                 265                 270

Ser Ala Leu Ile Leu Val Glu Gly Met Asp Ile Glu Ser Leu His Lys
                275                 280                 285

Cys Ala Leu Asp Asp Arg Arg Glu Leu His Gln Phe Ala Gln Asp Gly
290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
                340                 345                 350

Ala Ile Asn Leu Asn Val Phe Gln Tyr Leu Thr Arg Leu Leu Gln Ser
                355                 360                 365

Leu Ala Ser Gly Gly Asn Asp Cys Thr Thr Ser Thr Ala Cys Met Cys
370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
                420                 425                 430

Leu Gly Ile Ile Leu Asp Ser Val Cys Gly Met Phe Pro His Leu Leu
                435                 440                 445

Ser Pro Leu Leu Gln Leu Leu Arg Ala Leu Val Ser Gly Lys Ser Thr
                450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
                500                 505                 510

Thr Asn Leu Arg Ile Pro Gln Gly Thr Val Gly Gln Val Met Leu Asp
                515                 520                 525

Asp Arg Ala Tyr Leu Val Arg Trp Glu Tyr Ser Tyr Ser Ser Trp Thr
530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
                580                 585                 590

Ile Thr Ser Arg Ile Tyr Met Leu Leu Gln Arg Leu Thr Thr Val Ile
                595                 600                 605

Ser Pro Pro Val Asp Val Ile Ala Ser Cys Val Asn Cys Leu Thr Val
                610                 615                 620

Leu Ala Ala Arg Asn Pro Ala Lys Val Trp Thr Asp Leu Arg His Thr
625                 630                 635                 640
```

-continued

```
Gly Phe Leu Pro Phe Val Ala His Pro Val Ser Ser Leu Ser Gln Met
            645                 650                 655
Ile Ser Ala Glu Gly Met Asn Ala Gly Gly Tyr Gly Asn Leu Leu Met
            660                 665                 670
Asn Ser Glu Gln Pro Gln Gly Glu Tyr Gly Val Thr Ile Ala Phe Leu
            675                 680                 685
Arg Leu Ile Thr Thr Leu Val Lys Gly Gln Leu Gly Ser Thr Gln Ser
690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
            725                 730                 735
Gly Cys Leu Ile Leu Glu Leu Ile Ala Ile Leu Asn Leu Cys His
            740                 745                 750
Glu Thr Asp Leu His Ser Ser His Thr Pro Ser Leu Gln Phe Leu Cys
            755                 760                 765
Ile Cys Ser Leu Ala Tyr Thr Glu Ala Gly Gln Thr Val Ile Asn Ile
770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Leu Leu Ile Lys
            805                 810                 815
Thr Val Lys Leu Ala Phe Ser Val Thr Asn Asn Val Ile Arg Leu Lys
            820                 825                 830
Pro Pro Ser Asn Val Val Ser Pro Leu Glu Gln Ala Leu Ser Gln His
            835                 840                 845
Gly Ala His Gly Asn Asn Leu Ile Ala Val Leu Ala Lys Tyr Ile Tyr
            850                 855                 860
His Lys His Asp Pro Ala Leu Pro Arg Leu Ala Ile Gln Leu Leu Lys
865                 870                 875                 880
Arg Leu Ala Thr Val Ala Pro Met Ser Val Tyr Ala Cys Leu Gly Asn
            885                 890                 895
Asp Ala Ala Ala Ile Arg Asp Ala Phe Leu Thr Arg Leu Gln Ser Lys
            900                 905                 910
Ile Glu Asp Met Arg Ile Lys Val Met Ile Leu Glu Phe Leu Thr Val
            915                 920                 925
Ala Val Glu Thr Gln Pro Gly Leu Ile Glu Leu Phe Leu Asn Leu Glu
            930                 935                 940
Val Lys Asp Gly Ser Asp Gly Ser Lys Glu Phe Ser Leu Gly Met Trp
945                 950                 955                 960
Ser Cys Leu His Ala Val Leu Glu Leu Ile Asp Ser Gln Gln Gln Asp
            965                 970                 975
Arg Tyr Trp Cys Pro Leu Leu His Arg Ala Ala Ile Ala Phe Leu
            980                 985                 990
His Ala Leu Trp Gln Asp Arg Arg Asp Ser Ala Met Leu Val Leu Arg
            995                 1000                1005
Thr Lys Pro Lys Phe Trp Glu Asn Leu Thr Ser Pro Leu Phe Gly Thr
     1010                1015                1020
Leu Ser Pro Pro Ser Glu Thr Ser Glu Pro Ser Ile Leu Glu Thr Cys
1025                1030                1035                1040
Ala Leu Ile Met Lys Ile Ile Cys Leu Glu Ile Tyr Tyr Val Val Lys
            1045                1050                1055
```

-continued

```
Gly Ser Leu Asp Gln Ser Leu Lys Asp Thr Leu Lys Lys Phe Ser Ile
        1060                1065                1070

Glu Lys Arg Phe Ala Tyr Trp Ser Gly Tyr Val Lys Ser Leu Ala Val
        1075                1080                1085

His Val Ala Glu Thr Glu Gly Ser Ser Cys Thr Ser Leu Leu Glu Tyr
        1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
                1125                1130                1135

Phe Leu Asp Val Leu Asp Gly Thr Lys Ala Leu Leu Leu Val Pro Ala
        1140                1145                1150

Ser Val Asn Cys Leu Arg Leu Gly Ser Met Lys Cys Thr Leu Leu Leu
        1155                1160                1165

Ile Leu Leu Arg Gln Trp Lys Arg Glu Leu Gly Ser Val Asp Glu Ile
        1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
        1205                1210                1215

Val Leu Gln Met Lys Glu Met Lys Val Ser Asp Ile Pro Gln Tyr Ser
        1220                1225                1230

Gln Leu Val Leu Asn Val Cys Glu Thr Leu Gln Glu Glu Val Ile Ala
        1235                1240                1245

Leu Phe Asp Gln Thr Arg His Ser Leu Ala Leu Gly Ser Ala Thr Glu
        1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
                1285                1290                1295

Leu Cys Glu Val Asp Glu Asp Gly Asp Ser Trp Leu Gln Val Thr Arg
        1300                1305                1310

Arg Leu Pro Ile Leu Pro Thr Leu Leu Thr Thr Leu Glu Val Ser Leu
        1315                1320                1325

Arg Met Lys Gln Asn Leu His Phe Thr Glu Ala Thr Leu His Leu Leu
        1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
                1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
        1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
                1445                1450                1455

Val Gly Phe Ile Leu Gln Leu Ser Asn Phe Met Lys Glu Trp His Phe
        1460                1465                1470

His Leu Pro Gln Leu Met Arg Asp Ile Gln Val Asn Leu Gly Tyr Leu
```

```
                    1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
                1525                1530                1535

Lys Gln Pro Ala Ala Asp Thr Glu Ala Ser Glu Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
    1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
                1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
                1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 7
<211> LENGTH: 1753
<212> TYPE: PRT
<213> ORGANISM: Homo sapiens

<400> SEQUENCE: 7

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95
```

-continued

```
Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
            115                 120                 125

Ile Ala Asp Tyr Tyr Glu Glu Arg Thr Cys Ile Leu Arg Cys Val
            130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
            195                 200                 205

Val Gln Cys Leu Arg Glu Gln Ser Met Leu Leu Glu Ile Ile Phe Leu
            210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
            275                 280                 285

Cys Ala Leu Asp Asp Arg Arg Glu Leu His Gln Phe Ala Gln Asp Gly
            290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
            355                 360                 365

Leu Ala Ser Gly Gly Asn Asp Cys Thr Thr Ser Thr Ala Cys Met Cys
            370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
            420                 425                 430

Leu Gly Ile Ile Leu Asp Ser Val Cys Gly Met Phe Pro Arg Leu Leu
            435                 440                 445

Ser Pro Leu Leu Gln Leu Leu Arg Ala Leu Val Ser Gly Lys Ser Thr
            450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
            500                 505                 510

Thr Asn Leu Arg Ile Pro Gln Gly Thr Val Gly Gln Val Met Leu Asp
```

-continued

```
            515                 520                 525
Asp Arg Ala Tyr Leu Val Arg Trp Glu Tyr Ser Tyr Ser Ser Trp Thr
        530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
                580                 585                 590

Ile Thr Ser Arg Ile Tyr Met Leu Leu Gln Arg Leu Thr Thr Val Ile
                595                 600                 605

Ser Pro Pro Val Asp Val Ile Ala Ser Cys Val Asn Cys Leu Thr Val
        610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Gly Tyr Gly Asn Leu Leu Met
                660                 665                 670

Asn Ser Glu Gln Pro Gln Gly Glu Tyr Gly Val Thr Ile Ala Phe Leu
                675                 680                 685

Arg Leu Ile Thr Thr Leu Val Lys Gly Gln Leu Gly Ser Thr Gln Ser
        690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
                740                 745                 750

Glu Thr Asp Leu His Ser Ser His Thr Pro Ser Leu Gln Phe Leu Cys
                755                 760                 765

Ile Cys Ser Leu Ala Tyr Thr Glu Ala Gly Gln Thr Val Ile Asn Ile
        770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Leu Leu Ile Lys
                805                 810                 815

Thr Val Lys Leu Ala Phe Ser Val Thr Asn Asn Val Ile Arg Leu Lys
                820                 825                 830

Pro Pro Ser Asn Val Val Ser Pro Leu Glu Gln Ala Leu Ser Gln His
                835                 840                 845

Gly Ala His Gly Asn Asn Leu Ile Ala Val Leu Ala Lys Tyr Ile Tyr
        850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ile Arg Asp Ala Phe Leu Thr Arg Leu Gln Ser Lys
                900                 905                 910

Ile Glu Asp Met Arg Ile Lys Val Met Ile Leu Glu Phe Leu Thr Val
                915                 920                 925

Ala Val Glu Thr Gln Pro Gly Leu Ile Glu Leu Phe Leu Asn Leu Glu
        930                 935                 940
```

-continued

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
            965                 970                 975

Arg Tyr Trp Cys Pro Pro Leu Leu His Arg Ala Ala Ile Ala Phe Leu
        980                 985                 990

His Ala Leu Trp Gln Asp Arg Arg Asp Ser Ala Met Leu Val Leu Arg
    995                 1000                1005

Thr Lys Pro Lys Phe Trp Glu Asn Leu Thr Ser Pro Leu Phe Gly Thr
1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
            1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Lys Ser Leu Ala Val
        1075                1080                1085

His Val Ala Glu Thr Glu Gly Ser Ser Cys Thr Ser Leu Leu Glu Tyr
    1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ala
            1140                1145                1150

Ser Val Asn Cys Leu Arg Leu Gly Ser Met Lys Cys Thr Leu Leu Leu
        1155                1160                1165

Ile Leu Leu Arg Gln Trp Lys Arg Glu Leu Gly Ser Val Asp Glu Ile
    1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

Val Leu Gln Met Lys Glu Met Lys Val Ser Asp Ile Pro Gln Tyr Ser
            1220                1225                1230

Gln Leu Val Leu Asn Val Cys Glu Thr Leu Gln Glu Glu Val Ile Ala
        1235                1240                1245

Leu Phe Asp Gln Thr Arg His Ser Leu Ala Leu Gly Ser Ala Thr Glu
1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
            1300                1305                1310

Arg Leu Pro Ile Leu Pro Thr Leu Leu Thr Thr Leu Glu Val Ser Leu
        1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

```
Gly Ile Thr Gln Ser Ile Cys Leu Pro Leu Leu Ser Val Tyr Gln Leu
            1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
    1395                1400                1405

Glu Gln Leu Leu Lys Thr Leu Arg Tyr Asn Phe Leu Pro Glu Ala Leu
1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Ala Asp His Thr
        1445                1450                1455

Val Gly Phe Ile Leu Gln Leu Ser Asn Phe Met Lys Glu Trp His Phe
            1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Asp Thr Glu Ala Ser Glu Gln Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
1730                1735                1740

Gln Ala Phe Val Arg His Met Gln Arg
1745                1750

<210> SEQ ID NO 8
<211> LENGTH: 1753
<212> TYPE: PRT
```

<213> ORGANISM: Homo sapiens

<400> SEQUENCE: 8

```
Met Ile Arg Lys Ser Lys Ile Thr Ser Val Leu Ser Phe Cys Arg Ser
 1               5                  10                  15

Ser Arg Glu Leu Trp Thr Ile Leu Leu Gly Arg Ser Ala Leu Arg Glu
             20                  25                  30

Leu Ser Gln Ile Glu Ala Glu Leu Asn Lys His Trp Arg Arg Leu Leu
         35                  40                  45

Glu Gly Leu Ser Tyr Tyr Lys Pro Pro Ser Ser Ala Glu Lys
     50                  55                  60

Val Lys Ala Asn Lys Asp Val Ala Ser Pro Leu Lys Glu Leu Gly Leu
 65                  70                  75                  80

Arg Ile Ser Lys Phe Leu Gly Leu Asp Glu Glu Gln Ser Val Gln Leu
                 85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Glu Glu Arg Thr Cys Ile Leu Arg Cys Val
130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
    290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
    370                 375                 380

Val Tyr Gly Leu Leu Ser Phe Val Leu Thr Ser Leu Glu Leu His Thr
385                 390                 395                 400
```

```
Leu Gly Asn Gln Gln Asp Ile Ile Asp Thr Ala Cys Glu Val Leu Ala
            405                 410                 415
Asp Pro Ser Leu Pro Glu Leu Phe Trp Gly Thr Glu Pro Thr Ser Gly
        420                 425                 430
Leu Gly Ile Ile Leu Asp Ser Val Cys Gly Met Phe Pro His Leu Leu
            435                 440                 445
Ser Pro Leu Leu Gln Leu Leu Arg Ala Leu Val Ser Gly Lys Ser Thr
    450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
                485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
            515                 520                 525
Asp Arg Ala Tyr Leu Val Arg Trp Glu Tyr Ser Tyr Ser Ser Trp Thr
    530                 535                 540
Leu Phe Thr Cys Glu Ile Glu Met Ile Leu His Val Val Ser Thr Ala
545                 550                 555                 560
Asp Val Ile Gln His Cys Gln Arg Val Lys Pro Ile Ile Asp Leu Val
                565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
            595                 600                 605
Ser Pro Pro Val Asp Val Ile Ala Ser Cys Val Asn Cys Leu Thr Val
    610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                645                 650                 655
Ile Ser Ala Glu Gly Met Asn Ala Gly Gly Tyr Gly Asn Leu Leu Met
            660                 665                 670
Asn Ser Glu Gln Pro Gln Gly Glu Tyr Gly Val Thr Ile Ala Phe Leu
    675                 680                 685
Arg Leu Ile Thr Thr Leu Val Lys Gly Gln Leu Gly Ser Thr Gln Ser
690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
                725                 730                 735
Gly Cys Leu Ile Leu Glu Leu Ile His Ala Ile Leu Asn Leu Cys His
            740                 745                 750
Glu Thr Asp Leu His Ser Ser His Thr Pro Ser Leu Gln Phe Leu Cys
    755                 760                 765
Ile Cys Ser Leu Ala Tyr Thr Glu Ala Gly Gln Thr Val Ile Asn Ile
770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Gln Leu Leu Ile Lys
                805                 810                 815
Thr Val Lys Leu Ala Phe Ser Val Thr Asn Asn Val Ile Arg Leu Lys
```

```
                820             825             830
Pro Pro Ser Asn Val Val Ser Pro Leu Glu Gln Ala Leu Ser Gln His
            835             840             845

Gly Ala His Gly Asn Asn Leu Ile Ala Val Leu Ala Lys Tyr Ile Tyr
850             855             860

His Lys His Asp Pro Ala Leu Pro Arg Leu Ala Ile Gln Leu Leu Lys
865             870             875             880

Arg Leu Ala Thr Val Ala Pro Met Ser Val Tyr Ala Cys Leu Gly Asn
                885             890             895

Asp Ala Ala Ala Ile Arg Asp Ala Phe Leu Thr Arg Leu Gln Ser Lys
            900             905             910

Ile Glu Asp Met Arg Ile Lys Val Met Ile Leu Glu Phe Leu Thr Val
            915             920             925

Ala Val Glu Thr Gln Pro Gly Leu Ile Glu Leu Phe Leu Asn Leu Glu
            930             935             940

Val Lys Asp Gly Ser Asp Gly Ser Lys Glu Phe Ser Leu Gly Met Trp
945             950             955             960

Ser Cys Leu His Ala Val Leu Glu Leu Ile Asp Ser Gln Gln Gln Asp
                965             970             975

Arg Tyr Trp Cys Pro Leu Leu His Arg Ala Ala Ile Ala Phe Leu
            980             985             990

His Ala Leu Trp Gln Asp Arg Arg Asp Ser Ala Met Leu Val Leu Arg
            995             1000            1005

Thr Lys Pro Lys Phe Trp Glu Asn Leu Thr Ser Pro Leu Phe Gly Thr
        1010            1015            1020

Leu Ser Pro Pro Ser Glu Thr Ser Glu Pro Ser Ile Leu Glu Thr Cys
1025            1030            1035            1040

Ala Leu Ile Met Lys Ile Ile Cys Leu Glu Ile Tyr Tyr Val Val Lys
            1045            1050            1055

Gly Ser Leu Asp Gln Ser Leu Lys Asp Thr Leu Lys Lys Phe Ser Ile
                1060            1065            1070

Glu Lys Arg Phe Ala Tyr Trp Ser Gly Tyr Val Lys Ser Leu Ala Val
        1075            1080            1085

His Val Ala Glu Thr Glu Gly Ser Ser Cys Thr Ser Leu Leu Glu Tyr
        1090            1095            1100

Gln Met Leu Val Ser Ala Trp Arg Met Leu Leu Ile Ile Ala Thr Thr
1105            1110            1115            1120

His Ala Asp Ile Met His Leu Thr Asp Ser Val Val Arg Arg Gln Leu
            1125            1130            1135

Phe Leu Asp Val Leu Asp Gly Thr Lys Ala Leu Leu Leu Val Pro Ala
        1140            1145            1150

Ser Val Asn Cys Leu Arg Leu Gly Ser Met Lys Cys Thr Leu Leu Leu
        1155            1160            1165

Ile Leu Leu Arg Gln Trp Lys Arg Glu Leu Gly Ser Val Asp Glu Ile
    1170            1175            1180

Leu Gly Pro Leu Thr Glu Ile Leu Glu Gly Val Leu Gln Ala Asp Gln
1185            1190            1195            1200

Gln Leu Met Glu Lys Thr Lys Ala Lys Val Phe Ser Ala Phe Ile Thr
        1205            1210            1215

Val Leu Gln Met Lys Glu Met Lys Val Ser Asp Ile Pro Gln Tyr Ser
            1220            1225            1230

Gln Leu Val Leu Asn Val Cys Glu Thr Leu Gln Glu Glu Val Ile Ala
        1235            1240            1245
```

```
Leu Phe Asp Gln Thr Arg His Ser Leu Ala Leu Gly Ser Ala Thr Glu
    1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
        1285                1290                1295

Leu Cys Glu Val Asp Glu Asp Gly Asp Ser Trp Leu Gln Val Thr Arg
            1300                1305                1310

Arg Leu Pro Ile Leu Pro Thr Leu Leu Thr Thr Leu Glu Val Ser Leu
        1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
        1365                1370                1375

Ser Thr Asn Gly Thr Ala Gln Thr Pro Ser Ala Ser Arg Lys Ser Leu
            1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
        1445                1450                1455

Val Gly Phe Ile Leu Gln Leu Ser Asn Phe Met Lys Glu Trp His Phe
            1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
        1525                1530                1535

Lys Gln Pro Ala Ala Asp Thr Glu Ala Ser Glu Gln Gln Ala Leu His
            1540                1545                1550

Thr Val Gln Tyr Gly Leu Leu Lys Ile Leu Ser Lys Thr Leu Ala Ala
        1555                1560                1565

Leu Arg His Phe Thr Pro Asp Val Cys Gln Ile Leu Leu Asp Gln Ser
    1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
        1605                1610                1615

Thr Val Asn Val Ala Leu Asn Met Leu Gly Glu Leu Asp Lys Lys Lys
            1620                1625                1630

Glu Pro Leu Thr Gln Ala Val Gly Leu Ser Thr Gln Ala Glu Gly Thr
        1635                1640                1645

Arg Thr Leu Lys Ser Leu Leu Met Phe Thr Met Glu Asn Cys Phe Tyr
    1650                1655                1660
```

```
Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
                1700                1705                1710

Ser Pro Ala Thr Gly Val Leu Pro Ser Pro Gln Gly Lys Ser Thr Ser
        1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 9
<211> LENGTH: 1753
<212> TYPE: PRT
<213> ORGANISM: Homo sapiens

<400> SEQUENCE: 9

Met Ile Arg Lys Ser Lys Ile Thr Ser Val Leu Ser Phe Cys Arg Ser
  1               5                  10                  15

Ser Arg Glu Leu Trp Thr Ile Leu Leu Gly Arg Ser Ala Leu Arg Glu
             20                  25                  30

Leu Ser Gln Ile Glu Ala Glu Leu Asn Lys His Trp Arg Arg Leu Leu
         35                  40                  45

Glu Gly Leu Ser Tyr Tyr Lys Pro Pro Ser Pro Ser Ala Glu Lys
     50                  55                  60

Val Lys Ala Asn Lys Asp Val Ala Ser Pro Leu Lys Glu Leu Gly Leu
 65                  70                  75                  80

Arg Ile Ser Lys Phe Leu Gly Leu Asp Glu Glu Gln Ser Val Gln Leu
                 85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Gly Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285
```

-continued

```
Cys Ala Leu Asp Asp Arg Arg Glu Leu His Gln Phe Ala Gln Asp Gly
    290                 295                 300
Leu Ile Cys Gln Asp Met Asp Cys Leu Met Leu Thr Phe Gly Asp Ile
305                 310                 315                 320
Pro His His Ala Pro Val Leu Leu Ala Trp Ala Leu Leu Arg His Thr
                325                 330                 335
Leu Asn Pro Glu Glu Thr Ser Ser Val Arg Lys Ile Gly Gly Thr
                340                 345                 350
Ala Ile Gln Leu Asn Val Phe Gln Tyr Leu Thr Arg Leu Leu Gln Ser
            355                 360                 365
Leu Ala Ser Gly Gly Asn Asp Cys Thr Thr Ser Thr Ala Cys Met Cys
    370                 375                 380
Val Tyr Gly Leu Leu Ser Phe Val Leu Thr Ser Leu Glu Leu His Thr
385                 390                 395                 400
Leu Gly Asn Gln Gln Asp Ile Ile Asp Thr Ala Cys Glu Val Leu Ala
                405                 410                 415
Asp Pro Ser Leu Pro Glu Leu Phe Trp Gly Thr Glu Pro Thr Ser Gly
            420                 425                 430
Leu Gly Ile Ile Leu Asp Ser Val Cys Gly Met Phe Pro His Leu Leu
    435                 440                 445
Ser Pro Leu Leu Gln Leu Leu Arg Ala Leu Val Ser Gly Lys Ser Thr
450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
                485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
    515                 520                 525
Asp Arg Ala Tyr Leu Val Arg Trp Glu Tyr Ser Tyr Ser Ser Trp Thr
530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
                565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
    595                 600                 605
Ser Pro Pro Val Asp Val Ile Ala Ser Cys Val Asn Cys Leu Thr Val
610                 615                 620
Leu Ala Ala Arg Asn Pro Ala Lys Val Phe Thr Asp Leu Arg His Thr
625                 630                 635                 640
Gly Phe Leu Pro Phe Val Ala His Pro Val Ser Ser Leu Ser Gln Met
                645                 650                 655
Ile Ser Ala Glu Gly Met Asn Ala Gly Gly Tyr Gly Asn Leu Leu Met
            660                 665                 670
Asn Ser Glu Gln Pro Gln Gly Tyr Gly Val Thr Ile Ala Phe Leu
    675                 680                 685
Arg Leu Ile Thr Thr Leu Val Lys Gly Gln Leu Gly Ser Thr Gln Ser
    690                 695                 700
```

-continued

```
Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
                740                 745                 750

Glu Thr Asp Leu His Ser Ser His Thr Pro Ser Leu Gln Phe Leu Cys
                755                 760                 765

Ile Cys Ser Leu Ala Tyr Thr Glu Ala Gly Gln Thr Val Ile Asn Ile
        770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Gln Leu Leu Ile Lys
                805                 810                 815

Thr Val Lys Leu Ala Phe Ser Val Thr Asn Asn Val Ile Arg Leu Lys
                820                 825                 830

Pro Pro Ser Asn Val Val Ser Pro Leu Glu Gln Ala Leu Ser Gln His
        835                 840                 845

Gly Ala His Gly Asn Asn Leu Ile Ala Val Leu Ala Lys Tyr Ile Tyr
850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ala Ile Arg Asp Ala Phe Leu Thr Arg Leu Gln Ser Lys
        900                 905                 910

Ile Glu Asp Met Arg Ile Lys Val Met Ile Leu Glu Phe Leu Thr Val
        915                 920                 925

Ala Val Glu Thr Gln Pro Gly Leu Ile Glu Leu Phe Leu Asn Leu Glu
        930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
                965                 970                 975

Arg Tyr Trp Cys Pro Pro Leu His Arg Ala Ala Ile Ala Phe Leu
        980                 985                 990

His Ala Leu Trp Gln Asp Arg Arg Asp Ser Ala Met Leu Val Leu Arg
        995                 1000                1005

Thr Lys Pro Lys Phe Trp Glu Asn Leu Thr Ser Pro Leu Phe Gly Thr
1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
                1045                1050                1055

Gly Ser Leu Asp Gln Ser Leu Lys Asp Thr Leu Lys Lys Phe Ser Ile
        1060                1065                1070

Glu Lys Arg Phe Ala Tyr Trp Ser Gly Tyr Val Lys Ser Leu Ala Val
        1075                1080                1085

His Val Ala Glu Thr Glu Gly Ser Ser Cys Thr Ser Leu Leu Glu Tyr
        1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
```

-continued

```
               1125                1130                1135
Phe Leu Asp Val Leu Asp Gly Thr Lys Ala Leu Leu Leu Val Pro Ala
        1140                1145                1150
Ser Val Asn Cys Leu Arg Leu Gly Ser Met Lys Cys Thr Leu Leu Leu
        1155                1160                1165
Ile Leu Leu Arg Gln Trp Lys Arg Glu Leu Gly Ser Val Asp Glu Ile
        1170                1175                1180
Leu Gly Pro Leu Thr Glu Ile Leu Glu Gly Val Leu Gln Ala Asp Gln
    1185                1190                1195                1200
Gln Leu Met Glu Lys Thr Lys Ala Lys Val Phe Ser Ala Phe Ile Thr
        1205                1210                1215
Val Leu Gln Met Lys Glu Met Lys Val Ser Asp Ile Pro Gln Tyr Ser
        1220                1225                1230
Gln Leu Val Leu Asn Val Cys Glu Thr Leu Gln Glu Glu Val Ile Ala
        1235                1240                1245
Leu Phe Asp Gln Thr Arg His Ser Leu Ala Leu Gly Ser Ala Thr Glu
        1250                1255                1260
Asp Lys Asp Ser Met Glu Thr Asp Asp Cys Ser Arg Ser Arg His Arg
    1265                1270                1275                1280
Asp Gln Arg Asp Gly Val Cys Val Leu Gly Leu His Leu Ala Lys Glu
        1285                1290                1295
Leu Cys Glu Val Asp Glu Asp Gly Asp Ser Trp Leu Gln Val Thr Arg
        1300                1305                1310
Arg Leu Pro Ile Leu Pro Thr Leu Leu Thr Thr Leu Glu Val Ser Leu
        1315                1320                1325
Arg Met Lys Gln Asn Leu His Phe Thr Glu Ala Thr Leu His Leu Leu
        1330                1335                1340
Leu Thr Leu Ala Arg Thr Gln Gln Gly Ala Thr Ala Val Ala Gly Ala
    1345                1350                1355                1360
Gly Ile Thr Gln Ser Ile Cys Leu Pro Leu Leu Ser Val Tyr Gln Leu
        1365                1370                1375
Ser Thr Asn Gly Thr Ala Gln Thr Pro Ser Ala Ser Arg Lys Ser Leu
        1380                1385                1390
Asp Ala Pro Ser Trp Pro Gly Val Tyr Arg Leu Ser Met Ser Leu Met
        1395                1400                1405
Glu Gln Leu Leu Lys Thr Leu Arg Tyr Asn Phe Leu Pro Glu Ala Leu
        1410                1415                1420
Asp Phe Val Gly Val His Gln Glu Arg Thr Leu Gln Cys Leu Asn Ala
    1425                1430                1435                1440
Val Arg Thr Val Gln Ser Leu Ala Cys Leu Glu Glu Ala Asp His Thr
        1445                1450                1455
Val Gly Phe Ile Leu Gln Leu Ser Asn Phe Met Lys Glu Trp His Phe
        1460                1465                1470
His Leu Pro Gln Leu Met Arg Asp Ile Gln Val Asn Leu Gly Tyr Leu
        1475                1480                1485
Cys Gln Ala Cys Thr Ser Leu Leu His Ser Arg Lys Met Leu Gln His
        1490                1495                1500
Tyr Leu Gln Asn Lys Asn Gly Asp Gly Leu Pro Ser Ala Val Ala Gln
    1505                1510                1515                1520
Arg Val Gln Arg Pro Pro Ser Ala Ala Ser Ala Ala Pro Ser Ser Ser
        1525                1530                1535
Lys Gln Pro Ala Ala Asp Thr Glu Ala Ser Glu Gln Gln Ala Leu His
        1540                1545                1550
```

```
Thr Val Gln Tyr Gly Leu Leu Lys Ile Leu Ser Lys Thr Leu Ala Ala
        1555                1560                1565

Leu Arg His Phe Thr Pro Asp Val Cys Gln Ile Leu Leu Asp Gln Ser
    1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
1730                1735                1740

Gln Ala Phe Val Arg His Met Gln Arg
1745                1750

<210> SEQ ID NO 10
<211> LENGTH: 1753
<212> TYPE: PRT
<213> ORGANISM: Homo sapiens

<400> SEQUENCE: 10

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
```

-continued

```
            165                 170                 175
Tyr Arg Gln Gln Phe Glu Glu Leu Tyr Lys Thr Glu Ala Pro Thr Trp
            180                 185                 190
Glu Thr His Gly Asn Leu Met Thr Glu Arg Gln Val Ser Arg Trp Phe
            195                 200                 205
Val Gln Cys Leu Arg Glu Gln Ser Met Leu Leu Glu Ile Ile Phe Leu
            210                 215                 220
Tyr Tyr Ala Tyr Phe Glu Met Ala Pro Ser Asp Leu Leu Val Leu Thr
225                 230                 235                 240
Lys Met Phe Lys Glu Gln Gly Phe Gly Ser Arg Gln Thr Asn Arg His
            245                 250                 255
Leu Val Asp Glu Thr Met Asp Pro Phe Val Asp Arg Ile Gly Tyr Phe
            260                 265                 270
Ser Ala Leu Ile Leu Val Glu Gly Met Asp Ile Glu Ser Leu His Lys
            275                 280                 285
Cys Ala Leu Asp Asp Arg Arg Glu Leu His Gln Phe Ala Gln Asp Gly
            290                 295                 300
Leu Ile Cys Gln Asp Met Asp Cys Leu Met Leu Thr Phe Gly Asp Ile
305                 310                 315                 320
Pro His His Ala Pro Val Leu Leu Ala Trp Ala Leu Leu Arg His Thr
            325                 330                 335
Leu Asn Pro Glu Glu Thr Ser Ser Val Val Arg Lys Ile Gly Gly Thr
            340                 345                 350
Ala Ile Gln Leu Asn Val Phe Gln Tyr Leu Thr Arg Leu Leu Gln Ser
            355                 360                 365
Leu Ala Ser Gly Gly Asn Asp Cys Thr Thr Ser Thr Ala Cys Met Cys
            370                 375                 380
Val Tyr Gly Leu Leu Ser Phe Val Leu Thr Ser Leu Glu Leu His Thr
385                 390                 395                 400
Leu Gly Asn Gln Gln Asp Ile Ile Asp Thr Ala Cys Glu Val Leu Ala
            405                 410                 415
Asp Pro Ser Leu Pro Glu Leu Phe Trp Gly Thr Glu Pro Thr Ser Gly
            420                 425                 430
Leu Gly Ile Ile Leu Asp Ser Val Cys Gly Met Phe Pro His Leu Leu
            435                 440                 445
Ser Pro Leu Leu Gln Leu Leu Arg Ala Leu Val Ser Gly Lys Ser Thr
            450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
            485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
            515                 520                 525
Asp Arg Ala Tyr Leu Val Arg Trp Glu Tyr Ser Tyr Ser Ser Trp Thr
            530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
            565                 570                 575
His Lys Val Ile Ser Thr Asp Leu Ser Ile Ala Asp Cys Leu Leu Pro
            580                 585                 590
```

-continued

```
Ile Thr Ser Arg Ile Tyr Met Leu Leu Gln Arg Leu Thr Thr Val Ile
            595                 600                 605
Ser Pro Pro Val Asp Val Ile Ala Ser Cys Val Asn Cys Leu Thr Val
        610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                645                 650                 655
Ile Ser Ala Glu Gly Met Asn Ala Gly Gly Tyr Gly Asn Leu Leu Met
            660                 665                 670
Asn Ser Glu Gln Pro Gln Gly Glu Tyr Gly Val Thr Ile Ala Phe Leu
        675                 680                 685
Arg Leu Ile Thr Thr Leu Val Lys Gly Gln Leu Gly Ser Thr Gln Ser
690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
                725                 730                 735
Gly Cys Leu Ile Leu Glu Leu Ile His Ala Ile Leu Asp Leu Cys His
            740                 745                 750
Glu Thr Asp Leu His Ser Ser His Thr Pro Ser Leu Gln Phe Leu Cys
        755                 760                 765
Ile Cys Ser Leu Ala Tyr Thr Glu Ala Gly Gln Thr Val Ile Asn Ile
770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Leu Leu Ile Lys
                805                 810                 815
Thr Val Lys Leu Ala Phe Ser Val Thr Asn Asn Val Ile Arg Leu Lys
            820                 825                 830
Pro Pro Ser Asn Val Val Ser Pro Leu Glu Gln Ala Leu Ser Gln His
        835                 840                 845
Gly Ala His Gly Asn Asn Leu Ile Ala Val Leu Ala Lys Tyr Ile Tyr
850                 855                 860
His Lys His Asp Pro Ala Leu Pro Arg Leu Ala Ile Gln Leu Leu Lys
865                 870                 875                 880
Arg Leu Ala Thr Val Ala Pro Met Ser Val Tyr Ala Cys Leu Gly Asn
                885                 890                 895
Asp Ala Ala Ile Arg Asp Ala Phe Leu Thr Arg Leu Gln Ser Lys
            900                 905                 910
Ile Glu Asp Met Arg Ile Lys Val Met Ile Leu Glu Phe Leu Thr Val
        915                 920                 925
Ala Val Glu Thr Gln Pro Gly Leu Ile Glu Leu Phe Leu Asn Leu Glu
        930                 935                 940
Val Lys Asp Gly Ser Asp Gly Ser Lys Glu Phe Ser Leu Gly Met Trp
945                 950                 955                 960
Ser Cys Leu His Ala Val Leu Glu Leu Ile Asp Ser Gln Gln Gln Asp
                965                 970                 975
Arg Tyr Trp Cys Pro Pro Leu Leu His Arg Ala Ile Ala Phe Leu
            980                 985                 990
His Ala Leu Trp Gln Asp Arg Arg Asp Ser Ala Met Leu Val Leu Arg
        995                 1000                1005
```

```
Thr Lys Pro Lys Phe Trp Glu Asn Leu Thr Ser Pro Leu Phe Gly Thr
    1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
            1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Lys Ser Leu Ala Val
            1075                1080                1085

His Val Ala Glu Thr Glu Gly Ser Ser Cys Thr Ser Leu Leu Glu Tyr
            1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ala
            1140                1145                1150

Ser Val Asn Cys Leu Arg Leu Gly Ser Met Lys Cys Thr Leu Leu Leu
            1155                1160                1165

Ile Leu Leu Arg Gln Trp Lys Arg Glu Leu Gly Ser Val Asp Glu Ile
            1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

Val Leu Gln Met Lys Glu Met Lys Val Ser Asp Ile Pro Gln Tyr Ser
            1220                1225                1230

Gln Leu Val Leu Asn Val Cys Glu Thr Leu Gln Glu Glu Val Ile Ala
            1235                1240                1245

Leu Phe Asp Gln Thr Arg His Ser Leu Ala Leu Gly Ser Ala Thr Glu
            1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
            1300                1305                1310

Arg Leu Pro Ile Leu Pro Thr Leu Leu Thr Thr Leu Glu Val Ser Leu
            1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
            1365                1370                1375

Ser Thr Asn Gly Thr Ala Gln Thr Pro Ser Ala Ser Arg Lys Ser Leu
            1380                1385                1390

Asp Ala Pro Ser Trp Pro Gly Val Tyr Arg Leu Ser Met Ser Leu Met
            1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
```

```
                1425                1430                1435                1440
Val Arg Thr Val Gln Ser Leu Ala Cys Leu Glu Glu Ala Asp His Thr
                    1445                1450                1455
Val Gly Phe Ile Leu Gln Leu Ser Asn Phe Met Lys Glu Trp His Phe
                1460                1465                1470
His Leu Pro Gln Leu Met Arg Asp Ile Gln Val Asn Leu Gly Tyr Leu
            1475                1480                1485
Cys Gln Ala Cys Thr Ser Leu Leu His Ser Arg Lys Met Leu Gln His
        1490                1495                1500
Tyr Leu Gln Asn Lys Asn Gly Asp Gly Leu Pro Ser Ala Val Ala Gln
1505                1510                1515                1520
Arg Val Gln Arg Pro Pro Ser Ala Ala Ser Ala Ala Pro Ser Ser Ser
                1525                1530                1535
Lys Gln Pro Ala Ala Asp Thr Glu Ala Ser Glu Gln Gln Ala Leu His
            1540                1545                1550
Thr Val Gln Tyr Gly Leu Leu Lys Ile Leu Ser Lys Thr Leu Ala Ala
        1555                1560                1565
Leu Arg His Phe Thr Pro Asp Val Cys Gln Ile Leu Leu Asp Gln Ser
    1570                1575                1580
Leu Asp Leu Ala Glu Tyr Asn Phe Leu Phe Ala Leu Ser Phe Thr Thr
1585                1590                1595                1600
Pro Thr Phe Asp Ser Glu Val Ala Pro Ser Phe Gly Thr Leu Leu Ala
                1605                1610                1615
Thr Val Asn Val Ala Leu Asn Met Leu Gly Glu Leu Asp Lys Lys Lys
            1620                1625                1630
Glu Pro Leu Thr Gln Ala Val Gly Leu Ser Thr Gln Ala Glu Gly Thr
        1635                1640                1645
Arg Thr Leu Lys Ser Leu Leu Met Phe Thr Met Glu Asn Cys Phe Tyr
    1650                1655                1660
Leu Leu Ile Ser Gln Ala Met Arg Tyr Leu Arg Asp Pro Ala Val His
1665                1670                1675                1680
Pro Arg Asp Lys Gln Arg Met Lys Gln Glu Leu Ser Ser Glu Leu Ser
                1685                1690                1695
Thr Leu Leu Ser Ser Leu Ser Arg Tyr Phe Arg Arg Gly Ala Pro Ser
            1700                1705                1710
Ser Pro Ala Thr Gly Val Leu Pro Ser Pro Gln Gly Lys Ser Thr Ser
        1715                1720                1725
Leu Ser Lys Ala Ser Pro Glu Ser Gln Glu Pro Leu Ile Gln Leu Val
    1730                1735                1740
Gln Ala Phe Val Arg His Met Gln Arg
1745                1750

<210> SEQ ID NO 11
<211> LENGTH: 1753
<212> TYPE: PRT
<213> ORGANISM: Homo sapiens

<400> SEQUENCE: 11

Met Ile Arg Lys Ser Lys Ile Thr Ser Val Leu Ser Phe Cys Arg Ser
1               5                   10                  15
Ser Arg Glu Leu Trp Thr Ile Leu Leu Gly Arg Ser Ala Leu Arg Glu
            20                  25                  30
Leu Ser Gln Ile Glu Ala Glu Leu Asn Lys His Trp Arg Arg Leu Leu
        35                  40                  45
```

```
Glu Gly Leu Ser Tyr Tyr Lys Pro Pro Ser Ser Ala Glu Lys
     50                  55                  60

Val Lys Ala Asn Lys Asp Val Ala Ser Pro Leu Lys Glu Leu Gly Leu
 65              70                  75                      80

Arg Ile Ser Lys Phe Leu Gly Leu Asp Glu Glu Gln Ser Val Gln Leu
                 85                  90                  95

Leu Gln Cys Tyr Leu Gln Glu Asp Tyr Arg Gly Thr Arg Asp Ser Val
             100                 105                 110

Lys Thr Val Leu Gln Asp Glu Arg Gln Ser Gln Ala Leu Ile Leu Lys
             115                 120                 125

Ile Ala Asp Tyr Tyr Glu Glu Arg Thr Cys Ile Leu Arg Cys Val
     130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                 165                 170                 175

Tyr Arg Gln Gln Phe Glu Glu Leu Tyr Lys Thr Glu Ala Pro Thr Trp
             180                 185                 190

Glu Thr His Gly Asn Leu Met Thr Glu Arg Gln Val Ser Arg Trp Phe
         195                 200                 205

Val Gln Cys Leu Arg Glu Gln Ser Met Leu Leu Glu Ile Ile Phe Leu
210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                 245                 250                 255

Leu Val Asp Glu Thr Met Asp Pro Phe Val Asp Arg Ile Gly Tyr Phe
             260                 265                 270

Ser Ala Leu Ile Leu Val Glu Gly Met Asp Ile Glu Ser Leu His Lys
             275                 280                 285

Cys Ala Leu Asp Asp Arg Arg Glu Leu His Gln Phe Ala Gln Asp Gly
     290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                 325                 330                 335

Leu Asn Pro Glu Glu Thr Ser Ser Val Val Arg Lys Ile Gly Gly Thr
             340                 345                 350

Ala Ile Gln Leu Asn Val Phe Gln Tyr Leu Thr Arg Leu Leu Gln Ser
             355                 360                 365

Leu Ala Ser Gly Gly Asn Asp Cys Thr Thr Ser Thr Ala Cys Met Cys
     370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                 405                 410                 415

Asp Pro Ser Leu Pro Glu Leu Phe Trp Gly Thr Glu Pro Thr Ser Gly
             420                 425                 430

Leu Gly Ile Ile Leu Asp Ser Val Cys Gly Met Phe Pro His Leu Leu
             435                 440                 445

Ser Pro Leu Leu Gln Leu Leu Arg Ala Leu Val Ser Gly Lys Ser Thr
     450                 455                 460

Ala Lys Lys Val Tyr Ser Phe Leu Asp Lys Met Ser Phe Tyr Asn Glu
```

```
                465                 470                 475                 480
Leu Tyr Lys His Lys Pro His Asp Val Ile Ser His Glu Asp Gly Thr
                    485                 490                 495
Leu Trp Arg Arg Gln Thr Pro Lys Leu Leu Tyr Pro Leu Gly Gly Gln
                500                 505                 510
Thr Asn Leu Arg Ile Pro Gln Gly Thr Val Gly Gln Val Met Leu Asp
                515                 520                 525
Asp Arg Ala Tyr Leu Val Arg Trp Glu Tyr Ser Tyr Ser Ser Trp Thr
            530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
                565                 570                 575
His Lys Val Ile Ser Thr Asp Leu Ser Ile Ala Asp Cys Leu Leu Pro
                580                 585                 590
Ile Thr Ser Arg Ile Tyr Met Leu Leu Gln Arg Leu Thr Thr Val Ile
                595                 600                 605
Ser Pro Pro Val Asp Val Ile Ala Ser Cys Val Asn Cys Leu Thr Val
        610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                645                 650                 655
Ile Ser Ala Glu Gly Met Asn Ala Gly Gly Tyr Gly Asn Leu Leu Met
                660                 665                 670
Asn Ser Glu Gln Pro Gln Gly Glu Tyr Gly Val Thr Ile Ala Phe Leu
                675                 680                 685
Arg Leu Ile Thr Thr Leu Val Lys Gly Gln Leu Gly Ser Thr Gln Ser
        690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
                725                 730                 735
Gly Cys Leu Ile Leu Glu Leu Ile His Ala Ile Leu Asn Leu Cys His
                740                 745                 750
Glu Thr Asp Leu His Ser Ser His Thr Pro Ser Leu Gln Phe Leu Cys
            755                 760                 765
Ile Cys Ser Leu Ala Tyr Thr Glu Ala Gly Gln Thr Val Ile Asn Ile
        770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Leu Leu Ile Lys
                    805                 810                 815
Thr Val Lys Leu Ala Phe Ser Val Thr Asn Asn Val Ile Arg Leu Lys
                820                 825                 830
Pro Pro Ser Asn Val Met Ser Pro Leu Glu Gln Ala Leu Ser Gln His
            835                 840                 845
Gly Ala His Gly Asn Asn Leu Ile Ala Val Leu Ala Lys Tyr Ile Tyr
        850                 855                 860
His Lys His Asp Pro Ala Leu Pro Arg Leu Ala Ile Gln Leu Leu Lys
865                 870                 875                 880
Arg Leu Ala Thr Val Ala Pro Met Ser Val Tyr Ala Cys Leu Gly Asn
                    885                 890                 895
```

```
Asp Ala Ala Ile Arg Asp Ala Phe Leu Thr Arg Leu Gln Ser Lys
            900                 905                 910

Ile Glu Asp Met Arg Ile Lys Val Met Ile Leu Glu Phe Leu Thr Val
        915                 920                 925

Ala Val Glu Thr Gln Pro Gly Leu Ile Glu Leu Phe Leu Asn Leu Glu
        930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Asp
            965                 970                 975

Arg Tyr Trp Cys Pro Pro Leu Leu His Arg Ala Ala Ile Ala Phe Leu
            980                 985                 990

His Ala Leu Trp Gln Asp Arg Arg Asp Ser Ala Met Leu Val Leu Arg
            995                 1000                1005

Thr Lys Pro Lys Phe Trp Glu Asn Leu Thr Ser Pro Leu Phe Gly Thr
    1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
            1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Lys Ser Leu Ala Val
            1075                1080                1085

His Val Ala Glu Thr Glu Gly Ser Ser Cys Thr Ser Leu Leu Glu Tyr
            1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ala
            1140                1145                1150

Ser Val Asn Cys Leu Arg Leu Gly Ser Met Lys Cys Thr Leu Leu Leu
            1155                1160                1165

Ile Leu Leu Arg Gln Trp Lys Arg Glu Leu Gly Ser Val Asp Glu Ile
            1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

Val Leu Gln Met Lys Glu Met Lys Val Ser Asp Ile Pro Gln Tyr Ser
            1220                1225                1230

Gln Leu Val Leu Asn Val Cys Glu Thr Leu Gln Glu Glu Val Ile Ala
            1235                1240                1245

Leu Phe Asp Gln Thr Arg His Ser Leu Ala Leu Gly Ser Ala Thr Glu
            1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
            1300                1305                1310
```

-continued

```
Arg Leu Pro Ile Leu Pro Thr Leu Leu Thr Leu Glu Val Ser Leu
    1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
        1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
            1445                1450                1455

Val Gly Phe Ile Leu Gln Leu Ser Asn Phe Met Lys Glu Trp His Phe
        1460                1465                1470

His Leu Pro Gln Leu Met Arg Asp Ile Gln Val Asn Leu Gly Tyr Leu
    1475                1480                1485

Cys Gln Ala Cys Thr Ser Leu Leu His Ser Arg Lys Met Leu Gln His
        1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Asp Thr Glu Ala Ser Glu Gln Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
    1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
```

```
                1730                1735                1740
Gln Ala Phe Val Arg His Met Gln Arg
1745                1750

<210> SEQ ID NO 12
<211> LENGTH: 1753
<212> TYPE: PRT
<213> ORGANISM: Homo sapiens

<400> SEQUENCE: 12

Met Ile Arg Lys Ser Lys Ile Thr Ser Val Leu Ser Phe Cys Arg Ser
  1               5                  10                  15

Ser Arg Glu Leu Trp Thr Ile Leu Leu Gly Arg Ser Ala Leu Arg Glu
             20                  25                  30

Leu Ser Gln Ile Glu Ala Glu Leu Asn Lys His Trp Arg Arg Leu Leu
         35                  40                  45

Glu Gly Leu Ser Tyr Tyr Lys Pro Pro Ser Ser Ala Glu Lys
     50                  55                  60

Val Lys Ala Asn Lys Asp Val Ala Ser Pro Leu Lys Glu Leu Gly Leu
 65                  70                  75                  80

Arg Ile Ser Lys Phe Leu Gly Leu Asp Glu Glu Gln Ser Val Gln Leu
                 85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
    290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350
```

-continued

```
Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
        370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
                420                 425                 430

Leu Gly Ile Ile Leu Asp Ser Val Cys Gly Met Phe Pro His Leu Leu
            435                 440                 445

Ser Pro Leu Leu Gln Leu Leu Arg Ala Leu Val Ser Gly Lys Ser Thr
        450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
                500                 505                 510

Thr Asn Leu Arg Ile Pro Gln Gly Thr Val Gly Gln Val Met Leu Asp
            515                 520                 525

Asp Arg Ala Tyr Leu Val Arg Trp Glu Tyr Ser Tyr Ser Ser Trp Thr
        530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
            580                 585                 590

Ile Thr Ser Arg Ile Tyr Met Leu Leu Gln Arg Leu Thr Thr Val Ile
        595                 600                 605

Ser Pro Pro Val Asp Val Ile Ala Ser Cys Val Asn Cys Leu Thr Val
        610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Gly Tyr Gly Asn Leu Leu Met
                660                 665                 670

Asn Ser Glu Gln Pro Gln Gly Glu Tyr Gly Val Thr Ile Ala Phe Leu
            675                 680                 685

Arg Leu Ile Thr Thr Leu Val Lys Gly Gln Leu Gly Ser Thr Gln Ser
        690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
            740                 745                 750

Glu Thr Asp Leu His Ser Ser His Thr Pro Ser Leu Gln Phe Leu Cys
        755                 760                 765

Ile Cys Ser Leu Ala Tyr Thr Glu Ala Gly Gln Thr Val Ile Asn Ile
```

```
             770                 775                 780
Met Gly Ile Gly Val Asp Thr Ile Asp Met Val Met Ala Ala Gln Pro
785                 790                 795                 800

Arg Ser Asp Gly Ala Glu Gly Gln Gly Gln Gly Gln Leu Leu Ile Lys
                805                 810                 815

Thr Val Lys Leu Ala Phe Ser Val Thr Asn Asn Val Ile Arg Leu Lys
                820                 825                 830

Pro Pro Ser Asn Val Val Ser Pro Leu Glu Gln Ala Leu Ser Gln His
                835                 840                 845

Gly Ala His Gly Asn Asn Leu Ile Ala Val Leu Ala Lys Tyr Ile Tyr
850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ala Ile Arg Asp Ala Phe Leu Thr Arg Leu Gln Ser Lys
                900                 905                 910

Ile Glu Asp Met Arg Ile Lys Val Met Ile Leu Glu Phe Leu Thr Val
                915                 920                 925

Ala Val Glu Thr Gln Pro Gly Leu Ile Glu Leu Phe Leu Asn Leu Glu
930                 935                 940

Val Lys Asp Gly Ser Asp Gly Ser Lys Glu Phe Ser Leu Thr Met Trp
945                 950                 955                 960

Ser Cys Leu His Ala Val Leu Glu Leu Ile Asp Ser Gln Gln Gln Asp
                965                 970                 975

Arg Tyr Trp Cys Pro Pro Leu Leu His Arg Ala Ala Ile Ala Phe Leu
                980                 985                 990

His Ala Leu Trp Gln Asp Arg Arg Asp Ser Ala Met Leu Val Leu Arg
                995                1000                1005

Thr Lys Pro Lys Phe Trp Glu Asn Leu Thr Ser Pro Leu Phe Gly Thr
                1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Lys
                1045                1050                1055

Gly Ser Leu Asp Gln Ser Leu Lys Asp Thr Leu Lys Lys Phe Ser Ile
                1060                1065                1070

Glu Lys Arg Phe Ala Tyr Trp Ser Gly Tyr Val Lys Ser Leu Ala Val
                1075                1080                1085

His Val Ala Glu Thr Glu Gly Ser Ser Cys Thr Ser Leu Leu Glu Tyr
                1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
                1125                1130                1135

Phe Leu Asp Val Leu Asp Gly Thr Lys Ala Leu Leu Leu Val Pro Ala
                1140                1145                1150

Ser Val Asn Cys Leu Arg Leu Gly Ser Met Lys Cys Thr Leu Leu Leu
                1155                1160                1165

Ile Leu Leu Arg Gln Trp Lys Arg Glu Leu Gly Ser Val Asp Glu Ile
                1170                1175                1180

Leu Gly Pro Leu Thr Glu Ile Leu Glu Gly Val Leu Gln Ala Asp Gln
1185                1190                1195                1200
```

```
Gln Leu Met Glu Lys Thr Lys Ala Lys Val Phe Ser Ala Phe Ile Thr
            1205                1210                1215
Val Leu Gln Met Lys Glu Met Lys Val Ser Asp Ile Pro Gln Tyr Ser
            1220                1225                1230
Gln Leu Val Leu Asn Val Cys Glu Thr Leu Gln Glu Glu Val Ile Ala
            1235                1240                1245
Leu Phe Asp Gln Thr Arg His Ser Leu Ala Leu Gly Ser Ala Thr Glu
            1250                1255                1260
Asp Lys Asp Ser Met Glu Thr Asp Asp Cys Ser Arg Ser Arg His Arg
1265                1270                1275                1280
Asp Gln Arg Asp Gly Val Cys Val Leu Gly Leu His Leu Ala Lys Glu
            1285                1290                1295
Leu Cys Glu Val Asp Glu Asp Gly Asp Ser Trp Leu Gln Val Thr Arg
            1300                1305                1310
Arg Leu Pro Ile Leu Pro Thr Leu Leu Thr Thr Leu Glu Val Ser Leu
            1315                1320                1325
Arg Met Lys Gln Asn Leu His Phe Thr Glu Ala Thr Leu His Leu Leu
            1330                1335                1340
Leu Thr Leu Ala Arg Thr Gln Gln Gly Ala Thr Ala Val Ala Gly Ala
1345                1350                1355                1360
Gly Ile Thr Gln Ser Ile Cys Leu Pro Leu Leu Ser Val Tyr Gln Leu
            1365                1370                1375
Ser Thr Asn Gly Thr Ala Gln Thr Pro Ser Ala Ser Arg Lys Ser Leu
            1380                1385                1390
Asp Ala Pro Ser Trp Pro Gly Val Tyr Arg Leu Ser Met Ser Leu Met
            1395                1400                1405
Glu Gln Leu Leu Lys Thr Leu Arg Tyr Asn Phe Leu Pro Glu Ala Leu
            1410                1415                1420
Asp Phe Val Gly Val His Gln Glu Arg Thr Leu Gln Cys Leu Asn Ala
1425                1430                1435                1440
Val Arg Thr Val Gln Ser Leu Ala Cys Leu Glu Glu Ala Asp His Thr
            1445                1450                1455
Val Gly Phe Ile Leu Gln Leu Ser Asn Phe Met Lys Glu Trp His Phe
            1460                1465                1470
His Leu Pro Gln Leu Met Arg Asp Ile Gln Val Asn Leu Gly Tyr Leu
            1475                1480                1485
Cys Gln Ala Cys Thr Ser Leu Leu His Ser Arg Lys Met Leu Gln His
            1490                1495                1500
Tyr Leu Gln Asn Lys Asn Gly Asp Gly Leu Pro Ser Ala Val Ala Gln
1505                1510                1515                1520
Arg Val Gln Arg Pro Pro Ser Ala Ala Ser Ala Ala Pro Ser Ser Ser
            1525                1530                1535
Lys Gln Pro Ala Ala Asp Thr Glu Ala Ser Glu Gln Gln Ala Leu His
            1540                1545                1550
Thr Val Gln Tyr Gly Leu Leu Lys Ile Leu Ser Lys Thr Leu Ala Ala
            1555                1560                1565
Leu Arg His Phe Thr Pro Asp Val Cys Gln Ile Leu Leu Asp Gln Ser
            1570                1575                1580
Leu Asp Leu Ala Glu Tyr Asn Phe Leu Phe Ala Leu Ser Phe Thr Thr
1585                1590                1595                1600
Pro Thr Phe Asp Ser Glu Val Ala Pro Ser Phe Gly Thr Leu Leu Ala
            1605                1610                1615
```

```
Thr Val Asn Val Ala Leu Asn Met Leu Gly Glu Leu Asp Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
            1700                1705                1710

Ser Pro Ala Thr Gly Val Leu Pro Ser Pro Gln Gly Lys Ser Thr Ser
            1715                1720                1725

Leu Ser Lys Ala Ser Pro Glu Ser Gln Glu Pro Leu Ile Gln Leu Val
        1730                1735                1740

Gln Ala Phe Val Arg His Met Gln Arg
1745                1750

<210> SEQ ID NO 13
<211> LENGTH: 1753
<212> TYPE: PRT
<213> ORGANISM: Homo sapiens

<400> SEQUENCE: 13

Met Ile Arg Lys Ser Lys Ile Thr Ser Val Leu Ser Phe Cys Arg Ser
 1               5                  10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Leu Val Leu Thr
225                 230                 235                 240
```

-continued

```
Lys Met Phe Lys Glu Gln Gly Phe Gly Ser Arg Gln Thr Asn Arg His
                245                 250                 255
Leu Val Asp Glu Thr Met Asp Pro Phe Val Asp Arg Ile Gly Tyr Phe
            260                 265                 270
Ser Ala Leu Ile Leu Val Glu Gly Met Asp Ile Glu Ser Leu His Lys
        275                 280                 285
Cys Ala Leu Asp Asp Arg Arg Glu Leu His Gln Phe Ala Gln Asp Gly
    290                 295                 300
Leu Ile Cys Gln Asp Met Asp Cys Leu Met Leu Thr Phe Gly Asp Ile
305                 310                 315                 320
Pro His His Ala Pro Val Leu Leu Ala Trp Ala Leu Leu Arg His Thr
                325                 330                 335
Leu Asn Pro Glu Glu Thr Ser Ser Val Val Arg Lys Ile Gly Gly Thr
            340                 345                 350
Ala Ile Gln Leu Asn Val Phe Gln Tyr Leu Thr Arg Leu Leu Gln Ser
        355                 360                 365
Leu Ala Ser Gly Gly Asn Asp Cys Thr Thr Ser Thr Ala Cys Met Cys
    370                 375                 380
Val Tyr Gly Leu Leu Ser Phe Val Leu Thr Ser Leu Glu Leu His Thr
385                 390                 395                 400
Leu Gly Asn Gln Gln Asp Ile Ile Asp Thr Ala Cys Glu Val Leu Ala
                405                 410                 415
Asp Pro Ser Leu Pro Glu Leu Phe Trp Gly Thr Glu Pro Thr Ser Gly
            420                 425                 430
Leu Gly Ile Ile Leu Asp Ser Val Cys Gly Met Phe Pro His Leu Leu
        435                 440                 445
Ser Pro Leu Leu Gln Leu Leu Arg Ala Leu Val Ser Gly Lys Ser Thr
    450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
                485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
        515                 520                 525
Asp Arg Ala Tyr Leu Val Arg Trp Glu Tyr Ser Tyr Ser Ser Trp Thr
    530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
                565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
        595                 600                 605
Ser Pro Pro Val Asp Val Ile Ala Ser Cys Val Asn Cys Leu Thr Val
    610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                645                 650                 655
```

-continued

```
Ile Ser Ala Glu Gly Met Asn Ala Gly Gly Tyr Gly Asn Leu Leu Met
            660                 665                 670

Asn Ser Glu Gln Pro Gln Gly Glu Tyr Gly Val Thr Ile Ala Phe Leu
            675                 680                 685

Arg Leu Ile Thr Thr Leu Val Lys Gly Gln Leu Gly Ser Thr Gln Ser
        690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
            740                 745                 750

Glu Thr Asp Leu His Ser Ser His Thr Pro Ser Leu Gln Phe Leu Cys
            755                 760                 765

Ile Cys Ser Leu Ala Tyr Thr Glu Ala Gly Gln Thr Val Ile Asn Ile
770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Leu Leu Ile Lys
                805                 810                 815

Thr Val Lys Leu Ala Phe Ser Val Thr Asn Asn Val Ile Arg Leu Lys
            820                 825                 830

Pro Pro Ser Asn Val Val Ser Pro Leu Glu Gln Ala Leu Ser Gln His
            835                 840                 845

Gly Ala His Gly Asn Asn Leu Ile Ala Val Leu Ala Lys Tyr Ile Tyr
        850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ile Arg Asp Ala Phe Leu Thr Arg Leu Gln Ser Lys
            900                 905                 910

Ile Glu Asp Met Arg Ile Lys Val Met Ile Leu Glu Phe Leu Thr Val
            915                 920                 925

Ala Val Glu Thr Gln Pro Gly Leu Ile Glu Leu Phe Leu Asn Leu Glu
        930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
                965                 970                 975

Arg Tyr Trp Cys Pro Pro Leu His Arg Ala Ala Ile Ala Phe Leu
            980                 985                 990

His Ala Leu Trp Gln Asp Arg Arg Asp Ser Ala Met Leu Val Leu Arg
        995                 1000                1005

Thr Lys Pro Lys Phe Trp Glu Asn Leu Thr Ser Pro Leu Phe Gly Thr
    1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
                1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Arg Ser Leu Ala Val
```

-continued

```
            1075                1080                1085

His Val Ala Glu Thr Glu Gly Ser Ser Cys Thr Ser Leu Leu Glu Tyr
    1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ala
        1140                1145                1150

Ser Val Asn Cys Leu Arg Leu Gly Ser Met Lys Cys Thr Leu Leu Leu
    1155                1160                1165

Ile Leu Leu Arg Gln Trp Lys Arg Glu Leu Gly Ser Val Asp Glu Ile
1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
        1205                1210                1215

Val Leu Gln Met Lys Glu Met Lys Val Ser Asp Ile Pro Gln Tyr Ser
        1220                1225                1230

Gln Leu Val Leu Asn Val Cys Glu Thr Leu Gln Glu Glu Val Ile Ala
        1235                1240                1245

Leu Phe Asp Gln Thr Arg His Ser Leu Ala Leu Gly Ser Ala Thr Glu
    1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
        1300                1305                1310

Arg Leu Pro Ile Leu Pro Thr Leu Thr Thr Leu Glu Val Ser Leu
    1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
            1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
    1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
            1445                1450                1455

Val Gly Phe Ile Leu Gln Leu Ser Asn Phe Met Lys Glu Trp His Phe
        1460                1465                1470

His Leu Pro Gln Leu Met Arg Asp Ile Gln Val Asn Leu Gly Tyr Leu
    1475                1480                1485

Cys Gln Ala Cys Thr Ser Leu Leu His Ser Arg Lys Met Leu Gln His
    1490                1495                1500
```

-continued

```
Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Asp Thr Glu Ala Ser Glu Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
                1605                1610                1615

Thr Val Asn Val Ala Leu Asn Met Leu Gly Glu Leu Asp Lys Lys Lys
            1620                1625                1630

Glu Pro Leu Thr Gln Ala Val Gly Leu Ser Thr Gln Ala Glu Gly Thr
        1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
                1685                1690                1695

Thr Leu Leu Ser Ser Leu Ser Arg Tyr Phe Arg Arg Gly Ala Pro Ser
            1700                1705                1710

Ser Pro Ala Thr Gly Val Leu Pro Ser Pro Gln Gly Lys Ser Thr Ser
        1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 14
<211> LENGTH: 1753
<212> TYPE: PRT
<213> ORGANISM: Homo sapiens

<400> SEQUENCE: 14

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
```

-continued

```
            115                 120                 125
Ile Ala Asp Tyr Tyr Glu Glu Arg Thr Cys Ile Leu Arg Cys Val
        130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
    290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
    370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
            420                 425                 430

Leu Gly Ile Ile Leu Asp Ser Val Cys Gly Met Phe Pro His Leu Leu
        435                 440                 445

Ser Pro Leu Leu Gln Leu Leu Arg Ala Leu Val Ser Gly Lys Ser Thr
    450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
            500                 505                 510

Thr Asn Leu Arg Ile Pro Gln Gly Thr Val Gly Gln Val Met Leu Asp
        515                 520                 525

Asp Arg Ala Tyr Leu Val Arg Trp Glu Tyr Ser Tyr Ser Ser Trp Thr
    530                 535                 540
```

-continued

```
Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
                580                 585                 590

Ile Thr Ser Arg Ile Tyr Met Leu Leu Gln Arg Leu Thr Thr Val Ile
                595                 600                 605

Ser Pro Pro Val Asp Val Ile Ala Ser Cys Val Asn Cys Leu Thr Val
        610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Gly Tyr Gly Asn Leu Leu Met
                660                 665                 670

Asn Ser Glu Gln Pro Gln Gly Glu Tyr Gly Val Thr Ile Ala Phe Leu
                675                 680                 685

Arg Leu Ile Thr Thr Leu Val Lys Gly Gln Leu Gly Ser Thr Gln Ser
                690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
                740                 745                 750

Glu Thr Asp Leu His Ser Ser His Thr Pro Ser Leu Gln Phe Leu Cys
                755                 760                 765

Ile Cys Ser Leu Ala Tyr Thr Glu Ala Gly Gln Thr Val Ile Asn Ile
                770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Leu Leu Ile Lys
                805                 810                 815

Thr Val Lys Leu Ala Phe Ser Val Thr Asn Asn Val Ile Arg Leu Lys
                820                 825                 830

Pro Pro Ser Asn Val Val Ser Pro Leu Glu Gln Ala Leu Ser Gln His
                835                 840                 845

Gly Ala His Gly Asn Asn Leu Ile Ala Val Leu Ala Lys Tyr Ile Tyr
850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ile Arg Asp Ala Phe Leu Thr Arg Leu Gln Ser Lys
                900                 905                 910

Ile Glu Asp Met Arg Ile Lys Val Met Ile Leu Glu Phe Leu Thr Val
                915                 920                 925

Ala Val Glu Thr Gln Pro Gly Leu Ile Glu Leu Phe Leu Asn Leu Glu
                930                 935                 940

Val Lys Asp Gly Ser Asp Gly Ser Lys Glu Phe Ser Leu Gly Met Trp
945                 950                 955                 960
```

-continued

```
Ser Cys Leu His Ala Val Leu Glu Leu Ile Asp Ser Gln Gln Asp
            965                 970                 975

Arg Tyr Trp Cys Pro Pro Leu Leu His Arg Ala Ala Ile Ala Phe Leu
            980                 985                 990

His Ala Leu Trp Gln Asp Arg Arg Asp Ser Ala Met Leu Val Leu Arg
            995                 1000                1005

Thr Lys Pro Lys Phe Trp Glu Asn Leu Thr Ser Pro Leu Phe Gly Thr
        1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
            1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Lys Ser Leu Ala Val
            1075                1080                1085

His Val Ala Glu Thr Glu Gly Ser Ser Cys Thr Ser Leu Leu Glu Tyr
            1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ser
            1140                1145                1150

Ser Val Asn Cys Leu Arg Leu Gly Ser Met Lys Cys Thr Leu Leu Leu
            1155                1160                1165

Ile Leu Leu Arg Gln Trp Lys Arg Glu Leu Gly Ser Val Asp Glu Ile
            1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

Val Leu Gln Met Lys Glu Met Lys Val Ser Asp Ile Pro Gln Tyr Ser
            1220                1225                1230

Gln Leu Val Leu Asn Val Cys Glu Thr Leu Gln Glu Glu Val Ile Ala
            1235                1240                1245

Leu Phe Asp Gln Thr Arg His Ser Leu Ala Leu Gly Ser Ala Thr Glu
            1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
            1300                1305                1310

Arg Leu Pro Ile Leu Pro Thr Leu Thr Thr Leu Glu Val Ser Leu
            1315                1320                1325

Arg Met Lys Gln Asn Leu His Phe Thr Glu Ala Thr Leu His Leu Leu
            1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
            1365                1370                1375

Ser Thr Asn Gly Thr Ala Gln Thr Pro Ser Ala Ser Arg Lys Ser Leu
```

```
                       1380            1385            1390
Asp Ala Pro Ser Trp Pro Gly Val Tyr Arg Leu Ser Met Ser Leu Met
        1395            1400            1405

Glu Gln Leu Leu Lys Thr Leu Arg Tyr Asn Phe Leu Pro Glu Ala Leu
    1410            1415            1420

Asp Phe Val Gly Val His Gln Glu Arg Thr Leu Gln Cys Leu Asn Ala
1425            1430            1435            1440

Val Arg Thr Val Gln Ser Leu Ala Cys Leu Glu Ala Asp His Thr
            1445            1450            1455

Val Gly Phe Ile Leu Gln Leu Ser Asn Phe Met Lys Glu Trp His Phe
        1460            1465            1470

His Leu Pro Gln Leu Met Arg Asp Ile Gln Val Asn Leu Gly Tyr Leu
    1475            1480            1485

Cys Gln Ala Cys Thr Ser Leu Leu His Ser Arg Lys Met Leu Gln His
    1490            1495            1500

Tyr Leu Gln Asn Lys Asn Gly Asp Gly Leu Pro Ser Ala Val Ala Gln
1505            1510            1515            1520

Arg Val Gln Arg Pro Pro Ser Ala Ala Ser Ala Ala Pro Ser Ser Ser
            1525            1530            1535

Lys Gln Pro Ala Ala Asp Thr Glu Ala Ser Glu Gln Gln Ala Leu His
        1540            1545            1550

Thr Val Gln Tyr Gly Leu Leu Lys Ile Leu Ser Lys Thr Leu Ala Ala
    1555            1560            1565

Leu Arg His Phe Thr Pro Asp Val Cys Gln Ile Leu Leu Asp Gln Ser
    1570            1575            1580

Leu Asp Leu Ala Glu Tyr Asn Phe Leu Phe Ala Leu Ser Phe Thr Thr
1585            1590            1595            1600

Pro Thr Phe Asp Ser Glu Val Ala Pro Ser Phe Gly Thr Leu Leu Ala
            1605            1610            1615

Thr Val Asn Val Ala Leu Asn Met Leu Gly Glu Leu Asp Lys Lys Lys
        1620            1625            1630

Glu Pro Leu Thr Gln Ala Val Gly Leu Ser Thr Gln Ala Glu Gly Thr
    1635            1640            1645

Arg Thr Leu Lys Ser Leu Leu Met Phe Thr Met Glu Asn Cys Phe Tyr
    1650            1655            1660

Leu Leu Ile Ser Gln Ala Met Arg Tyr Leu Arg Asp Pro Ala Val His
1665            1670            1675            1680

Pro Arg Asp Lys Gln Arg Met Lys Gln Glu Leu Ser Ser Glu Leu Ser
            1685            1690            1695

Thr Leu Leu Ser Ser Leu Ser Arg Tyr Phe Arg Arg Gly Ala Pro Ser
        1700            1705            1710

Ser Pro Ala Thr Gly Val Leu Pro Ser Pro Gln Gly Lys Ser Thr Ser
    1715            1720            1725

Leu Ser Lys Ala Ser Pro Glu Ser Gln Glu Pro Leu Ile Gln Leu Val
    1730            1735            1740

Gln Ala Phe Val Arg His Met Gln Arg
1745            1750

<210> SEQ ID NO 15
<211> LENGTH: 1753
<212> TYPE: PRT
<213> ORGANISM: Homo sapiens

<400> SEQUENCE: 15
```

-continued

```
Met Ile Arg Lys Ser Lys Ile Thr Ser Val Leu Ser Phe Cys Arg Ser
 1               5                  10                  15

Ser Arg Glu Leu Trp Thr Ile Leu Leu Gly Arg Ser Ala Leu Arg Glu
             20                  25                  30

Leu Ser Gln Ile Glu Ala Glu Leu Asn Lys His Trp Arg Arg Leu Leu
             35                  40                  45

Glu Gly Leu Ser Tyr Tyr Lys Pro Pro Ser Pro Ser Ser Ala Glu Lys
 50                  55                  60

Val Lys Ala Asn Lys Asp Val Ala Ser Pro Leu Lys Glu Leu Gly Leu
 65                  70                  75                  80

Arg Ile Ser Lys Phe Leu Gly Leu Asp Glu Glu Gln Ser Val Gln Leu
                 85                  90                  95

Leu Gln Cys Tyr Leu Gln Glu Asp Tyr Arg Gly Thr Arg Asp Ser Val
             100                 105                 110

Lys Thr Val Leu Gln Asp Glu Arg Gln Ser Gln Ala Leu Ile Leu Lys
             115                 120                 125

Ile Ala Asp Tyr Tyr Glu Arg Thr Cys Ile Leu Arg Cys Val
             130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                 165                 170                 175

Tyr Arg Gln Gln Phe Glu Glu Leu Tyr Lys Thr Glu Ala Pro Thr Trp
             180                 185                 190

Glu Thr His Gly Asn Leu Met Thr Glu Arg Gln Val Ser Arg Trp Phe
             195                 200                 205

Val Gln Cys Leu Arg Glu Gln Ser Met Leu Leu Glu Ile Ile Phe Leu
210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                 245                 250                 255

Leu Val Asp Glu Thr Met Asp Pro Phe Val Asp Arg Ile Gly Tyr Phe
             260                 265                 270

Ser Ala Leu Ile Leu Val Glu Gly Met Asp Ile Glu Ser Leu His Lys
             275                 280                 285

Cys Ala Leu Asp Asp Arg Arg Glu Leu His Gln Phe Ala Gln Asp Gly
             290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                 325                 330                 335

Leu Asn Pro Glu Glu Thr Ser Ser Val Val Arg Lys Ile Gly Gly Thr
             340                 345                 350

Ala Ile Gln Leu Asn Val Phe Gln Tyr Leu Thr Arg Leu Leu Gln Ser
             355                 360                 365

Leu Ala Ser Gly Gly Asn Asp Cys Thr Thr Ser Thr Ala Cys Met Cys
             370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                 405                 410                 415

Asp Pro Ser Leu Pro Glu Leu Phe Trp Gly Thr Glu Pro Thr Ser Gly
```

-continued

```
                420                 425                 430
Leu Gly Ile Ile Leu Asp Ser Val Cys Gly Met Phe Pro His Leu Leu
            435                 440                 445
Ser Pro Leu Leu Gln Leu Leu Arg Ala Leu Val Ser Gly Lys Ser Thr
    450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
                485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
        515                 520                 525
Asp Arg Ala Tyr Leu Val Arg Trp Glu Tyr Ser Tyr Ser Ser Trp Thr
    530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
                565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
        595                 600                 605
Ser Pro Pro Val Asp Val Ile Ala Ser Cys Val Asn Cys Leu Thr Val
    610                 615                 620
Leu Ala Ala Arg Asn Pro Ala Lys Val Trp Thr Asp Leu Arg His Thr
625                 630                 635                 640
Gly Phe Leu Pro Phe Val Ala His Pro Val Ser Ser Leu Ser Gln Met
                645                 650                 655
Ile Ser Ala Glu Gly Met Asn Ala Gly Tyr Gly Asn Leu Leu Met
            660                 665                 670
Asn Ser Glu Gln Pro Gln Gly Glu Tyr Gly Val Thr Ile Ala Phe Leu
        675                 680                 685
Arg Leu Ile Thr Thr Leu Val Lys Gly Gln Leu Gly Ser Thr Gln Ser
    690                 695                 700
Gln Gly Leu Val Pro Cys Val Met Phe Val Leu Lys Glu Met Leu Pro
705                 710                 715                 720
Ser Tyr His Lys Trp Arg Tyr Asn Ser His Gly Val Arg Glu Gln Ile
                725                 730                 735
Gly Cys Leu Ile Leu Glu Leu Ile His Ala Ile Leu Asn Leu Cys His
            740                 745                 750
Glu Thr Asp Leu His Ser Ser His Thr Pro Ser Leu Gln Phe Leu Cys
        755                 760                 765
Ile Cys Ser Leu Ala Tyr Thr Glu Ala Gly Gln Thr Val Ile Asn Ile
    770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Gln Leu Leu Ile Lys
                805                 810                 815
Thr Val Lys Leu Ala Phe Ser Val Thr Asn Asn Val Ile Arg Leu Lys
            820                 825                 830
Pro Pro Ser Asn Val Val Ser Pro Leu Glu Gln Ala Leu Ser Gln His
        835                 840                 845
```

-continued

Gly Ala His Gly Asn Asn Leu Ile Ala Val Leu Ala Lys Tyr Ile Tyr
850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
            885                 890                 895

Asp Ala Ala Ala Ile Arg Asp Ala Phe Leu Thr Arg Leu Gln Ser Lys
            900                 905                 910

Ile Glu Asp Met Arg Ile Lys Val Met Ile Leu Glu Phe Leu Thr Val
            915                 920                 925

Ala Val Glu Thr Gln Pro Gly Leu Ile Glu Leu Phe Leu Asn Leu Glu
            930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
            965                 970                 975

Arg Tyr Trp Cys Pro Leu Leu His Arg Ala Ala Ile Ala Phe Leu
            980                 985                 990

His Ala Leu Trp Gln Asp Arg Arg Asp Ser Ala Met Leu Val Leu Arg
            995                 1000                1005

Thr Lys Pro Lys Phe Trp Glu Asn Leu Thr Ser Pro Leu Phe Gly Thr
    1010                1015                1020

Leu Ser Pro Pro Ser Glu Thr Ser Gly Pro Ser Ile Leu Glu Thr Cys
1025                1030                1035                1040

Ala Leu Ile Met Lys Ile Ile Cys Leu Glu Ile Tyr Tyr Val Val Lys
            1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Lys Ser Leu Ala Val
        1075                1080                1085

His Val Ala Glu Thr Glu Gly Ser Ser Cys Thr Ser Leu Leu Glu Tyr
    1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ser
            1140                1145                1150

Ser Val Asn Cys Leu Arg Leu Gly Ser Met Lys Cys Thr Leu Leu Leu
    1155                1160                1165

Ile Leu Leu Arg Gln Trp Lys Arg Glu Leu Gly Ser Val Asp Glu Ile
    1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

Val Leu Gln Met Lys Glu Met Lys Val Ser Asp Ile Pro Gln Tyr Ser
            1220                1225                1230

Gln Leu Val Leu Asn Val Cys Glu Thr Leu Gln Glu Glu Val Val Ala
            1235                1240                1245

Leu Phe Asp Gln Thr Arg His Ser Leu Ala Leu Gly Ser Ala Thr Glu
    1250                1255                1260

-continued

```
Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
            1300                1305                1310

Arg Leu Pro Ile Leu Pro Thr Leu Thr Thr Leu Glu Val Ser Leu
        1315                1320                1325

Arg Met Lys Gln Asn Leu His Phe Thr Glu Ala Thr Leu His Leu Leu
    1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
            1365                1370                1375

Ser Thr Asn Gly Thr Ala Gln Thr Pro Ser Ala Ser Arg Lys Ser Leu
            1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
    1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
            1445                1450                1455

Val Gly Phe Ile Leu Gln Leu Ser Asn Phe Met Lys Glu Trp His Phe
            1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Asp Thr Glu Ala Ser Glu Gln Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
            1620                1625                1630

Glu Pro Leu Thr Gln Ala Val Gly Leu Ser Thr Gln Ala Glu Gly Thr
        1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
```

```
                    1685              1690              1695
Thr Leu Leu Ser Ser Leu Ser Arg Tyr Phe Arg Arg Gly Ala Pro Ser
                1700              1705              1710
Ser Pro Ala Thr Gly Val Leu Pro Ser Pro Gln Gly Lys Ser Thr Ser
            1715              1720              1725
Leu Ser Lys Ala Ser Pro Glu Ser Gln Glu Pro Leu Ile Gln Leu Val
    1730              1735              1740
Gln Ala Phe Val Arg His Met Gln Arg
1745                1750

<210> SEQ ID NO 16
<211> LENGTH: 1753
<212> TYPE: PRT
<213> ORGANISM: Homo sapiens

<400> SEQUENCE: 16

Met Ile Arg Lys Ser Lys Ile Thr Ser Val Leu Ser Phe Cys Arg Ser
  1               5                  10                  15

Ser Arg Glu Leu Trp Thr Ile Leu Leu Gly Arg Ser Ala Leu Arg Glu
                20                  25                  30

Leu Ser Gln Ile Glu Ala Glu Leu Asn Lys His Trp Arg Arg Leu Leu
            35                  40                  45

Glu Gly Leu Ser Tyr Tyr Lys Pro Ser Pro Ser Ser Ala Glu Lys
        50                  55                  60

Val Lys Ala Asn Lys Asp Val Ala Ser Pro Leu Lys Glu Leu Gly Leu
 65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
                100                 105                 110

Lys Thr Val Leu Gln Asp Glu Arg Gln Ser Gln Ala Leu Ile Leu Lys
            115                 120                 125

Ile Ala Asp Tyr Tyr Tyr Glu Glu Arg Thr Cys Ile Leu Arg Cys Val
130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
                180                 185                 190

Glu Thr His Gly Asn Leu Met Thr Glu Arg Gln Val Ser Arg Trp Phe
            195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
    290                 295                 300
```

-continued

```
Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
    370                 375                 380

Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
            420                 425                 430

Leu Gly Ile Ile Leu Asp Ser Val Cys Gly Met Phe Pro His Leu Leu
        435                 440                 445

Ser Pro Leu Leu Gln Leu Leu Arg Ala Leu Val Ser Gly Lys Ser Thr
    450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
            500                 505                 510

Thr Asn Leu Arg Ile Pro Gln Gly Thr Val Gly Gln Val Met Leu Asp
        515                 520                 525

Asp Arg Ala Tyr Leu Val Arg Trp Glu Tyr Ser Tyr Ser Ser Trp Thr
    530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
            580                 585                 590

Ile Thr Ser Arg Ile Tyr Met Leu Leu Gln Arg Leu Thr Thr Val Ile
        595                 600                 605

Ser Pro Pro Val Asp Val Ile Ala Ser Cys Val Asn Cys Leu Thr Val
    610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Gly Tyr Gly Asn Leu Leu Met
            660                 665                 670

Asn Ser Glu Gln Pro Gln Gly Glu Tyr Gly Val Thr Ile Ala Phe Leu
        675                 680                 685

Arg Leu Ile Thr Thr Leu Val Lys Gly Gln Leu Gly Ser Thr Gln Ser
    690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
```

-continued

```
                725                 730                 735
Gly Cys Leu Ile Leu Glu Leu Ile His Ala Ile Leu Asn Leu Cys His
            740                 745                 750
Glu Thr Asp Leu His Ser Ser His Thr Pro Ser Leu Gln Phe Leu Cys
        755                 760                 765
Ile Cys Ser Leu Ala Tyr Thr Glu Ala Gly Gln Thr Val Ile Asn Ile
    770                 775                 780
Met Gly Ile Gly Val Asp Thr Ile Asp Met Val Met Ala Ala Gln Pro
785                 790                 795                 800
Arg Ser Asp Gly Ala Glu Gly Gln Gly Gln Gly Leu Leu Ile Lys
            805                 810                 815
Thr Val Lys Leu Ala Phe Ser Val Thr Asn Asn Val Ile Arg Leu Lys
        820                 825                 830
Pro Pro Ser Asn Val Val Ser Pro Leu Glu Gln Ala Leu Ser Gln His
    835                 840                 845
Gly Ala His Gly Asn Asn Leu Ile Ala Val Leu Ala Lys Tyr Ile Tyr
    850                 855                 860
His Lys His Asp Pro Ala Leu Pro Arg Leu Ala Ile Gln Leu Leu Lys
865                 870                 875                 880
Arg Leu Ala Thr Val Ala Pro Met Ser Val Tyr Ala Cys Leu Gly Asn
            885                 890                 895
Asp Ala Ala Ile Arg Asp Ala Phe Leu Thr Arg Leu Gln Ser Lys
            900                 905                 910
Ile Glu Asp Met Arg Ile Lys Val Met Ile Leu Glu Phe Leu Thr Val
        915                 920                 925
Ala Val Glu Thr Gln Pro Gly Leu Ile Glu Leu Phe Leu Asn Leu Glu
    930                 935                 940
Val Lys Asp Gly Ser Asp Gly Ser Lys Glu Phe Ser Leu Gly Met Trp
945                 950                 955                 960
Ser Cys Leu His Ala Val Leu Glu Leu Ile Asp Ser Gln Gln Gln Asp
            965                 970                 975
Arg Tyr Trp Cys Pro Pro Leu Leu His Arg Ala Ala Ile Ala Phe Leu
        980                 985                 990
His Ala Leu Trp Gln Asp Arg Arg Asp Ser Ala Met Leu Val Leu Arg
    995                 1000                1005
Thr Lys Pro Lys Phe Trp Glu Asn Leu Thr Ser Pro Leu Phe Gly Thr
    1010                1015                1020
Leu Ser Pro Pro Ser Glu Thr Ser Glu Pro Ser Ile Leu Glu Thr Cys
1025                1030                1035                1040
Ala Leu Ile Met Lys Ile Ile Cys Leu Glu Ile Tyr Tyr Val Val Lys
            1045                1050                1055
Gly Ser Leu Asp Gln Ser Leu Lys Asp Thr Leu Lys Lys Phe Ser Ile
        1060                1065                1070
Glu Lys Arg Phe Ala Tyr Trp Ser Gly Tyr Val Lys Ser Leu Ala Val
    1075                1080                1085
His Val Ala Glu Thr Glu Gly Ser Ser Cys Thr Ser Leu Leu Glu Tyr
    1090                1095                1100
Gln Met Leu Val Ser Ala Trp Arg Met Leu Leu Ile Ile Ala Thr Thr
1105                1110                1115                1120
His Ala Asp Ile Met His Leu Thr Asp Ser Val Val Arg Arg Gln Leu
            1125                1130                1135
Phe Leu Asp Val Leu Asp Gly Thr Lys Ala Leu Leu Leu Val Pro Ser
            1140                1145                1150
```

-continued

```
Ser Val Asn Cys Leu Arg Leu Gly Ser Met Lys Cys Thr Leu Leu Leu
        1155                1160                1165

Ile Leu Leu Arg Gln Trp Lys Arg Glu Leu Gly Ser Val Asp Glu Ile
        1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
                1205                1210                1215

Val Leu Gln Met Lys Glu Met Lys Val Ser Asp Ile Pro Gln Tyr Ser
        1220                1225                1230

Gln Leu Val Leu Asn Val Cys Glu Thr Leu Gln Glu Glu Val Ile Ala
        1235                1240                1245

Leu Phe Asp Gln Thr Arg His Ser Leu Ala Leu Gly Ser Ala Thr Glu
        1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
                1285                1290                1295

Leu Cys Glu Val Asp Glu Asp Gly Asp Ser Trp Leu Gln Val Thr Arg
                1300                1305                1310

Arg Leu Pro Ile Leu Pro Thr Leu Leu Thr Thr Leu Glu Val Ser Leu
        1315                1320                1325

Arg Met Arg Gln Asn Leu His Phe Thr Glu Ala Thr Leu His Leu Leu
        1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
                1365                1370                1375

Ser Thr Asn Gly Thr Ala Gln Thr Pro Ser Ala Ser Arg Lys Ser Leu
                1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
        1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
                1445                1450                1455

Val Gly Phe Ile Leu Gln Leu Ser Asn Phe Met Lys Glu Trp His Phe
                1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
        1490                1495                1500

Tyr Leu Gln Asn Lys Asn Gly Asp Gly Leu Pro Ser Ala Val Ala Gln
1505                1510                1515                1520

Arg Val Gln Arg Pro Ser Ala Ala Ser Ala Ala Pro Ser Ser Ser
                1525                1530                1535

Lys Gln Pro Ala Ala Asp Thr Glu Ala Ser Glu Gln Gln Ala Leu His
                1540                1545                1550

Thr Val Gln Tyr Gly Leu Leu Lys Ile Leu Ser Lys Thr Leu Ala Ala
        1555                1560                1565
```

```
Leu Arg His Phe Thr Pro Asp Val Cys Gln Ile Leu Leu Asp Gln Ser
    1570            1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
                1605                1610                1615

Thr Val Asn Val Ala Leu Asn Met Leu Gly Glu Leu Asp Lys Lys Lys
            1620                1625                1630

Glu Pro Leu Thr Gln Ala Val Gly Leu Ser Thr Gln Ala Glu Gly Thr
        1635                1640                1645

Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
                1685                1690                1695

Thr Leu Leu Ser Ser Leu Ser Arg Tyr Phe Arg Arg Gly Ala Pro Ser
            1700                1705                1710

Ser Pro Ala Thr Gly Val Leu Pro Ser Pro Gln Gly Lys Ser Thr Ser
        1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 17
<211> LENGTH: 1753
<212> TYPE: PRT
<213> ORGANISM: Homo sapiens

<400> SEQUENCE: 17

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu
65                  70                  75                  80

Arg Ile Ser Lys Phe Leu Gly Leu Asp Glu Glu Gln Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Glu Glu Arg Thr Cys Ile Leu Arg Cys Val
    130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Leu Val Ser Lys
                165                 170                 175

Tyr Arg Gln Gln Phe Glu Glu Leu Tyr Lys Thr Glu Ala Pro Thr Trp
            180                 185                 190
```

-continued

```
Glu Thr His Gly Asn Leu Met Thr Glu Arg Gln Val Ser Arg Trp Phe
            195                 200                 205
Val Gln Cys Leu Arg Glu Gln Ser Met Leu Leu Glu Ile Ile Phe Leu
            210                 215                 220
Tyr Tyr Ala Tyr Phe Glu Met Ala Pro Ser Asp Leu Leu Val Leu Thr
225                 230                 235                 240
Lys Met Phe Lys Glu Gln Gly Phe Gly Ser Arg Gln Thr Asn Arg His
            245                 250                 255
Leu Val Asp Glu Thr Met Asp Pro Phe Val Asp Arg Ile Gly Tyr Phe
            260                 265                 270
Ser Ala Leu Ile Leu Val Glu Gly Met Asp Ile Glu Ser Leu His Lys
            275                 280                 285
Cys Ala Leu Asp Asp Arg Arg Glu Leu His Gln Phe Ala Gln Asp Gly
            290                 295                 300
Leu Ile Cys Gln Asp Met Asp Cys Leu Met Leu Thr Phe Gly Asp Ile
305                 310                 315                 320
Pro His His Ala Pro Val Leu Leu Ala Trp Ala Leu Leu Arg His Thr
            325                 330                 335
Leu Asn Pro Glu Glu Thr Ser Ser Val Val Arg Lys Ile Gly Gly Thr
            340                 345                 350
Ala Ile Gln Leu Asn Val Phe Gln Tyr Leu Thr Arg Leu Leu Gln Ser
            355                 360                 365
Leu Ala Ser Gly Gly Asn Asp Cys Thr Thr Ser Thr Ala Cys Met Cys
            370                 375                 380
Val Tyr Gly Leu Leu Ser Phe Val Leu Thr Ser Leu Glu Leu His Thr
385                 390                 395                 400
Leu Gly Asn Gln Gln Asp Ile Ile Asp Thr Ala Cys Glu Val Leu Ala
            405                 410                 415
Asp Pro Ser Leu Pro Glu Leu Phe Trp Gly Thr Glu Pro Thr Ser Gly
            420                 425                 430
Leu Gly Ile Ile Leu Asp Ser Val Cys Gly Met Phe Pro His Leu Leu
            435                 440                 445
Ser Pro Leu Leu Gln Leu Leu Arg Ala Leu Val Ser Gly Lys Ser Thr
            450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
            485                 490                 495
Leu Trp Arg Arg Gln Thr Pro Lys Leu Leu Tyr Pro Leu Gly Gly Gln
            500                 505                 510
Thr Asn Leu Arg Ile Pro Gln Gly Thr Val Gly Gln Val Met Leu Asp
            515                 520                 525
Asp Arg Ala Tyr Leu Val Arg Trp Glu Tyr Ser Tyr Ser Ser Trp Thr
            530                 535                 540
Leu Phe Thr Cys Glu Ile Glu Met Leu Leu His Val Val Ser Thr Ala
545                 550                 555                 560
Asp Val Ile Gln His Cys Gln Arg Val Lys Pro Ile Ile Asp Leu Val
            565                 570                 575
His Lys Val Ile Ser Thr Asp Leu Ser Ile Ala Asp Cys Leu Leu Pro
            580                 585                 590
Ile Thr Ser Arg Ile Tyr Met Leu Leu Gln Arg Leu Thr Thr Val Ile
            595                 600                 605
```

-continued

```
Ser Pro Pro Val Asp Val Ile Ala Ser Cys Val Asn Cys Leu Thr Val
610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Gly Tyr Gly Asn Leu Leu Met
                660                 665                 670

Asn Ser Glu Gln Pro Gln Gly Glu Tyr Gly Val Thr Ile Ala Phe Leu
            675                 680                 685

Arg Leu Ile Thr Thr Leu Val Lys Gly Gln Leu Gly Ser Thr Gln Ser
690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
                740                 745                 750

Glu Thr Asp Leu His Ser Ser His Thr Pro Ser Leu Gln Phe Leu Cys
            755                 760                 765

Ile Cys Ser Leu Ala Tyr Thr Glu Ala Gly Gln Thr Val Ile Asn Ile
770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Leu Leu Ile Lys
                805                 810                 815

Thr Val Lys Leu Ala Phe Ser Val Thr Asn Asn Val Ile Arg Leu Lys
                820                 825                 830

Pro Pro Ser Asn Val Val Ser Pro Leu Glu Gln Ala Leu Ser Gln His
            835                 840                 845

Gly Ala His Gly Asn Asn Leu Ile Ala Val Leu Ala Lys Tyr Ile Tyr
850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ile Arg Asp Ala Phe Leu Thr Arg Leu Gln Ser Lys
                900                 905                 910

Ile Glu Asp Met Arg Ile Lys Val Met Ile Leu Glu Phe Leu Thr Val
            915                 920                 925

Ala Val Glu Thr Gln Pro Gly Leu Ile Glu Leu Phe Leu Asn Leu Glu
930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Asp
                965                 970                 975

Arg Tyr Trp Cys Pro Pro Leu Leu His Arg Ala Ile Ala Phe Leu
                980                 985                 990

His Ala Leu Trp Gln Asp Arg Arg Asp Ser Ala Met Leu Val Leu Arg
            995                 1000                1005

Thr Lys Pro Lys Phe Trp Glu Asn Leu Thr Ser Pro Leu Phe Gly Thr
    1010                1015                1020

Leu Ser Pro Pro Ser Glu Thr Ser Glu Pro Ser Ile Leu Glu Thr Cys
```

-continued

```
             1025               1030               1035               1040
Ala Leu Ile Met Lys Ile Ile Cys Leu Glu Ile Tyr Tyr Val Val Lys
             1045               1050               1055

Gly Ser Leu Asp Gln Ser Leu Lys Asp Thr Leu Lys Lys Phe Ser Ile
             1060               1065               1070

Glu Lys Arg Phe Ala Tyr Trp Ser Gly Tyr Val Lys Ser Leu Ala Val
             1075               1080               1085

His Val Ala Glu Thr Glu Gly Ser Ser Cys Thr Ser Leu Leu Glu Tyr
             1090               1095               1100

Gln Met Leu Val Ser Ala Trp Arg Met Leu Leu Ile Ile Ala Thr Thr
1105                1110               1115               1120

His Ala Asp Ile Met His Leu Thr Asp Ser Val Val Arg Arg Gln Leu
             1125               1130               1135

Phe Leu Asp Val Leu Asp Gly Thr Lys Ala Leu Leu Leu Val Pro Ser
             1140               1145               1150

Ser Val Asn Cys Leu Arg Leu Gly Ser Met Lys Cys Thr Leu Leu Leu
             1155               1160               1165

Ile Leu Leu Arg Gln Trp Lys Arg Glu Leu Gly Ser Val Asp Glu Ile
             1170               1175               1180

Leu Gly Pro Leu Thr Glu Ile Leu Glu Gly Val Leu Gln Ala Asp Gln
1185                1190               1195               1200

Gln Leu Met Glu Lys Thr Lys Ala Lys Val Phe Ser Ala Phe Ile Thr
             1205               1210               1215

Val Leu Gln Met Lys Glu Met Lys Val Ser Asp Ile Pro Gln Tyr Ser
             1220               1225               1230

Gln Leu Val Leu Asn Val Cys Glu Thr Leu Gln Glu Glu Val Ile Ala
             1235               1240               1245

Leu Phe Asp Gln Thr Arg His Ser Leu Ala Leu Gly Ser Ala Thr Glu
             1250               1255               1260

Asp Lys Asp Ser Met Glu Thr Asp Asp Cys Ser Arg Ser Arg His Arg
1265                1270               1275               1280

Asp Gln Arg Asp Gly Val Cys Val Leu Gly Leu His Leu Ala Lys Glu
             1285               1290               1295

Leu Cys Glu Val Asp Glu Asp Gly Asp Ser Trp Leu Gln Val Thr Arg
             1300               1305               1310

Arg Leu Pro Ile Leu Pro Thr Leu Leu Thr Thr Leu Glu Val Ser Leu
             1315               1320               1325

Arg Met Lys Gln Asn Leu His Phe Thr Glu Ala Thr Leu His Leu Leu
             1330               1335               1340

Leu Thr Leu Ala Arg Thr Gln Gln Gly Ala Thr Ala Val Ala Gly Ala
1345                1350               1355               1360

Gly Ile Thr Gln Ser Ile Cys Leu Pro Leu Leu Ser Val Tyr Gln Leu
             1365               1370               1375

Ser Thr Asn Gly Thr Ala Gln Thr Pro Ser Ala Ser Arg Lys Ser Leu
             1380               1385               1390

Asp Ala Pro Ser Trp Pro Gly Val Tyr Arg Leu Ser Met Ser Leu Met
             1395               1400               1405

Glu Gln Leu Leu Lys Thr Leu Arg Tyr Asn Phe Leu Pro Glu Ala Leu
             1410               1415               1420

Asp Phe Val Gly Val His Gln Glu Arg Thr Leu Gln Cys Leu Asn Ala
1425                1430               1435               1440

Val Arg Thr Val Gln Ser Leu Ala Tyr Leu Glu Glu Ala Asp His Thr
             1445               1450               1455
```

-continued

Val Gly Phe Ile Leu Gln Leu Ser Asn Phe Met Lys Glu Trp His Phe
            1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
    1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Asp Thr Glu Ala Ser Glu Gln Gln Ala Leu His
        1540                1545                1550

Thr Val Gln Tyr Gly Leu Leu Lys Ile Leu Ser Lys Thr Leu Ala Ala
    1555                1560                1565

Leu Arg His Phe Thr Pro Asp Val Cys Gln Ile Leu Leu Asp Gln Ser
1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
    1635                1640                1645

Arg Thr Leu Lys Ser Leu Leu Met Phe Thr Met Glu Asn Cys Phe Tyr
1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
            1685                1690                1695

Thr Leu Leu Ser Ser Leu Ser Arg Tyr Phe Arg Arg Gly Ala Pro Ser
        1700                1705                1710

Ser Pro Ala Thr Gly Val Leu Pro Ser Pro Gln Gly Lys Ser Thr Ser
    1715                1720                1725

Leu Ser Lys Ala Ser Pro Glu Ser Gln Glu Pro Leu Ile Gln Leu Val
1730                1735                1740

Gln Ala Phe Val Arg His Met Gln Arg
1745                1750

<210> SEQ ID NO 18
<211> LENGTH: 1753
<212> TYPE: PRT
<213> ORGANISM: Homo sapiens

<400> SEQUENCE: 18

Met Ile Arg Lys Ser Lys Ile Thr Ser Val Leu Ser Phe Cys Arg Ser
1               5                   10                  15

Ser Arg Glu Leu Trp Thr Ile Leu Leu Gly Arg Ser Ala Leu Arg Glu
            20                  25                  30

Leu Ser Gln Ile Glu Ala Glu Leu Asn Lys His Trp Arg Arg Leu Leu
        35                  40                  45

Glu Gly Leu Ser Tyr Tyr Lys Pro Pro Ser Pro Ser Ser Ala Glu Lys
    50                  55                  60

Val Lys Ala Asn Lys Asp Val Ala Ser Pro Leu Lys Glu Leu Gly Leu

-continued

```
            65                  70                  75                  80
Arg Ile Ser Lys Phe Leu Gly Leu Asp Glu Glu Gln Ser Val Gln Leu
                    85                  90                  95
Leu Gln Cys Tyr Leu Gln Glu Asp Tyr Arg Gly Thr Arg Asp Ser Val
                100                 105                 110
Lys Thr Val Leu Gln Asp Glu Arg Gln Ser Gln Ala Leu Ile Leu Lys
                115                 120                 125
Ile Ala Asp Tyr Tyr Glu Glu Arg Thr Cys Ile Leu Arg Cys Val
130                 135                 140
Leu His Leu Leu Thr Tyr Phe Gln Asp Glu Arg His Pro Tyr Arg Val
145                 150                 155                 160
Glu Tyr Ala Asp Cys Val Asp Lys Leu Glu Lys Glu Leu Val Ser Lys
                165                 170                 175
Tyr Arg Gln Gln Phe Glu Glu Leu Tyr Lys Thr Glu Ala Pro Thr Trp
                180                 185                 190
Glu Thr His Gly Asn Leu Met Thr Glu Arg Gln Val Ser Arg Trp Phe
                195                 200                 205
Val Gln Cys Leu Arg Glu Gln Ser Met Leu Leu Glu Ile Ile Phe Leu
210                 215                 220
Tyr Tyr Ala Tyr Phe Glu Met Ala Pro Ser Asp Leu Leu Val Leu Thr
225                 230                 235                 240
Lys Met Phe Lys Glu Gln Gly Phe Gly Ser Arg Gln Thr Asn Arg His
                245                 250                 255
Leu Val Asp Glu Thr Met Asp Pro Phe Val Asp Arg Ile Gly Tyr Phe
                260                 265                 270
Ser Ala Leu Ile Leu Val Glu Gly Met Asp Ile Glu Ser Leu His Lys
                275                 280                 285
Cys Ala Leu Asp Asp Arg Arg Glu Leu His Gln Phe Ala Gln Asp Gly
                290                 295                 300
Leu Ile Cys Gln Asp Met Asp Cys Leu Met Leu Thr Phe Gly Asp Ile
305                 310                 315                 320
Pro His His Ala Pro Val Leu Leu Ala Trp Ala Leu Leu Arg His Thr
                325                 330                 335
Leu Asn Pro Glu Glu Thr Ser Ser Val Val Arg Lys Ile Gly Gly Thr
                340                 345                 350
Ala Ile Gln Leu Asn Val Phe Gln Tyr Leu Thr Arg Leu Leu Gln Ser
                355                 360                 365
Leu Ala Ser Gly Gly Asn Asp Cys Thr Thr Ser Thr Ala Cys Met Cys
                370                 375                 380
Val Tyr Gly Leu Leu Ser Phe Val Leu Thr Ser Leu Glu Leu His Thr
385                 390                 395                 400
Leu Gly Asn Gln Gln Asp Ile Ile Asp Thr Ala Cys Glu Val Leu Ala
                405                 410                 415
Asp Pro Ser Leu Pro Glu Leu Phe Trp Gly Thr Glu Pro Thr Ser Gly
                420                 425                 430
Leu Gly Ile Ile Leu Asp Ser Val Cys Gly Met Phe Pro His Leu Leu
                435                 440                 445
Ser Pro Leu Leu Gln Leu Leu Arg Ala Leu Val Ser Gly Lys Ser Thr
450                 455                 460
Ala Lys Lys Val Tyr Ser Phe Leu Asp Lys Met Ser Phe Tyr Asn Glu
465                 470                 475                 480
Leu Tyr Lys His Lys Pro His Asp Val Ile Ser His Glu Asp Gly Thr
                485                 490                 495
```

-continued

```
Leu Trp Arg Arg Gln Thr Pro Lys Leu Leu Tyr Pro Leu Gly Gly Gln
            500                 505                 510

Thr Asn Leu Arg Ile Pro Gln Gly Thr Val Gly Gln Val Met Leu Asp
        515                 520                 525

Asp Arg Ala Tyr Leu Val Arg Trp Glu Tyr Ser Tyr Ser Ser Trp Thr
    530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
            580                 585                 590

Ile Thr Ser Arg Ile Tyr Met Leu Leu Gln Arg Leu Thr Thr Val Ile
        595                 600                 605

Ser Pro Pro Val Asp Val Ile Ala Ser Cys Val Asn Cys Leu Thr Val
    610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Tyr Gly Asn Leu Leu Met
            660                 665                 670

Asn Ser Glu Gln Pro Gln Gly Glu Tyr Gly Val Thr Ile Ala Phe Leu
        675                 680                 685

Arg Leu Ile Thr Thr Leu Val Lys Gly Gln Leu Gly Ser Thr Gln Ser
    690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
            740                 745                 750

Glu Thr Asp Leu His Ser Ser His Thr Pro Ser Leu Gln Phe Leu Cys
        755                 760                 765

Ile Cys Ser Leu Ala Tyr Thr Glu Ala Gly Gln Thr Val Ile Asn Ile
    770                 775                 780

Met Gly Ile Gly Val Asp Thr Ile Asp Met Val Met Ala Ala Gln Pro
785                 790                 795                 800

Arg Ser Asp Gly Ala Glu Gly Gln Gly Gln Gly Leu Leu Ile Lys
                805                 810                 815

Thr Val Lys Leu Ala Phe Ser Val Thr Asn Asn Val Ile Arg Leu Lys
            820                 825                 830

Pro Pro Ser Asn Val Val Ser Pro Leu Glu Gln Ala Leu Ser Gln His
        835                 840                 845

Gly Ala His Gly Asn Asn Leu Ile Ala Val Leu Ala Lys Tyr Ile Tyr
    850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
                885                 890                 895

Asp Ala Ala Ala Ile Arg Asp Ala Phe Leu Thr Arg Leu Gln Ser Lys
            900                 905                 910
```

```
Ile Glu Asp Met Arg Ile Lys Val Met Ile Leu Glu Phe Leu Thr Val
        915                 920                 925

Ala Val Glu Thr Gln Pro Gly Leu Ile Glu Leu Phe Leu Asn Leu Glu
        930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
                965                 970                 975

Arg Tyr Trp Cys Pro Pro Leu Leu His Arg Ala Ala Ile Ala Phe Leu
            980                 985                 990

His Ala Leu Trp Gln Asp Arg Arg Asp Ser Ala Met Leu Val Leu Arg
        995                1000                1005

Thr Lys Pro Lys Phe Trp Glu Asn Leu Thr Ser Pro Leu Phe Gly Thr
    1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
                1045                1050                1055

Gly Ser Leu Asp Gln Ser Leu Lys Asp Thr Leu Lys Lys Phe Ser Ile
            1060                1065                1070

Glu Lys Arg Phe Ala Tyr Trp Ser Gly Tyr Val Lys Ser Leu Ala Val
        1075                1080                1085

His Val Ala Glu Thr Glu Gly Ser Ser Cys Thr Ser Leu Leu Glu Tyr
        1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
                1125                1130                1135

Phe Leu Asp Val Leu Asp Gly Thr Lys Ala Leu Leu Leu Val Pro Ser
            1140                1145                1150

Ser Val Asn Cys Leu Arg Leu Gly Ser Met Lys Cys Thr Leu Leu Leu
        1155                1160                1165

Ile Leu Leu Arg Gln Trp Lys Arg Glu Leu Gly Ser Val Asp Glu Ile
    1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
                1205                1210                1215

Val Leu Gln Met Lys Glu Met Lys Val Ser Asp Ile Pro Gln Tyr Ser
            1220                1225                1230

Gln Leu Val Leu Asn Val Cys Glu Thr Leu Gln Glu Glu Val Ile Ala
        1235                1240                1245

Leu Phe Asp Gln Thr Arg His Ser Leu Ala Leu Gly Ser Ala Thr Glu
    1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
                1285                1290                1295

Leu Cys Glu Val Asp Glu Asp Gly Asp Ser Trp Leu Gln Val Thr Arg
            1300                1305                1310

Arg Leu Pro Ile Leu Pro Thr Leu Leu Thr Thr Leu Glu Val Ser Leu
        1315                1320                1325

Arg Met Lys Gln Asn Leu His Phe Thr Glu Ala Thr Leu His Leu Leu
```

-continued

```
                1330                1335                1340
Leu Thr Leu Ala Arg Thr Gln Gln Gly Ala Thr Ala Val Ala Gly Ala
1345                1350                1355                1360
Gly Ile Thr Gln Ser Ile Cys Leu Pro Leu Leu Ser Val Tyr Gln Leu
                1365                1370                1375
Ser Thr Asn Gly Thr Ala Gln Thr Pro Ser Ala Ser Arg Lys Ser Leu
                1380                1385                1390
Asp Ala Pro Ser Trp Pro Gly Val Tyr Arg Leu Ser Met Ser Leu Met
                1395                1400                1405
Glu Gln Leu Leu Lys Thr Leu Arg Tyr Asn Phe Leu Pro Glu Ala Leu
                1410                1415                1420
Asp Phe Val Gly Val His Gln Glu Arg Thr Leu Gln Cys Leu Asn Ala
1425                1430                1435                1440
Val Arg Thr Val Gln Ser Leu Ala Cys Leu Glu Glu Ala Asp His Thr
                1445                1450                1455
Val Gly Phe Ile Leu Gln Leu Ser Asn Phe Met Lys Glu Trp His Phe
                1460                1465                1470
His Leu Pro Gln Leu Met Arg Asp Ile Gln Val Asn Leu Gly Tyr Leu
                1475                1480                1485
Cys Gln Ala Cys Thr Ser Leu Leu His Ser Arg Lys Met Leu Gln His
                1490                1495                1500
Tyr Leu Gln Asn Lys Asn Gly Asp Gly Leu Pro Ser Ala Val Ala Gln
1505                1510                1515                1520
Arg Val Gln Arg Pro Pro Ser Ala Ala Ser Ala Ala Pro Ser Ser Ser
                1525                1530                1535
Lys Gln Pro Ala Ala Gln Thr Glu Ala Ser Glu Gln Gln Ala Leu His
                1540                1545                1550
Thr Val Gln Tyr Gly Leu Leu Lys Ile Leu Ser Lys Thr Leu Ala Ala
                1555                1560                1565
Leu Arg His Phe Thr Pro Asp Val Cys Gln Ile Leu Leu Asp Gln Ser
                1570                1575                1580
Leu Asp Leu Ala Glu Tyr Asn Phe Leu Phe Ala Leu Ser Phe Thr Thr
1585                1590                1595                1600
Pro Thr Phe Asp Ser Glu Val Ala Pro Ser Phe Gly Thr Leu Leu Ala
                1605                1610                1615
Thr Val Asn Val Ala Leu Asn Met Leu Gly Glu Leu Asp Lys Lys Lys
                1620                1625                1630
Glu Pro Leu Thr Gln Ala Val Gly Leu Ser Thr Gln Ala Glu Gly Thr
                1635                1640                1645
Arg Thr Leu Lys Ser Leu Leu Met Phe Thr Met Glu Asn Cys Phe Tyr
                1650                1655                1660
Leu Leu Ile Ser Gln Ala Met Arg Tyr Leu Arg Asp Pro Ala Val His
1665                1670                1675                1680
Pro Arg Asp Lys Gln Arg Met Lys Gln Glu Leu Ser Ser Glu Leu Ser
                1685                1690                1695
Thr Leu Leu Ser Ser Leu Ser Arg Tyr Phe Arg Arg Gly Ala Pro Ser
                1700                1705                1710
Ser Pro Ala Thr Gly Val Leu Pro Ser Pro Gln Gly Lys Ser Thr Ser
                1715                1720                1725
Leu Ser Lys Ala Ser Pro Glu Ser Gln Glu Pro Leu Ile Gln Leu Val
                1730                1735                1740
Gln Ala Phe Val Arg His Met Gln Arg
1745                1750
```

<210> SEQ ID NO 19
<211> LENGTH: 1753
<212> TYPE: PRT
<213> ORGANISM: Homo sapiens

<400> SEQUENCE: 19

```
Met Ile Arg Lys Ser Lys Ile Thr Ser Val Leu Ser Phe Cys Arg Ser
 1               5                  10                  15

Ser Arg Glu Leu Trp Thr Ile Leu Leu Gly Arg Ser Ala Leu Arg Glu
                20                  25                  30

Leu Ser Gln Ile Glu Ala Glu Leu Asn Lys His Trp Arg Arg Leu Leu
            35                  40                  45

Glu Gly Leu Ser Tyr Tyr Lys Pro Pro Ser Ser Ala Glu Lys
    50                  55                  60

Val Lys Ala Asn Lys Asp Val Ala Ser Pro Lys Glu Leu Gly Leu
 65                  70                  75                  80

Arg Ile Ser Lys Phe Leu Gly Leu Asp Glu Glu Ser Val Gln Leu
                85                  90                  95

Leu Gln Cys Tyr Leu Gln Glu Asp Tyr Arg Gly Thr Arg Asp Ser Val
            100                 105                 110

Lys Thr Val Leu Gln Asp Glu Arg Gln Ser Gln Ala Leu Ile Leu Lys
        115                 120                 125

Ile Ala Asp Tyr Tyr Glu Glu Arg Thr Cys Ile Leu Arg Cys Val
130                 135                 140

Leu His Leu Leu Thr Tyr Phe Gln Asp Glu Arg His Pro Tyr Arg Val
145                 150                 155                 160

Glu Tyr Ala Asp Cys Val Asp Lys Leu Glu Lys Glu Leu Val Ser Lys
                165                 170                 175

Tyr Arg Gln Gln Phe Glu Glu Leu Tyr Lys Thr Glu Ala Pro Thr Trp
            180                 185                 190

Glu Thr His Gly Asn Leu Met Thr Glu Arg Gln Val Ser Arg Trp Phe
        195                 200                 205

Val Gln Cys Leu Arg Glu Gln Ser Met Leu Leu Glu Ile Ile Phe Leu
    210                 215                 220

Tyr Tyr Ala Tyr Phe Glu Met Ala Pro Ser Asp Leu Leu Val Leu Thr
225                 230                 235                 240

Lys Met Phe Lys Glu Gln Gly Phe Gly Ser Arg Gln Thr Asn Arg His
                245                 250                 255

Leu Val Asp Glu Thr Met Asp Pro Phe Val Asp Arg Ile Gly Tyr Phe
            260                 265                 270

Ser Ala Leu Ile Leu Val Glu Gly Met Asp Ile Glu Ser Leu His Lys
        275                 280                 285

Cys Ala Leu Asp Asp Arg Arg Glu Leu His Gln Phe Ala Gln Asp Gly
    290                 295                 300

Leu Ile Cys Gln Asp Met Asp Cys Leu Met Leu Thr Phe Gly Asp Ile
305                 310                 315                 320

Pro His His Ala Pro Val Leu Leu Ala Trp Ala Leu Leu Arg His Thr
                325                 330                 335

Leu Asn Pro Glu Glu Thr Ser Ser Val Val Arg Lys Ile Gly Gly Thr
            340                 345                 350

Ala Ile Gln Leu Asn Val Phe Gln Tyr Leu Thr Arg Leu Leu Gln Ser
        355                 360                 365

Leu Ala Ser Gly Gly Asn Asp Cys Thr Thr Ser Thr Ala Cys Met Cys
```

-continued

```
                370                 375                 380
Val Tyr Gly Leu Leu Ser Phe Val Leu Thr Ser Leu Glu Leu His Thr
385                 390                 395                 400

Leu Gly Asn Gln Gln Asp Ile Ile Asp Thr Ala Cys Glu Val Leu Ala
                405                 410                 415

Asp Pro Ser Leu Pro Glu Leu Phe Trp Gly Thr Glu Pro Thr Ser Gly
                420                 425                 430

Leu Gly Ile Ile Leu Asp Ser Val Cys Gly Met Phe Pro His Leu Leu
                435                 440                 445

Ser Pro Leu Leu Gln Leu Leu Arg Ala Leu Val Ser Gly Lys Ser Thr
450                 455                 460

Ala Lys Lys Val Tyr Ser Phe Leu Asp Lys Met Ser Phe Tyr Asn Glu
465                 470                 475                 480

Leu Tyr Lys His Lys Pro His Asp Val Ile Ser His Glu Asp Gly Thr
                485                 490                 495

Leu Trp Arg Arg Gln Thr Pro Lys Leu Leu Tyr Pro Leu Gly Gly Gln
                500                 505                 510

Thr Asn Leu Arg Ile Pro Gln Gly Thr Val Gly Gln Val Met Leu Asp
                515                 520                 525

Asp Arg Ala Tyr Leu Val Arg Trp Glu Tyr Ser Tyr Ser Ser Trp Thr
530                 535                 540

Leu Phe Thr Cys Glu Ile Glu Met Leu Leu His Val Val Ser Thr Ala
545                 550                 555                 560

Asp Val Ile Gln His Cys Gln Arg Val Lys Pro Ile Ile Asp Leu Val
                565                 570                 575

His Lys Val Ile Ser Thr Asp Leu Ser Ile Ala Asp Cys Leu Leu Pro
                580                 585                 590

Ile Thr Ser Arg Ile Tyr Met Leu Leu Gln Arg Leu Thr Thr Val Ile
                595                 600                 605

Ser Pro Pro Val Asp Val Ile Ala Ser Cys Val Asn Cys Leu Thr Val
                610                 615                 620

Leu Ala Ala Arg Asn Pro Ala Lys Val Trp Thr Asp Leu Arg His Thr
625                 630                 635                 640

Gly Phe Leu Pro Phe Val Ala His Pro Val Ser Ser Leu Ser Gln Met
                645                 650                 655

Ile Ser Ala Glu Gly Met Asn Ala Gly Tyr Gly Asn Leu Leu Met
                660                 665                 670

Asn Ser Glu Gln Pro Gln Gly Glu Tyr Gly Val Thr Ile Ala Phe Leu
                675                 680                 685

Arg Leu Ile Thr Thr Leu Val Lys Gly Gln Leu Gly Ser Thr Gln Ser
                690                 695                 700

Gln Gly Leu Val Pro Cys Val Met Phe Val Leu Lys Glu Met Leu Pro
705                 710                 715                 720

Ser Tyr His Lys Trp Arg Tyr Asn Ser His Gly Val Arg Glu Gln Ile
                725                 730                 735

Gly Cys Leu Ile Leu Glu Leu Ile His Ala Ile Leu Asn Leu Cys His
                740                 745                 750

Glu Thr Asp Leu His Ser Ser His Thr Pro Ser Leu Gln Phe Leu Cys
                755                 760                 765

Ile Cys Ser Leu Ala Tyr Thr Glu Ala Gly Gln Thr Val Ile Asn Ile
                770                 775                 780

Met Gly Ile Gly Val Asp Thr Ile Asp Met Val Met Ala Ala Gln Pro
785                 790                 795                 800
```

-continued

Arg Ser Asp Gly Ala Glu Gly Gln Gly Gln Gly Gln Leu Leu Ile Lys
            805                 810                 815

Thr Val Lys Leu Ala Phe Ser Val Thr Asn Asn Val Ile Arg Leu Lys
        820                 825                 830

Pro Pro Ser Asn Val Val Ser Pro Leu Glu Gln Ala Leu Ser Gln His
        835                 840                 845

Gly Ala His Gly Asn Asn Leu Ile Ala Val Leu Ala Lys Tyr Ile Tyr
    850                 855                 860

His Lys His Asp Pro Ala Leu Pro Arg Leu Ala Ile Gln Leu Leu Lys
865                 870                 875                 880

Arg Leu Ala Thr Val Ala Pro Met Ser Val Tyr Ala Cys Leu Gly Asn
            885                 890                 895

Asp Ala Ala Ala Ile Arg Asp Ala Phe Leu Thr Arg Leu Gln Ser Lys
                900                 905                 910

Ile Glu Asp Met Arg Ile Lys Val Met Ile Leu Glu Phe Leu Thr Val
            915                 920                 925

Ala Val Glu Thr Gln Pro Gly Leu Ile Glu Leu Phe Leu Asn Leu Glu
    930                 935                 940

Val Lys Asp Gly Ser Asp Gly Ser Lys Glu Phe Ser Leu Gly Met Trp
945                 950                 955                 960

Ser Cys Leu His Ala Val Leu Glu Leu Ile Asp Ser Gln Gln Gln Asp
            965                 970                 975

Arg Tyr Trp Cys Pro Pro Leu Leu His Arg Ala Ala Ile Ala Phe Leu
                980                 985                 990

His Ala Leu Trp Gln Asp Arg Arg Asp Ser Ala Met Leu Val Leu Arg
            995                 1000                1005

Thr Lys Pro Lys Phe Trp Glu Asn Leu Thr Ser Pro Leu Phe Gly Thr
    1010                1015                1020

Leu Ser Pro Pro Ser Glu Thr Ser Glu Pro Ser Ile Leu Glu Thr Cys
1025                1030                1035                1040

Ala Leu Ile Met Lys Ile Ile Cys Leu Glu Ile Tyr Tyr Val Val Lys
            1045                1050                1055

Gly Ser Leu Asp Gln Ser Leu Lys Asp Thr Leu Lys Lys Phe Ser Ile
                1060                1065                1070

Glu Lys Arg Phe Ala Tyr Trp Ser Gly Tyr Val Lys Ser Leu Ala Val
        1075                1080                1085

His Val Ala Glu Thr Glu Gly Ser Ser Cys Thr Ser Leu Leu Glu Tyr
    1090                1095                1100

Gln Met Leu Val Ser Ala Trp Arg Met Leu Leu Ile Ile Ala Thr Thr
1105                1110                1115                1120

His Ala Asp Ile Met His Leu Thr Asp Ser Val Val Arg Arg Gln Leu
            1125                1130                1135

Phe Leu Asp Val Leu Asp Gly Thr Lys Ala Leu Leu Leu Val Pro Ser
                1140                1145                1150

Ser Val Asn Cys Leu Arg Leu Gly Ser Met Lys Cys Thr Leu Leu Leu
    1155                1160                1165

Ile Leu Leu Arg Gln Trp Lys Arg Glu Leu Gly Ser Val Asp Glu Ile
    1170                1175                1180

Leu Gly Pro Leu Thr Glu Ile Leu Glu Gly Val Leu Gln Ala Asp Gln
1185                1190                1195                1200

Gln Leu Met Glu Lys Thr Lys Ala Lys Val Phe Ser Ala Phe Ile Thr
            1205                1210                1215

-continued

```
Val Leu Gln Met Lys Glu Met Lys Val Ser Asp Ile Pro Gln Tyr Ser
        1220                1225                1230

Gln Leu Val Leu Asn Val Cys Glu Thr Leu Gln Glu Glu Val Ile Ala
        1235                1240                1245

Leu Phe Asp Gln Thr Arg His Ser Leu Ala Leu Gly Ser Ala Thr Glu
        1250                1255                1260

Asp Lys Asp Ser Met Glu Thr Asp Asp Cys Ser Arg Ser Arg His Arg
1265                1270                1275                1280

Asp Gln Arg Asp Gly Val Cys Val Leu Gly Leu His Leu Ala Lys Glu
            1285                1290                1295

Leu Cys Glu Val Asp Glu Asp Gly Asp Ser Trp Leu Gln Val Thr Arg
        1300                1305                1310

Arg Leu Pro Ile Leu Pro Thr Leu Leu Thr Thr Leu Glu Val Ser Leu
        1315                1320                1325

Arg Met Lys Gln Asn Leu His Phe Thr Glu Ala Thr Leu His Leu Leu
        1330                1335                1340

Leu Thr Leu Ala Arg Thr Gln Gln Gly Ala Thr Ala Val Ala Gly Ala
1345                1350                1355                1360

Gly Ile Thr Gln Ser Ile Cys Leu Pro Leu Leu Ser Val Tyr Gln Leu
        1365                1370                1375

Ser Thr Asn Gly Thr Ala Gln Thr Pro Ser Ala Ser Arg Lys Ser Leu
        1380                1385                1390

Asp Ala Pro Ser Trp Pro Gly Val Tyr Arg Leu Ser Met Ser Leu Met
        1395                1400                1405

Glu Gln Leu Leu Lys Thr Leu Arg Tyr Asn Phe Leu Pro Glu Ala Leu
        1410                1415                1420

Asp Phe Val Gly Val His Gln Glu Arg Thr Leu Gln Cys Leu Asn Ala
1425                1430                1435                1440

Val Arg Thr Val Gln Ser Leu Ala Cys Leu Glu Glu Ala Asp His Thr
        1445                1450                1455

Val Gly Phe Ile Leu Gln Leu Ser Asn Phe Met Lys Glu Trp His Phe
        1460                1465                1470

His Leu Pro Gln Leu Met Arg Asp Ile Gln Val Asn Leu Gly Tyr Leu
        1475                1480                1485

Cys Gln Ala Cys Thr Ser Leu Leu His Ser Arg Lys Met Leu Gln His
        1490                1495                1500

Tyr Leu Gln Asn Lys Asn Gly Asp Gly Leu Pro Ser Ala Val Ala Gln
1505                1510                1515                1520

Arg Val Gln Arg Pro Pro Ser Ala Ala Ser Ala Ala Pro Ser Ser Ser
            1525                1530                1535

Lys Gln Pro Ala Ala Gln Thr Glu Ala Ser Glu Gln Ala Leu His
        1540                1545                1550

Thr Val Gln Tyr Gly Leu Leu Lys Ile Leu Ser Lys Thr Leu Ala Ala
        1555                1560                1565

Leu Arg His Phe Thr Pro Asp Val Cys Gln Ile Leu Leu Asp Gln Ser
        1570                1575                1580

Leu Asp Leu Ala Glu Tyr Asn Phe Leu Phe Ala Leu Ser Phe Thr Thr
1585                1590                1595                1600

Pro Thr Phe Asp Ser Glu Val Ala Pro Ser Phe Gly Thr Leu Leu Ala
            1605                1610                1615

Thr Val Asn Val Ala Leu Asn Met Leu Gly Glu Leu Asp Lys Lys Lys
        1620                1625                1630

Glu Pro Leu Thr Gln Ala Val Gly Leu Ser Thr Gln Ala Glu Gly Thr
```

-continued

```
                1635                1640                1645
Arg Thr Leu Lys Ser Leu Leu Met Phe Thr Met Glu Asn Cys Phe Tyr
    1650                1655                1660

Leu Leu Ile Ser Gln Ala Met Arg Tyr Leu Arg Asp Pro Ala Val His
1665                1670                1675                1680

Pro Arg Asp Lys Gln Arg Met Lys Gln Glu Leu Ser Ser Glu Leu Ser
                1685                1690                1695

Thr Leu Leu Ser Ser Leu Ser Arg Tyr His Arg Arg Gly Ala Pro Ser
            1700                1705                1710

Ser Pro Ala Thr Gly Val Leu Pro Ser Pro Gln Gly Lys Ser Thr Ser
        1715                1720                1725

Leu Ser Lys Ala Ser Pro Glu Ser Gln Glu Pro Leu Ile Gln Leu Val
    1730                1735                1740

Gln Ala Phe Val Arg His Met Gln Arg
1745                1750

<210> SEQ ID NO 20
<211> LENGTH: 14
<212> TYPE: PRT
<213> ORGANISM: Homo sapiens

<400> SEQUENCE: 20

Met Ile Arg Lys Ser Lys Ile Thr Ser Val Leu Ser Phe Cys
1               5                   10

<210> SEQ ID NO 21
<211> LENGTH: 1745
<212> TYPE: PRT
<213> ORGANISM: Homo sapiens

<400> SEQUENCE: 21

Ala Gly Gly Pro Cys Val Arg Ser Ser Arg Glu Leu Trp Thr Ile Leu
1               5                   10                  15

Leu Gly Arg Ser Ala Leu Arg Glu Leu Ser Gln Ile Glu Ala Glu Leu
            20                  25                  30

Asn Lys His Trp Arg Arg Leu Leu Glu Gly Leu Ser Tyr Tyr Lys Pro
        35                  40                  45

Pro Ser Pro Ser Ala Glu Lys Val Lys Ala Asn Lys Asp Val Ala
    50                  55                  60

Ser Pro Leu Lys Glu Leu Gly Leu Arg Ile Ser Lys Phe Leu Gly Leu
65                  70                  75                  80

Asp Glu Glu Gln Ser Val Gln Leu Leu Gln Cys Tyr Leu Gln Glu Asp
                85                  90                  95

Tyr Arg Gly Thr Arg Asp Ser Val Lys Thr Val Leu Asp Glu Arg
            100                 105                 110

Gln Ser Gln Ala Leu Ile Leu Lys Ile Ala Asp Tyr Tyr Glu Glu
        115                 120                 125

Arg Thr Cys Ile Leu Arg Cys Val Leu His Leu Leu Thr Tyr Phe Gln
    130                 135                 140

Asp Glu Arg His Pro Tyr Arg Val Glu Tyr Ala Asp Cys Val Asp Lys
145                 150                 155                 160

Leu Glu Lys Glu Leu Val Ser Lys Tyr Arg Gln Gln Phe Glu Glu Leu
                165                 170                 175

Tyr Lys Thr Glu Ala Pro Thr Trp Glu Thr His Gly Asn Leu Met Thr
            180                 185                 190

Glu Arg Gln Val Ser Arg Trp Phe Val Gln Cys Leu Arg Glu Gln Ser
```

-continued

```
           195                 200                 205
Met Leu Leu Glu Ile Ile Phe Leu Tyr Tyr Ala Tyr Phe Glu Met Ala
    210                 215                 220
Pro Ser Asp Leu Leu Val Leu Thr Lys Met Phe Lys Glu Gln Gly Phe
225                 230                 235                 240
Gly Ser Arg Gln Thr Asn Arg His Leu Val Asp Glu Thr Met Asp Pro
                245                 250                 255
Phe Val Asp Arg Ile Gly Tyr Phe Ser Ala Leu Ile Leu Val Glu Gly
                260                 265                 270
Met Asp Ile Glu Ser Leu His Lys Cys Ala Leu Asp Asp Arg Arg Glu
            275                 280                 285
Leu His Gln Phe Ala Gln Asp Gly Leu Ile Cys Gln Asp Met Asp Cys
        290                 295                 300
Leu Met Leu Thr Phe Gly Asp Ile Pro His His Ala Pro Val Leu Leu
305                 310                 315                 320
Ala Trp Ala Leu Leu Arg His Thr Leu Asn Pro Glu Glu Thr Ser Ser
                325                 330                 335
Val Val Arg Lys Ile Gly Gly Thr Ala Ile Gln Leu Asn Val Phe Gln
                340                 345                 350
Tyr Leu Thr Arg Leu Leu Gln Ser Leu Ala Ser Gly Gly Asn Asp Cys
            355                 360                 365
Thr Thr Ser Thr Ala Cys Met Cys Val Tyr Gly Leu Leu Ser Phe Val
        370                 375                 380
Leu Thr Ser Leu Glu Leu His Thr Leu Gly Asn Gln Gln Asp Ile Ile
385                 390                 395                 400
Asp Thr Ala Cys Glu Val Leu Ala Asp Pro Ser Leu Pro Glu Leu Phe
                405                 410                 415
Trp Gly Thr Glu Pro Thr Ser Gly Leu Gly Ile Ile Leu Asp Ser Val
                420                 425                 430
Cys Gly Met Phe Pro His Leu Leu Ser Pro Leu Leu Gln Leu Leu Arg
            435                 440                 445
Ala Leu Val Ser Gly Lys Ser Thr Ala Lys Lys Val Tyr Ser Phe Leu
        450                 455                 460
Asp Lys Met Ser Phe Tyr Asn Glu Leu Tyr Lys His Lys Pro His Asp
465                 470                 475                 480
Val Ile Ser His Glu Asp Gly Thr Leu Trp Arg Arg Gln Thr Pro Lys
                485                 490                 495
Leu Leu Tyr Pro Leu Gly Gly Gln Thr Asn Leu Arg Ile Pro Gln Gly
            500                 505                 510
Thr Val Gly Gln Val Met Leu Asp Asp Arg Ala Tyr Leu Val Arg Trp
        515                 520                 525
Glu Tyr Ser Tyr Ser Ser Trp Thr Leu Phe Thr Cys Glu Ile Glu Met
    530                 535                 540
Leu Leu His Val Val Ser Thr Ala Asp Val Ile Gln His Cys Gln Arg
545                 550                 555                 560
Val Lys Pro Ile Ile Asp Leu Val His Lys Val Ile Ser Thr Asp Leu
                565                 570                 575
Ser Ile Ala Asp Cys Leu Leu Pro Ile Thr Ser Arg Ile Tyr Met Leu
                580                 585                 590
Leu Gln Arg Leu Thr Thr Val Ile Ser Pro Pro Val Asp Val Ile Ala
            595                 600                 605
Ser Cys Val Asn Cys Leu Thr Val Leu Ala Ala Arg Asn Pro Ala Lys
        610                 615                 620
```

-continued

```
Val Trp Thr Asp Leu Arg His Thr Gly Phe Leu Pro Phe Val Ala His
625                 630                 635                 640

Pro Val Ser Ser Leu Ser Gln Met Ile Ser Ala Glu Gly Met Asn Ala
                645                 650                 655

Gly Gly Tyr Gly Asn Leu Leu Met Asn Ser Glu Pro Gln Gly Glu
            660                 665                 670

Tyr Gly Val Thr Ile Ala Phe Leu Arg Leu Ile Thr Thr Leu Val Lys
            675                 680                 685

Gly Gln Leu Gly Ser Thr Gln Ser Gln Gly Leu Val Pro Cys Val Met
690                 695                 700

Phe Val Leu Lys Glu Met Leu Pro Ser Tyr His Lys Trp Arg Tyr Asn
705                 710                 715                 720

Ser His Gly Val Arg Glu Gln Ile Gly Cys Leu Ile Leu Glu Leu Ile
                725                 730                 735

His Ala Ile Leu Asn Leu Cys His Glu Thr Asp Leu His Ser Ser His
            740                 745                 750

Thr Pro Ser Leu Gln Phe Leu Cys Ile Cys Ser Leu Ala Tyr Thr Glu
            755                 760                 765

Ala Gly Gln Thr Val Ile Asn Ile Met Gly Ile Gly Val Asp Thr Ile
770                 775                 780

Asp Met Val Met Ala Ala Gln Pro Arg Ser Asp Gly Ala Glu Gly Gln
785                 790                 795                 800

Gly Gln Gly Gln Leu Leu Ile Lys Thr Val Lys Leu Ala Phe Ser Val
                805                 810                 815

Thr Asn Asn Val Ile Arg Leu Lys Pro Pro Ser Asn Val Val Ser Pro
            820                 825                 830

Leu Glu Gln Ala Leu Ser Gln His Gly Ala His Gly Asn Asn Leu Ile
            835                 840                 845

Ala Val Leu Ala Lys Tyr Ile Tyr His Lys His Asp Pro Ala Leu Pro
850                 855                 860

Arg Leu Ala Ile Gln Leu Leu Lys Arg Leu Ala Thr Val Ala Pro Met
865                 870                 875                 880

Ser Val Tyr Ala Cys Leu Gly Asn Asp Ala Ala Ile Arg Asp Ala
                885                 890                 895

Phe Leu Thr Arg Leu Gln Ser Lys Ile Glu Asp Met Arg Ile Lys Val
            900                 905                 910

Met Ile Leu Glu Phe Leu Thr Val Ala Val Glu Thr Gln Pro Gly Leu
            915                 920                 925

Ile Glu Leu Phe Leu Asn Leu Glu Val Lys Asp Gly Ser Asp Gly Ser
930                 935                 940

Lys Glu Phe Ser Leu Gly Met Trp Ser Cys Leu His Ala Val Leu Glu
945                 950                 955                 960

Leu Ile Asp Ser Gln Gln Gln Asp Arg Tyr Trp Cys Pro Pro Leu Leu
                965                 970                 975

His Arg Ala Ala Ile Ala Phe Leu His Ala Leu Trp Gln Asp Arg Arg
            980                 985                 990

Asp Ser Ala Met Leu Val Leu Arg Thr Lys Pro Lys Phe Trp Glu Asn
            995                 1000                1005

Leu Thr Ser Pro Leu Phe Gly Thr Leu Ser Pro Ser Glu Thr Ser
    1010                1015                1020

Glu Pro Ser Ile Leu Glu Thr Cys Ala Leu Ile Met Lys Ile Ile Cys
1025                1030                1035                1040
```

```
Leu Glu Ile Tyr Tyr Val Val Lys Gly Ser Leu Asp Gln Ser Leu Lys
            1045                1050                1055

Asp Thr Leu Lys Lys Phe Ser Ile Glu Lys Arg Phe Ala Tyr Trp Ser
        1060                1065                1070

Gly Tyr Val Lys Ser Leu Ala Val His Val Ala Glu Thr Glu Gly Ser
        1075                1080            1085

Ser Cys Thr Ser Leu Leu Glu Tyr Gln Met Leu Val Ser Ala Trp Arg
    1090                1095                1100

Met Leu Leu Ile Ile Ala Thr Thr His Ala Asp Ile Met His Leu Thr
1105                1110                1115                1120

Asp Ser Val Val Arg Arg Gln Leu Phe Leu Asp Val Leu Asp Gly Thr
            1125                1130                1135

Lys Ala Leu Leu Leu Val Pro Ala Ser Val Asn Cys Leu Arg Leu Gly
        1140                1145                1150

Ser Met Lys Cys Thr Leu Leu Leu Ile Leu Leu Arg Gln Trp Lys Arg
    1155                1160                1165

Glu Leu Gly Ser Val Asp Glu Ile Leu Gly Pro Leu Thr Glu Ile Leu
        1170                1175            1180

Glu Gly Val Leu Gln Ala Asp Gln Gln Leu Met Glu Lys Thr Lys Ala
1185                1190                1195                1200

Lys Val Phe Ser Ala Phe Ile Thr Val Leu Gln Met Lys Glu Met Lys
            1205                1210                1215

Val Ser Asp Ile Pro Gln Tyr Ser Gln Leu Val Leu Asn Val Cys Glu
            1220                1225                1230

Thr Leu Gln Glu Glu Val Ile Ala Leu Phe Asp Gln Thr Arg His Ser
        1235                1240                1245

Leu Ala Leu Gly Ser Ala Thr Glu Asp Lys Asp Ser Met Glu Thr Asp
    1250                1255                1260

Asp Cys Ser Arg Ser Arg His Arg Asp Gln Arg Asp Gly Val Cys Val
1265                1270                1275                1280

Leu Gly Leu His Leu Ala Lys Glu Leu Cys Glu Val Asp Glu Asp Gly
            1285                1290                1295

Asp Ser Trp Leu Gln Val Thr Arg Arg Leu Pro Ile Leu Pro Thr Leu
            1300                1305                1310

Leu Thr Thr Leu Glu Val Ser Leu Arg Met Lys Gln Asn Leu His Phe
        1315                1320                1325

Thr Glu Ala Thr Leu His Leu Leu Leu Thr Leu Ala Arg Thr Gln Gln
    1330                1335                1340

Gly Ala Thr Ala Val Ala Gly Ala Gly Ile Thr Gln Ser Ile Cys Leu
1345                1350                1355                1360

Pro Leu Leu Ser Val Tyr Gln Leu Ser Thr Asn Gly Thr Ala Gln Thr
            1365                1370                1375

Pro Ser Ala Ser Arg Lys Ser Leu Asp Ala Pro Ser Trp Pro Gly Val
            1380                1385                1390

Tyr Arg Leu Ser Met Ser Leu Met Glu Gln Leu Leu Lys Thr Leu Arg
        1395                1400                1405

Tyr Asn Phe Leu Pro Glu Ala Leu Asp Phe Val Gly Val His Gln Glu
    1410                1415                1420

Arg Thr Leu Gln Cys Leu Asn Ala Val Arg Thr Val Gln Ser Leu Ala
1425                1430                1435                1440

Cys Leu Glu Glu Ala Asp His Thr Val Gly Phe Ile Leu Gln Leu Ser
            1445                1450                1455

Asn Phe Met Lys Glu Trp His Phe His Leu Pro Gln Leu Met Arg Asp
```

-continued

```
                1460                1465                1470
Ile Gln Val Asn Leu Gly Tyr Leu Cys Gln Ala Cys Thr Ser Leu Leu
    1475                1480                1485

His Ser Arg Lys Met Leu Gln His Tyr Leu Gln Asn Lys Asn Gly Asp
    1490                1495                1500

Gly Leu Pro Ser Ala Val Ala Gln Arg Val Gln Arg Pro Pro Ser Ala
1505                1510                1515                1520

Ala Ser Ala Ala Pro Ser Ser Ser Lys Gln Pro Ala Ala Asp Thr Glu
        1525                1530                1535

Ala Ser Glu Gln Gln Ala Leu His Thr Val Gln Tyr Gly Leu Leu Lys
    1540                1545                1550

Ile Leu Ser Lys Thr Leu Ala Ala Leu Arg His Phe Thr Pro Asp Val
    1555                1560                1565

Cys Gln Ile Leu Leu Asp Gln Ser Leu Asp Leu Ala Glu Tyr Asn Phe
    1570                1575                1580

Leu Phe Ala Leu Ser Phe Thr Thr Pro Thr Phe Asp Ser Glu Val Ala
1585                1590                1595                1600

Pro Ser Phe Gly Thr Leu Leu Ala Thr Val Asn Val Ala Leu Asn Met
        1605                1610                1615

Leu Gly Glu Leu Asp Lys Lys Lys Glu Pro Leu Thr Gln Ala Val Gly
        1620                1625                1630

Leu Ser Thr Gln Ala Glu Gly Thr Arg Thr Leu Lys Ser Leu Leu Met
    1635                1640                1645

Phe Thr Met Glu Asn Cys Phe Tyr Leu Leu Ile Ser Gln Ala Met Arg
    1650                1655                1660

Tyr Leu Arg Asp Pro Ala Val His Pro Arg Asp Lys Gln Arg Met Lys
1665                1670                1675                1680

Gln Glu Leu Ser Ser Glu Leu Ser Thr Leu Leu Ser Ser Leu Ser Arg
        1685                1690                1695

Tyr Phe Arg Arg Gly Ala Pro Ser Ser Pro Ala Thr Gly Val Leu Pro
            1700                1705                1710

Ser Pro Gln Gly Lys Ser Thr Ser Leu Ser Lys Ala Ser Pro Glu Ser
    1715                1720                1725

Gln Glu Pro Leu Ile Gln Leu Val Gln Ala Phe Val Arg His Met Gln
    1730                1735                1740

Arg
1745

<210> SEQ ID NO 22
<211> LENGTH: 3534
<212> TYPE: PRT
<213> ORGANISM: Homo sapiens

<400> SEQUENCE: 22

Met Ala Ser Gly Gly Val Arg Ala Ser Gly Arg Ala Lys Met Ala
1               5                   10                  15

Ala Ala Gly Gly Pro Cys Val Arg Ser Ser Arg Glu Leu Trp Thr
        20                  25                  30

Ile Leu Leu Gly Arg Ser Ala Leu Arg Glu Leu Ser Gln Ile Glu Ala
        35                  40                  45

Glu Leu Asn Lys His Trp Arg Arg Leu Leu Glu Gly Leu Ser Tyr Tyr
    50                  55                  60

Lys Pro Pro Ser Pro Ser Ser Ala Glu Lys Val Lys Ala Asn Lys Asp
65                  70                  75                  80
```

-continued

```
Val Ala Ser Pro Leu Lys Glu Leu Gly Leu Arg Ile Ser Lys Phe Leu
                85                  90                  95
Gly Leu Asp Glu Glu Gln Ser Val Gln Leu Leu Gln Cys Tyr Leu Gln
            100                 105                 110
Glu Asp Tyr Arg Gly Thr Arg Asp Ser Val Lys Thr Val Leu Gln Asp
        115                 120                 125
Glu Arg Gln Ser Gln Ala Leu Ile Leu Lys Ile Ala Asp Tyr Tyr Tyr
    130                 135                 140
Glu Glu Arg Thr Cys Ile Leu Arg Cys Val Leu His Leu Leu Thr Tyr
145                 150                 155                 160
Phe Gln Asp Glu Arg His Pro Tyr Arg Val Glu Tyr Ala Asp Cys Val
                165                 170                 175
Asp Lys Leu Glu Lys Glu Leu Val Ser Lys Tyr Arg Gln Gln Phe Glu
            180                 185                 190
Glu Leu Tyr Lys Thr Glu Ala Pro Thr Trp Glu Thr His Gly Asn Leu
        195                 200                 205
Met Thr Glu Arg Gln Val Ser Arg Trp Phe Val Gln Cys Leu Arg Glu
    210                 215                 220
Gln Ser Met Leu Leu Glu Ile Ile Phe Leu Tyr Tyr Ala Tyr Phe Glu
225                 230                 235                 240
Met Ala Pro Ser Asp Leu Leu Val Leu Thr Lys Met Phe Lys Glu Gln
                245                 250                 255
Gly Phe Gly Ser Arg Gln Thr Asn Arg His Leu Val Asp Glu Thr Met
            260                 265                 270
Asp Pro Phe Val Asp Arg Ile Gly Tyr Phe Ser Ala Leu Ile Leu Val
        275                 280                 285
Glu Gly Met Asp Ile Glu Ser Leu His Lys Cys Ala Leu Asp Asp Arg
    290                 295                 300
Arg Glu Leu His Gln Phe Ala Gln Asp Gly Leu Ile Cys Gln Asp Met
305                 310                 315                 320
Asp Cys Leu Met Leu Thr Phe Gly Asp Ile Pro His His Ala Pro Val
                325                 330                 335
Leu Leu Ala Trp Ala Leu Leu Arg His Thr Leu Asn Pro Glu Glu Thr
            340                 345                 350
Ser Ser Val Val Arg Lys Ile Gly Gly Thr Ala Ile Gln Leu Asn Val
        355                 360                 365
Phe Gln Tyr Leu Thr Arg Leu Leu Gln Ser Leu Ala Ser Gly Gly Asn
    370                 375                 380
Asp Cys Thr Thr Ser Thr Ala Cys Met Cys Val Tyr Gly Leu Leu Ser
385                 390                 395                 400
Phe Val Leu Thr Ser Leu Glu Leu His Thr Leu Gly Asn Gln Gln Asp
                405                 410                 415
Ile Ile Asp Thr Ala Cys Glu Val Leu Ala Asp Pro Ser Leu Pro Glu
            420                 425                 430
Leu Phe Trp Gly Thr Glu Pro Thr Ser Gly Leu Gly Ile Ile Leu Asp
        435                 440                 445
Ser Val Cys Gly Met Phe Pro His Leu Leu Ser Pro Leu Leu Gln Leu
    450                 455                 460
Leu Arg Ala Leu Val Ser Gly Lys Ser Thr Ala Lys Lys Val Tyr Ser
465                 470                 475                 480
Phe Leu Asp Lys Met Ser Phe Tyr Asn Glu Leu Tyr Lys His Lys Pro
                485                 490                 495
His Asp Val Ile Ser His Glu Asp Gly Thr Leu Trp Arg Arg Gln Thr
```

-continued

```
              500                 505                 510
Pro Lys Leu Leu Tyr Pro Leu Gly Gly Gln Thr Asn Leu Arg Ile Pro
        515                 520                 525
Gln Gly Thr Val Gly Gln Val Met Leu Asp Asp Arg Ala Tyr Leu Val
    530                 535                 540
Arg Trp Glu Tyr Ser Tyr Ser Ser Trp Thr Leu Phe Thr Cys Glu Ile
545                 550                 555                 560
Glu Met Leu Leu His Val Ser Thr Ala Asp Val Ile Gln His Cys
                565                 570                 575
Gln Arg Val Lys Pro Ile Ile Asp Leu Val His Lys Val Ile Ser Thr
        580                 585                 590
Asp Leu Ser Ile Ala Asp Cys Leu Leu Pro Ile Thr Ser Arg Ile Tyr
            595                 600                 605
Met Leu Leu Gln Arg Leu Thr Thr Val Ile Ser Pro Pro Val Asp Val
    610                 615                 620
Ile Ala Ser Cys Val Asn Cys Leu Thr Val Leu Ala Ala Arg Asn Pro
625                 630                 635                 640
Ala Lys Val Trp Thr Asp Leu Arg His Thr Gly Phe Leu Pro Phe Val
                645                 650                 655
Ala His Pro Val Ser Ser Leu Ser Gln Met Ile Ser Ala Glu Gly Met
            660                 665                 670
Asn Ala Gly Gly Tyr Gly Asn Leu Leu Met Asn Ser Glu Gln Pro Gln
        675                 680                 685
Gly Glu Tyr Gly Val Thr Ile Ala Phe Leu Arg Leu Ile Thr Thr Leu
    690                 695                 700
Val Lys Gly Gln Leu Gly Ser Thr Gln Ser Gln Gly Leu Val Pro Cys
705                 710                 715                 720
Val Met Phe Val Leu Lys Glu Met Leu Pro Ser Tyr His Lys Trp Arg
                725                 730                 735
Tyr Asn Ser His Gly Val Arg Glu Gln Ile Gly Cys Leu Ile Leu Glu
            740                 745                 750
Leu Ile His Ala Ile Leu Asn Leu Cys His Glu Thr Asp Leu His Ser
    755                 760                 765
Ser His Thr Pro Ser Leu Gln Phe Leu Cys Ile Cys Ser Leu Ala Tyr
770                 775                 780
Thr Glu Ala Gly Gln Thr Val Ile Asn Ile Met Gly Ile Gly Val Asp
785                 790                 795                 800
Thr Ile Asp Met Val Met Ala Ala Gln Pro Arg Ser Asp Gly Ala Glu
                805                 810                 815
Gly Gln Gly Gln Gly Gln Leu Leu Ile Lys Thr Val Lys Leu Ala Phe
            820                 825                 830
Ser Val Thr Asn Asn Val Ile Arg Leu Lys Pro Pro Ser Asn Val Val
    835                 840                 845
Ser Pro Leu Glu Gln Ala Leu Ser Gln His Gly Ala His Gly Asn Asn
850                 855                 860
Leu Ile Ala Val Leu Ala Lys Tyr Ile Tyr His Lys His Asp Pro Ala
865                 870                 875                 880
Leu Pro Arg Leu Ala Ile Gln Leu Leu Lys Arg Leu Ala Thr Val Ala
                885                 890                 895
Pro Met Ser Val Tyr Ala Cys Leu Gly Asn Asp Ala Ala Ile Arg
            900                 905                 910
Asp Ala Phe Leu Thr Arg Leu Gln Ser Lys Ile Glu Asp Met Arg Ile
    915                 920                 925
```

```
Lys Val Met Ile Leu Glu Phe Leu Thr Val Ala Val Glu Thr Gln Pro
        930                 935                 940

Gly Leu Ile Glu Leu Phe Leu Asn Leu Glu Val Lys Asp Gly Ser Asp
945                 950                 955                 960

Gly Ser Lys Glu Phe Ser Leu Gly Met Trp Ser Cys Leu His Ala Val
                965                 970                 975

Leu Glu Leu Ile Asp Ser Gln Gln Gln Asp Arg Tyr Trp Cys Pro Pro
            980                 985                 990

Leu Leu His Arg Ala Ala Ile Ala Phe Leu His Ala Leu Trp Gln Asp
        995                 1000                1005

Arg Arg Asp Ser Ala Met Leu Val Leu Arg Thr Lys Pro Lys Phe Trp
    1010                1015                1020

Glu Asn Leu Thr Ser Pro Leu Phe Gly Thr Leu Ser Pro Pro Ser Glu
1025                1030                1035                1040

Thr Ser Glu Pro Ser Ile Leu Glu Thr Cys Ala Leu Ile Met Lys Ile
                1045                1050                1055

Ile Cys Leu Glu Ile Tyr Tyr Val Val Lys Gly Ser Leu Asp Gln Ser
            1060                1065                1070

Leu Lys Asp Thr Leu Lys Lys Phe Ser Ile Glu Lys Arg Phe Ala Tyr
        1075                1080                1085

Trp Ser Gly Tyr Val Lys Ser Leu Ala Val His Val Ala Glu Thr Glu
    1090                1095                1100

Gly Ser Ser Cys Thr Ser Leu Leu Glu Tyr Gln Met Leu Val Ser Ala
1105                1110                1115                1120

Trp Arg Met Leu Leu Ile Ile Ala Thr Thr His Ala Asp Ile Met His
                1125                1130                1135

Leu Thr Asp Ser Val Val Arg Arg Gln Leu Phe Leu Asp Val Leu Asp
            1140                1145                1150

Gly Thr Lys Ala Leu Leu Leu Val Pro Ala Ser Val Asn Cys Leu Arg
        1155                1160                1165

Leu Gly Ser Met Lys Cys Thr Leu Leu Leu Ile Leu Leu Arg Gln Trp
    1170                1175                1180

Lys Ser Ile Leu Ser Arg Glu Leu Gly Ser Val Asp Glu Ile Leu Gly
1185                1190                1195                1200

Pro Leu Thr Glu Ile Leu Glu Gly Val Leu Gln Ala Asp Gln Gln Leu
                1205                1210                1215

Met Glu Lys Thr Lys Ala Lys Val Phe Ser Ala Phe Ile Thr Val Leu
            1220                1225                1230

Gln Met Lys Glu Met Lys Val Ser Asp Ile Pro Gln Tyr Ser Gln Leu
        1235                1240                1245

Val Leu Asn Val Cys Glu Thr Leu Gln Glu Glu Val Ile Ala Leu Phe
    1250                1255                1260

Asp Gln Thr Arg His Ser Leu Ala Leu Gly Ser Ala Thr Glu Asp Lys
1265                1270                1275                1280

Asp Ser Met Glu Thr Asp Asp Cys Ser Arg Ser Arg His Arg Asp Gln
                1285                1290                1295

Arg Asp Gly Val Cys Val Leu Gly Leu His Leu Ala Lys Glu Leu Cys
            1300                1305                1310

Glu Val Asp Glu Asp Gly Asp Ser Trp Leu Gln Val Thr Arg Arg Leu
        1315                1320                1325

Pro Ile Leu Pro Thr Leu Leu Thr Thr Leu Glu Val Ser Leu Arg Met
    1330                1335                1340
```

-continued

```
Lys Gln Asn Leu His Phe Thr Glu Ala Thr Leu His Leu Leu Leu Thr
1345                1350                1355                1360

Leu Ala Arg Thr Gln Gln Gly Ala Thr Ala Val Ala Gly Ala Gly Ile
            1365                1370                1375

Thr Gln Ser Ile Cys Leu Pro Leu Leu Ser Val Tyr Gln Leu Ser Thr
            1380                1385                1390

Asn Gly Thr Ala Gln Thr Pro Ser Ala Ser Arg Lys Ser Leu Asp Ala
        1395                1400                1405

Pro Ser Trp Pro Gly Val Tyr Arg Leu Ser Met Ser Leu Met Glu Gln
    1410                1415                1420

Leu Leu Lys Thr Leu Arg Tyr Asn Phe Leu Pro Glu Ala Leu Asp Phe
1425                1430                1435                1440

Val Gly Val His Gln Glu Arg Thr Leu Gln Cys Leu Asn Ala Val Arg
            1445                1450                1455

Thr Val Gln Ser Leu Ala Cys Leu Glu Glu Ala Asp His Thr Val Gly
            1460                1465                1470

Phe Ile Leu Gln Leu Ser Asn Phe Met Lys Glu Trp His Phe His Leu
        1475                1480                1485

Pro Gln Leu Met Arg Asp Ile Gln Val Asn Leu Gly Tyr Leu Cys Gln
    1490                1495                1500

Ala Cys Thr Ser Leu Leu His Ser Arg Lys Met Leu Gln His Tyr Leu
1505                1510                1515                1520

Gln Asn Lys Asn Gly Asp Gly Leu Pro Ser Ala Val Ala Gln Arg Val
            1525                1530                1535

Gln Arg Pro Pro Ser Ala Ala Ser Ala Ala Pro Ser Ser Ser Lys Gln
            1540                1545                1550

Pro Ala Ala Asp Thr Glu Ala Ser Glu Gln Gln Ala Leu His Thr Val
        1555                1560                1565

Gln Tyr Gly Leu Leu Lys Ile Leu Ser Lys Thr Leu Ala Ala Leu Arg
    1570                1575                1580

His Phe Thr Pro Asp Val Cys Gln Ile Leu Leu Asp Gln Ser Leu Asp
1585                1590                1595                1600

Leu Ala Glu Tyr Asn Phe Leu Phe Ala Leu Ser Phe Thr Thr Pro Thr
            1605                1610                1615

Phe Asp Ser Glu Val Ala Pro Ser Phe Gly Thr Leu Leu Ala Thr Val
            1620                1625                1630

Asn Val Ala Leu Asn Met Leu Gly Glu Leu Asp Lys Lys Lys Glu Pro
        1635                1640                1645

Leu Thr Gln Ala Val Gly Leu Ser Thr Gln Ala Glu Gly Thr Arg Thr
    1650                1655                1660

Leu Lys Ser Leu Leu Met Phe Thr Met Glu Asn Cys Phe Tyr Leu Leu
1665                1670                1675                1680

Ile Ser Gln Ala Met Arg Tyr Leu Arg Asp Pro Ala Val His Pro Arg
            1685                1690                1695

Asp Lys Gln Arg Met Lys Gln Glu Leu Ser Ser Glu Leu Ser Thr Leu
        1700                1705                1710

Leu Ser Ser Leu Ser Arg Tyr Phe Arg Arg Gly Ala Pro Ser Ser Pro
    1715                1720                1725

Ala Thr Gly Val Leu Pro Ser Pro Gln Gly Lys Ser Thr Ser Leu Ser
        1730                1735                1740

Lys Ala Ser Pro Glu Ser Gln Glu Pro Leu Ile Gln Leu Val Gln Ala
1745                1750                1755                1760

Phe Val Arg His Met Gln Arg Met Ala Ser Gly Gly Gly Val Arg Ala
```

```
                  1765                1770                1775
Ser Gly Arg Ala Lys Met Ala Ala Ala Gly Gly Pro Cys Val Arg
        1780                1785                1790
Ser Ser Arg Glu Leu Trp Thr Ile Leu Leu Gly Arg Ser Ala Leu Arg
    1795                1800                1805
Glu Leu Ser Gln Ile Glu Ala Glu Leu Asn Lys His Trp Arg Arg Leu
    1810                1815                1820
Leu Glu Gly Leu Ser Tyr Tyr Lys Pro Pro Ser Pro Ser Ser Ala Glu
1825                1830                1835                1840
Lys Val Lys Ala Asn Lys Asp Val Ala Ser Pro Leu Lys Glu Leu Gly
            1845                1850                1855
Leu Arg Ile Ser Lys Phe Leu Gly Leu Asp Glu Glu Gln Ser Val Gln
        1860                1865                1870
Leu Leu Gln Cys Tyr Leu Gln Glu Asp Tyr Arg Gly Thr Arg Asp Ser
    1875                1880                1885
Val Lys Thr Val Leu Gln Asp Glu Arg Gln Ser Gln Ala Leu Ile Leu
    1890                1895                1900
Lys Ile Ala Asp Tyr Tyr Tyr Glu Glu Arg Thr Cys Ile Leu Arg Cys
1905                1910                1915                1920
Val Leu His Leu Leu Thr Tyr Phe Gln Asp Glu Arg His Pro Tyr Arg
            1925                1930                1935
Val Glu Tyr Ala Asp Cys Val Asp Lys Leu Glu Lys Glu Leu Val Ser
            1940                1945                1950
Lys Tyr Arg Gln Gln Phe Glu Glu Leu Tyr Lys Thr Glu Ala Pro Thr
    1955                1960                1965
Trp Glu Thr His Gly Asn Leu Met Thr Glu Arg Gln Val Ser Arg Trp
    1970                1975                1980
Phe Val Gln Cys Leu Arg Glu Gln Ser Met Leu Leu Glu Ile Ile Phe
1985                1990                1995                2000
Leu Tyr Tyr Ala Tyr Phe Glu Met Ala Pro Ser Asp Leu Leu Val Leu
            2005                2010                2015
Thr Lys Met Phe Lys Glu Gln Gly Phe Gly Ser Arg Gln Thr Asn Arg
    2020                2025                2030
His Leu Val Asp Glu Thr Met Asp Pro Phe Val Asp Arg Ile Gly Tyr
    2035                2040                2045
Phe Ser Ala Leu Ile Leu Val Glu Gly Met Asp Ile Glu Ser Leu His
    2050                2055                2060
Lys Cys Ala Leu Asp Asp Arg Arg Glu Leu His Gln Phe Ala Gln Asp
2065                2070                2075                2080
Gly Leu Ile Cys Gln Asp Met Asp Cys Leu Met Leu Thr Phe Gly Asp
            2085                2090                2095
Ile Pro His His Ala Pro Val Leu Leu Ala Trp Ala Leu Leu Arg His
    2100                2105                2110
Thr Leu Asn Pro Glu Glu Thr Ser Ser Val Val Arg Lys Ile Gly Gly
        2115                2120                2125
Thr Ala Ile Gln Leu Asn Val Phe Gln Tyr Leu Thr Arg Leu Leu Gln
    2130                2135                2140
Ser Leu Ala Ser Gly Gly Asn Asp Cys Thr Thr Ser Thr Ala Cys Met
2145                2150                2155                2160
Cys Val Tyr Gly Leu Leu Ser Phe Val Leu Thr Ser Leu Glu Leu His
            2165                2170                2175
Thr Leu Gly Asn Gln Gln Asp Ile Ile Asp Thr Ala Cys Glu Val Leu
        2180                2185                2190
```

```
Ala Asp Pro Ser Leu Pro Glu Leu Phe Trp Gly Thr Glu Pro Thr Ser
        2195                2200                2205

Gly Leu Gly Ile Ile Leu Asp Ser Val Cys Gly Met Phe Pro His Leu
    2210                2215                2220

Leu Ser Pro Leu Leu Gln Leu Leu Arg Ala Leu Val Ser Gly Lys Ser
2225                2230                2235                2240

Thr Ala Lys Lys Val Tyr Ser Phe Leu Asp Lys Met Ser Phe Tyr Asn
            2245                2250                2255

Glu Leu Tyr Lys His Lys Pro His Asp Val Ile Ser His Glu Asp Gly
            2260                2265                2270

Thr Leu Trp Arg Arg Gln Thr Pro Lys Leu Leu Tyr Pro Leu Gly Gly
        2275                2280                2285

Gln Thr Asn Leu Arg Ile Pro Gln Gly Thr Val Gly Gln Val Met Leu
    2290                2295                2300

Asp Asp Arg Ala Tyr Leu Val Arg Trp Glu Tyr Ser Tyr Ser Ser Trp
2305                2310                2315                2320

Thr Leu Phe Thr Cys Glu Ile Glu Met Leu Leu His Val Val Ser Thr
            2325                2330                2335

Ala Asp Val Ile Gln His Cys Gln Arg Val Lys Pro Ile Ile Asp Leu
            2340                2345                2350

Val His Lys Val Ile Ser Thr Asp Leu Ser Ile Ala Asp Cys Leu Leu
        2355                2360                2365

Pro Ile Thr Ser Arg Ile Tyr Met Leu Leu Gln Arg Leu Thr Thr Val
        2370                2375                2380

Ile Ser Pro Pro Val Asp Val Ile Ala Ser Cys Val Asn Cys Leu Thr
2385                2390                2395                2400

Val Leu Ala Ala Arg Asn Pro Ala Lys Val Trp Thr Asp Leu Arg His
            2405                2410                2415

Thr Gly Phe Leu Pro Phe Val Ala His Pro Val Ser Ser Leu Ser Gln
            2420                2425                2430

Met Ile Ser Ala Glu Gly Met Asn Ala Gly Gly Tyr Gly Asn Leu Leu
        2435                2440                2445

Met Asn Ser Glu Gln Pro Gln Gly Glu Tyr Gly Val Thr Ile Ala Phe
        2450                2455                2460

Leu Arg Leu Ile Thr Thr Leu Val Lys Gly Gln Leu Gly Ser Thr Gln
2465                2470                2475                2480

Ser Gln Gly Leu Val Pro Cys Val Met Phe Val Leu Lys Glu Met Leu
            2485                2490                2495

Pro Ser Tyr His Lys Trp Arg Tyr Asn Ser His Gly Val Arg Glu Gln
            2500                2505                2510

Ile Gly Cys Leu Ile Leu Glu Leu Ile His Ala Ile Leu Asn Leu Cys
        2515                2520                2525

His Glu Thr Asp Leu His Ser Ser His Thr Pro Ser Leu Gln Phe Leu
        2530                2535                2540

Cys Ile Cys Ser Leu Ala Tyr Thr Glu Ala Gly Gln Thr Val Ile Asn
2545                2550                2555                2560

Ile Met Gly Ile Gly Val Asp Thr Ile Asp Met Val Met Ala Ala Gln
            2565                2570                2575

Pro Arg Ser Asp Gly Ala Glu Gly Gln Gly Gln Gly Gln Leu Leu Ile
            2580                2585                2590

Lys Thr Val Lys Leu Ala Phe Ser Val Thr Asn Asn Val Ile Arg Leu
        2595                2600                2605
```

```
Lys Pro Pro Ser Asn Val Val Ser Pro Leu Glu Gln Ala Leu Ser Gln
    2610                2615                2620

His Gly Ala His Gly Asn Asn Leu Ile Ala Val Leu Ala Lys Tyr Ile
2625                2630                2635                2640

Tyr His Lys His Asp Pro Ala Leu Pro Arg Leu Ala Ile Gln Leu Leu
            2645                2650                2655

Lys Arg Leu Ala Thr Val Ala Pro Met Ser Val Tyr Ala Cys Leu Gly
        2660                2665                2670

Asn Asp Ala Ala Ala Ile Arg Asp Ala Phe Leu Thr Arg Leu Gln Ser
    2675                2680                2685

Lys Ile Glu Asp Met Arg Ile Lys Val Met Ile Leu Glu Phe Leu Thr
2690                2695                2700

Val Ala Val Glu Thr Gln Pro Gly Leu Ile Glu Leu Phe Leu Asn Leu
2705                2710                2715                2720

Glu Val Lys Asp Gly Ser Asp Gly Ser Lys Glu Phe Ser Leu Gly Met
            2725                2730                2735

Trp Ser Cys Leu His Ala Val Leu Glu Leu Ile Asp Ser Gln Gln Gln
        2740                2745                2750

Asp Arg Tyr Trp Cys Pro Pro Leu Leu His Arg Ala Ala Ile Ala Phe
    2755                2760                2765

Leu His Ala Leu Trp Gln Asp Arg Arg Asp Ser Ala Met Leu Val Leu
    2770                2775                2780

Arg Thr Lys Pro Lys Phe Trp Glu Asn Leu Thr Ser Pro Leu Phe Gly
2785                2790                2795                2800

Thr Leu Ser Pro Pro Ser Glu Thr Ser Glu Pro Ser Ile Leu Glu Thr
            2805                2810                2815

Cys Ala Leu Ile Met Lys Ile Ile Cys Leu Glu Ile Tyr Tyr Val Val
        2820                2825                2830

Lys Gly Ser Leu Asp Gln Ser Leu Lys Asp Thr Leu Lys Lys Phe Ser
    2835                2840                2845

Ile Glu Lys Arg Phe Ala Tyr Trp Ser Gly Tyr Val Lys Ser Leu Ala
    2850                2855                2860

Val His Val Ala Glu Thr Glu Gly Ser Ser Cys Thr Ser Leu Leu Glu
2865                2870                2875                2880

Tyr Gln Met Leu Val Ser Ala Trp Arg Met Leu Leu Ile Ile Ala Thr
            2885                2890                2895

Thr His Ala Asp Ile Met His Leu Thr Asp Ser Val Val Arg Arg Gln
        2900                2905                2910

Leu Phe Leu Asp Val Leu Asp Gly Thr Lys Ala Leu Leu Leu Val Pro
    2915                2920                2925

Ala Ser Val Asn Cys Leu Arg Leu Gly Ser Met Lys Cys Thr Leu Leu
    2930                2935                2940

Leu Ile Leu Leu Arg Gln Trp Lys Ser Ile Leu Ser Arg Glu Leu Gly
2945                2950                2955                2960

Ser Val Asp Glu Ile Leu Gly Pro Leu Thr Glu Ile Leu Glu Gly Val
            2965                2970                2975

Leu Gln Ala Asp Gln Gln Leu Met Glu Lys Thr Lys Ala Lys Val Phe
        2980                2985                2990

Ser Ala Phe Ile Thr Val Leu Gln Met Lys Glu Met Lys Val Ser Asp
    2995                3000                3005

Ile Pro Gln Tyr Ser Gln Leu Val Leu Asn Val Cys Glu Thr Leu Gln
    3010                3015                3020

Glu Glu Val Ile Ala Leu Phe Asp Gln Thr Arg His Ser Leu Ala Leu
```

-continued

```
            3025                3030                3035                3040
Gly Ser Ala Thr Glu Asp Lys Asp Ser Met Glu Thr Asp Asp Cys Ser
                3045                3050                3055
Arg Ser Arg His Arg Asp Gln Arg Asp Gly Val Cys Val Leu Gly Leu
            3060                3065                3070
His Leu Ala Lys Glu Leu Cys Glu Val Asp Glu Asp Gly Asp Ser Trp
        3075                3080                3085
Leu Gln Val Thr Arg Arg Leu Pro Ile Leu Pro Thr Leu Leu Thr Thr
    3090                3095                3100
Leu Glu Val Ser Leu Arg Met Lys Gln Asn Leu His Phe Thr Glu Ala
3105                3110                3115                3120
Thr Leu His Leu Leu Leu Thr Leu Ala Arg Thr Gln Gln Gly Ala Thr
            3125                3130                3135
Ala Val Ala Gly Ala Gly Ile Thr Gln Ser Ile Cys Leu Pro Leu Leu
            3140                3145                3150
Ser Val Tyr Gln Leu Ser Thr Asn Gly Thr Ala Gln Thr Pro Ser Ala
        3155                3160                3165
Ser Arg Lys Ser Leu Asp Ala Pro Ser Trp Pro Gly Val Tyr Arg Leu
    3170                3175                3180
Ser Met Ser Leu Met Glu Gln Leu Leu Lys Thr Leu Arg Tyr Asn Phe
3185                3190                3195                3200
Leu Pro Glu Ala Leu Asp Phe Val Gly Val His Glu Arg Thr Leu
            3205                3210                3215
Gln Cys Leu Asn Ala Val Arg Thr Val Gln Ser Leu Ala Cys Leu Glu
            3220                3225                3230
Glu Ala Asp His Thr Val Gly Phe Ile Leu Gln Leu Ser Asn Phe Met
        3235                3240                3245
Lys Glu Trp His Phe His Leu Pro Gln Leu Met Arg Asp Ile Gln Val
    3250                3255                3260
Asn Leu Gly Tyr Leu Cys Gln Ala Cys Thr Ser Leu Leu His Ser Arg
3265                3270                3275                3280
Lys Met Leu Gln His Tyr Leu Gln Asn Lys Asn Gly Asp Gly Leu Pro
            3285                3290                3295
Ser Ala Val Ala Gln Arg Val Gln Arg Pro Pro Ser Ala Ala Ser Ala
            3300                3305                3310
Ala Pro Ser Ser Ser Lys Gln Pro Ala Ala Asp Thr Glu Ala Ser Glu
        3315                3320                3325
Gln Gln Ala Leu His Thr Val Gln Tyr Gly Leu Leu Lys Ile Leu Ser
    3330                3335                3340
Lys Thr Leu Ala Ala Leu Arg His Phe Thr Pro Asp Val Cys Gln Ile
3345                3350                3355                3360
Leu Leu Asp Gln Ser Leu Asp Leu Ala Glu Tyr Asn Phe Leu Phe Ala
            3365                3370                3375
Leu Ser Phe Thr Thr Pro Thr Phe Asp Ser Glu Val Ala Pro Ser Phe
        3380                3385                3390
Gly Thr Leu Leu Ala Thr Val Asn Val Ala Leu Asn Met Leu Gly Glu
    3395                3400                3405
Leu Asp Lys Lys Lys Glu Pro Leu Thr Gln Ala Val Gly Leu Ser Thr
    3410                3415                3420
Gln Ala Glu Gly Thr Arg Thr Leu Lys Ser Leu Leu Met Phe Thr Met
3425                3430                3435                3440
Glu Asn Cys Phe Tyr Leu Leu Ile Ser Gln Ala Met Arg Tyr Leu Arg
            3445                3450                3455
```

```
Asp Pro Ala Val His Pro Arg Asp Lys Gln Arg Met Lys Gln Glu Leu
        3460                3465                3470

Ser Ser Glu Leu Ser Thr Leu Leu Ser Ser Leu Ser Arg Tyr Phe Arg
        3475                3480                3485

Arg Gly Ala Pro Ser Ser Pro Ala Thr Gly Val Leu Pro Ser Pro Gln
    3490                3495                3500

Gly Lys Ser Thr Ser Leu Ser Lys Ala Ser Pro Glu Ser Gln Glu Pro
3505                3510                3515                3520

Leu Ile Gln Leu Val Gln Ala Phe Val Arg His Met Gln Arg
                3525                3530

<210> SEQ ID NO 23
<211> LENGTH: 1111
<212> TYPE: PRT
<213> ORGANISM: Homo sapiens

<400> SEQUENCE: 23

Met Thr Gln Met Ile Ser Ala Glu Gly Met Asn Ala Gly Gly Tyr Gly
1               5                   10                  15

Ser Leu Leu Met Asn Ser Glu Gln Pro Gln Gly Glu Tyr Gly Val Thr
            20                  25                  30

Ile Ala Phe Leu Arg Leu Val Thr Thr Leu Val Lys Gly Gln Leu Gly
        35                  40                  45

Ser Thr Gln Ser Gln Gly Leu Val Pro Cys Val Met Phe Val Leu Lys
    50                  55                  60

Glu Met Leu Pro Ser Tyr His Lys Trp Arg Tyr Asn Ser His Gly Val
65                  70                  75                  80

Arg Glu Leu Ile Gly Cys Leu Ile Leu Glu Leu Ile His Ala Ile Leu
                85                  90                  95

Asn Leu Cys Gln Glu Thr Glu Leu His Ser Ser His Thr Pro Ser Leu
            100                 105                 110

Pro Ser Leu Cys Ile Cys Ser Leu Ala Tyr Thr Glu Ala Gly Gln Thr
        115                 120                 125

Val Ile Ser Ile Met Gly Ile Gly Val Asp Thr Ile Asp Met Val Met
    130                 135                 140

Ala Ala Gln Pro Arg Ser Asp Gly Pro Glu Gly Gln Gly Gln Gly Gln
145                 150                 155                 160

Leu Leu Ile Lys Thr Val Lys Leu Ala Phe Ser Val Thr Asn Asn Val
                165                 170                 175

Ile Arg Leu Lys Pro Pro Ser Asn Val Val Ser Pro Leu Glu Gln Ala
            180                 185                 190

Leu Thr Gln His Gly Ala His Gly Asn Asn Leu Ile Ala Val Leu Ala
        195                 200                 205

Lys Tyr Ile Tyr His Arg His Asp Pro Ala Leu Pro Arg Leu Ala Ile
    210                 215                 220

Gln Leu Leu Lys Arg Leu Ala Thr Val Ala Pro Met Ser Val Tyr Ala
225                 230                 235                 240

Cys Leu Gly Ser Asp Ala Ala Ile Arg Asp Ala Phe Leu Thr Arg
                245                 250                 255

Leu Gln Ser Lys Ile Glu Asp Met Arg Ile Lys Val Met Ile Leu Glu
            260                 265                 270

Phe Leu Thr Val Ala Val Glu Thr Gln Pro Gly Leu Ile Glu Leu Phe
        275                 280                 285

Leu Asn Leu Glu Val Lys Asp Gly Ser Asn Gly Ser Lys Glu Phe Ser
```

```
                  290                 295                 300
Leu Gly Val Trp Ser Cys Leu His Val Val Leu Glu Leu Ile Asp Ser
305                 310                 315                 320

Gln Gln Gln Asp Arg Tyr Trp Cys Pro Pro Leu Leu His Arg Ala Ala
                325                 330                 335

Ile Ala Phe Leu His Ala Leu Trp Gln Asp Arg Arg Asp Ser Ala Met
                340                 345                 350

Leu Val Leu Arg Thr Lys Pro Lys Phe Trp Glu Asn Leu Thr Ser Pro
                355                 360                 365

Leu Phe Gly Thr Leu Ser Pro Pro Ser Glu Thr Ser Glu Pro Ser Val
370                 375                 380

Leu Glu Thr Cys Ala Leu Ile Met Lys Ile Ile Cys Leu Glu Ile Tyr
385                 390                 395                 400

Tyr Val Val Lys Gly Ser Leu Asp Gln Ser Leu Lys Asp Thr Leu Lys
                405                 410                 415

Lys Phe Ser Ser Glu Lys Arg Phe Ala Tyr Trp Ser Gly Tyr Val Lys
                420                 425                 430

Ser Leu Ala Val Tyr Met Ala Asp Thr Glu Gly Ser Ser Cys Thr Ser
                435                 440                 445

Leu Leu Glu Tyr Gln Met Leu Val Ser Ala Trp Arg Ile Leu Leu Ile
                450                 455                 460

Ile Ala Ala Ser His Ala Asp Val Met His Leu Thr Asp Met Ala Val
465                 470                 475                 480

Arg Arg Gln Leu Phe Leu Asp Val Leu Asp Gly Thr Lys Ala Leu Leu
                485                 490                 495

Leu Val Ala Ala Ser Val Asn Cys Leu Arg Leu Gly Ser Met Met Cys
                500                 505                 510

Thr Leu Leu Leu Ile Leu Leu Arg Gln Trp Lys Arg Glu Leu Gly Ala
                515                 520                 525

Val Glu Lys Ile Leu Gly Pro Leu Thr Glu Ile Leu Glu Gly Val Leu
530                 535                 540

Gln Ala Asp Gln Gln Leu Met Glu Lys Thr Lys Ala Lys Val Phe Ser
545                 550                 555                 560

Ala Phe Ile Thr Val Leu Gln Met Lys Glu Leu Arg Val Gly Asp Ile
                565                 570                 575

Pro Gln Tyr Ser Gln Leu Val Leu Asn Val Cys Glu Thr Leu Gln Glu
                580                 585                 590

Glu Val Ile Ala Leu Phe Asp Gln Thr Arg His Ser Leu Ala Ser Asp
                595                 600                 605

Ser Ala Ala Glu Asp Lys Asp Ser Met Glu Thr Asp Asp Cys Pro Arg
610                 615                 620

Pro Arg His Lys Asp Gln Arg Asp Gly Val Cys Val Leu Gly Leu His
625                 630                 635                 640

Leu Ala Lys Glu Leu Cys Glu Val Asp Glu Asp Gly Asp Ser Trp Leu
                645                 650                 655

Gln Val Thr Arg Arg Leu Pro Ile Leu Pro Thr Leu Thr Thr Leu
                660                 665                 670

Glu Val Ser Leu Arg Met Lys Gln Asn Leu His Phe Thr Glu Ala Ala
                675                 680                 685

Leu His Leu Leu Leu Thr Leu Ala Arg Thr Gln Gln Gly Ala Thr Ala
                690                 695                 700

Val Ala Gly Ala Gly Ile Thr Gln Ser Ile Cys Leu Pro Leu Leu Ser
705                 710                 715                 720
```

Val Tyr Gln Leu Ser Ser Asn Gly Thr Gly Gln Thr Pro Ser Thr Ser
            725                 730                 735

Arg Lys Ser Leu Asp Ala Pro Ser Trp Pro Gly Val Tyr Arg Leu Ser
        740                 745                 750

Met Ser Leu Met Glu Arg Leu Leu Lys Thr Leu Arg Tyr Asn Phe Leu
    755                 760                 765

Thr Glu Ala Leu Asp Phe Val Gly Val His Glu Arg Thr Leu Gln
770                 775                 780

Cys Leu Asn Ala Val Lys Thr Val Gln Ser Leu Ala Cys Leu Glu Glu
785                 790                 795                 800

Ala Asp His Thr Val Gly Phe Ile Leu Gln Leu Ser His Phe Arg Lys
                805                 810                 815

Glu Trp His Phe His Leu Pro Gln Leu Met Arg Asp Val Gln Val Asn
            820                 825                 830

Leu Gly Tyr Leu Cys Gln Ala Cys Thr Ser Leu Leu His Ser Arg Lys
        835                 840                 845

Met Leu Gln His Tyr Leu Gln Asn Lys Asn Gly Asp Gly Leu Pro Ser
    850                 855                 860

Ala Val Thr Pro Arg Ala Gln Arg Pro Ser Thr Thr Thr Thr Thr Thr
865                 870                 875                 880

Thr Thr Thr Thr Ala Leu Ala Thr Pro Ala Gly Cys Ser Ser Lys Gln
                885                 890                 895

Pro Thr Ala Asp Thr Glu Ala Ser Glu Gln Arg Ala Leu His Thr Val
            900                 905                 910

Gln Tyr Gly Leu Leu Lys Ile Leu Ser Arg Thr Leu Ala Ala Leu Arg
        915                 920                 925

His Phe Thr Pro Asp Val Cys Gln Ile Leu Leu Asp Gln Ser Leu Asp
    930                 935                 940

Leu Ala Glu Tyr Asn Phe Leu Phe Ala Leu Ser Phe Thr Thr Pro Thr
945                 950                 955                 960

Phe Asp Ser Glu Val Ala Pro Ser Phe Gly Thr Leu Leu Ala Thr Val
                965                 970                 975

Asn Val Ala Leu Asn Met Leu Gly Glu Leu Asp Lys Lys Lys Glu Ser
            980                 985                 990

Leu Thr Gln Ala Val Gly Leu Ser Thr Gln Ala Glu Gly Thr Arg Thr
        995                 1000                1005

Leu Lys Ser Leu Leu Met Phe Thr Met Glu Asn Cys Phe Tyr Leu Leu
    1010                1015                1020

Ile Ser Gln Ala Val Arg Tyr Leu Arg Asp Pro Ala Val His Pro Arg
1025                1030                1035                1040

Asp Lys Gln Arg Met Lys Gln Glu Leu Ser Ser Glu Leu Ser Thr Leu
                1045                1050                1055

Leu Ser Leu Ser Arg Tyr Phe Arg Arg Gly Ala Pro Ser Ser Pro
            1060                1065                1070

Ala Ala Gly Val Leu Pro Ser Pro Gln Gly Lys Ala Thr Ser Leu Ser
        1075                1080                1085

Lys Ala Ser Pro Glu Ser Gln Glu Pro Leu Ile Gln Leu Val Gln Ala
    1090                1095                1100

Phe Val Arg His Val Gln Arg
1105                1110

<210> SEQ ID NO 24
<211> LENGTH: 853

<212> TYPE: PRT
<213> ORGANISM: Homo sapiens

<400> SEQUENCE: 24

```
Val Thr Ile Ala Phe Leu Arg Leu Ile Thr Thr Leu Val Lys Gly Gln
  1               5                  10                  15

Leu Gly Ser Thr Gln Ser Gln Gly Leu Val Pro Cys Val Met Phe Val
             20                  25                  30

Leu Lys Glu Met Leu Pro Ser Tyr His Lys Trp Arg Tyr Asn Ser His
         35                  40                  45

Gly Val Arg Glu Gln Ile Gly Cys Leu Ile Leu Glu Leu Ile His Ala
     50                  55                  60

Ile Leu Asn Leu Cys His Glu Thr Asp Leu His Ser Ser His Thr Pro
 65                  70                  75                  80

Ser Leu Gln Phe Leu Cys Ile Cys Ser Leu Ala Tyr Thr Glu Ala Gly
                 85                  90                  95

Gln Thr Val Ile Asn Ile Met Gly Ile Gly Val Asp Thr Ile Asp Met
            100                 105                 110

Val Met Ala Ala Gln Pro Arg Ser Asp Gly Ala Glu Gly Gln Gly Gln
        115                 120                 125

Gly Gln Leu Leu Ile Lys Thr Val Lys Leu Ala Phe Ser Val Thr Asn
130                 135                 140

Asn Val Ile Arg Leu Lys Pro Pro Ser Asn Val Val Ser Pro Leu Glu
145                 150                 155                 160

Gln Ala Leu Ser Gln His Gly Ala His Gly Asn Asn Leu Ile Ala Val
                165                 170                 175

Leu Ala Lys Tyr Ile Tyr His Lys His Asp Pro Ala Leu Pro Arg Leu
            180                 185                 190

Ala Ile Gln Leu Leu Lys Arg Leu Ala Thr Val Ala Pro Met Ser Val
        195                 200                 205

Tyr Ala Cys Leu Gly Asn Asp Ala Ala Ala Ile Arg Asp Ala Phe Leu
210                 215                 220

Thr Arg Leu Gln Ser Lys Ile Glu Asp Met Arg Ile Lys Val Met Ile
225                 230                 235                 240

Leu Glu Phe Leu Thr Val Ala Val Glu Thr Gln Pro Gly Leu Ile Glu
                245                 250                 255

Leu Phe Leu Asn Leu Glu Val Lys Asp Gly Ser Asp Gly Ser Lys Glu
            260                 265                 270

Phe Ser Leu Gly Met Trp Ser Cys Leu His Ala Val Leu Glu Leu Ile
        275                 280                 285

Asp Ser Gln Gln Gln Asp Arg Tyr Trp Cys Pro Pro Leu Leu His Arg
290                 295                 300

Ala Ala Ile Ala Phe Leu His Ala Leu Trp Gln Asp Arg Arg Asp Ser
305                 310                 315                 320

Ala Met Leu Val Leu Arg Thr Lys Pro Lys Phe Trp Glu Asn Leu Thr
                325                 330                 335

Ser Pro Leu Phe Gly Thr Leu Ser Pro Pro Ser Glu Thr Ser Glu Pro
            340                 345                 350

Ser Ile Leu Glu Thr Cys Ala Leu Ile Met Lys Ile Ile Cys Leu Glu
        355                 360                 365

Ile Tyr Tyr Val Val Lys Gly Ser Leu Asp Gln Ser Leu Lys Asp Thr
370                 375                 380

Leu Lys Lys Phe Ser Ile Glu Lys Arg Phe Ala Tyr Trp Ser Gly Tyr
385                 390                 395                 400
```

```
Val Lys Ser Leu Ala Val His Val Ala Glu Thr Glu Gly Ser Ser Cys
            405                 410                 415

Thr Ser Leu Leu Glu Tyr Gln Met Leu Val Ser Ala Trp Arg Met Leu
            420                 425                 430

Leu Ile Ile Ala Thr Thr His Ala Asp Ile Met His Leu Thr Asp Ser
            435                 440                 445

Val Val Arg Arg Gln Leu Phe Leu Asp Val Leu Asp Gly Thr Lys Ala
        450                 455                 460

Leu Leu Leu Val Pro Ala Ser Val Asn Cys Leu Arg Leu Gly Ser Met
465                 470                 475                 480

Lys Cys Thr Leu Leu Leu Ile Leu Leu Arg Gln Trp Lys Arg Glu Leu
            485                 490                 495

Gly Ser Val Asp Glu Ile Leu Gly Pro Leu Thr Glu Ile Leu Glu Gly
            500                 505                 510

Val Leu Gln Ala Asp Gln Gln Leu Met Glu Lys Thr Lys Ala Lys Val
            515                 520                 525

Phe Ser Ala Phe Ile Thr Val Leu Gln Met Lys Glu Met Lys Val Ser
            530                 535                 540

Asp Ile Pro Gln Tyr Ser Gln Leu Val Leu Asn Val Cys Glu Thr Leu
545                 550                 555                 560

Gln Glu Glu Val Ile Ala Leu Phe Asp Gln Thr Arg His Ser Leu Ala
                565                 570                 575

Leu Gly Ser Ala Thr Glu Asp Lys Asp Ser Met Glu Thr Asp Asp Cys
                580                 585                 590

Ser Arg Ser Arg His Arg Asp Gln Arg Asp Gly Val Cys Val Leu Gly
            595                 600                 605

Leu His Leu Ala Lys Glu Leu Cys Glu Val Asp Glu Asp Gly Asp Ser
            610                 615                 620

Trp Leu Gln Val Thr Arg Arg Leu Pro Ile Leu Pro Thr Leu Leu Thr
625                 630                 635                 640

Thr Leu Glu Val Ser Leu Arg Met Lys Gln Asn Leu His Phe Thr Glu
                645                 650                 655

Ala Thr Leu His Leu Leu Thr Leu Ala Arg Thr Gln Gln Gly Ala
                660                 665                 670

Thr Ala Val Ala Gly Ala Gly Ile Thr Gln Ser Ile Cys Leu Pro Leu
            675                 680                 685

Leu Ser Val Tyr Gln Leu Ser Thr Asn Gly Thr Ala Gln Thr Pro Ser
            690                 695                 700

Ala Ser Arg Lys Ser Leu Asp Ala Pro Ser Trp Pro Gly Val Tyr Arg
705                 710                 715                 720

Leu Ser Met Ser Leu Met Glu Gln Leu Leu Lys Thr Leu Arg Tyr Asn
                725                 730                 735

Phe Leu Pro Glu Ala Leu Asp Phe Val Gly Val His Gln Glu Arg Thr
            740                 745                 750

Leu Gln Cys Leu Asn Ala Val Arg Thr Val Gln Ser Leu Ala Cys Leu
            755                 760                 765

Glu Glu Ala Asp His Thr Val Gly Phe Ile Leu Gln Leu Ser Asn Phe
            770                 775                 780

Met Lys Glu Trp His Phe His Leu Pro Gln Leu Met Arg Asp Ile Gln
785                 790                 795                 800

Val Gly Ala Gln Asp Gly Val Leu Glu Ser Gly Val Met Leu Gly Asp
                805                 810                 815
```

```
Arg Glu Ala Val Arg Ser His Trp Gly Thr Pro Ser Glu Leu Gln Asp
            820                 825                 830

Val Pro Glu Arg Gly Leu Phe Pro Trp Gly Ala Gln Gly Leu Leu Ser
            835                 840                 845

Cys Ala Tyr Ser Gly
    850

<210> SEQ ID NO 25
<211> LENGTH: 525
<212> TYPE: PRT
<213> ORGANISM: Mus musculus

<400> SEQUENCE: 25

Thr Arg Pro Leu Gln Glu Val Ile Ala Leu Phe Asp Gln Thr Arg
 1               5                  10                  15

His Ser Leu Ala Ser Asp Ser Ala Ala Glu Asp Lys Asp Ser Met Glu
                20                  25                  30

Thr Asp Asp Cys Pro Arg Pro Arg His Lys Asp Gln Arg Asp Gly Val
                35                  40                  45

Cys Val Leu Gly Leu His Leu Ala Lys Glu Leu Cys Glu Val Asp Glu
        50                  55                  60

Asp Gly Asp Ser Trp Leu Gln Val Thr Arg Arg Leu Pro Ile Leu Pro
 65                 70                  75                  80

Thr Leu Leu Thr Thr Leu Glu Val Ser Leu Arg Met Lys Gln Asn Leu
                85                  90                  95

His Phe Thr Glu Ala Ala Leu His Leu Leu Thr Leu Ala Arg Thr
                100                 105                 110

Gln Gln Gly Ala Thr Ala Val Ala Gly Ala Gly Ile Thr Gln Ser Ile
            115                 120                 125

Cys Leu Pro Leu Leu Ser Val Tyr Gln Leu Ser Ser Asn Gly Thr Gly
        130                 135                 140

Gln Thr Pro Ser Thr Ser Arg Lys Ser Leu Asp Ala Pro Ser Trp Pro
145                 150                 155                 160

Gly Val Tyr Arg Leu Ser Met Ser Leu Met Glu Arg Leu Leu Lys Thr
                165                 170                 175

Leu Arg Tyr Asn Phe Leu Thr Glu Ala Leu Asp Phe Val Gly Val His
            180                 185                 190

Gln Glu Arg Thr Leu Gln Cys Leu Asn Ala Val Lys Thr Val Gln Ser
        195                 200                 205

Leu Ala Cys Leu Glu Glu Ala Asp His Thr Val Gly Phe Ile Leu Gln
    210                 215                 220

Leu Ser His Phe Arg Lys Glu Trp His Phe His Leu Pro Gln Leu Met
225                 230                 235                 240

Arg Asp Val Gln Val Asn Leu Gly Tyr Leu Cys Gln Ala Cys Thr Ser
                245                 250                 255

Leu Leu His Ser Arg Lys Met Leu Gln His Tyr Leu Gln Asn Lys Asn
            260                 265                 270

Gly Asp Gly Leu Pro Ser Ala Val Thr Pro Arg Ala Gln Arg Pro Ser
        275                 280                 285

Thr Thr Thr Thr Thr Thr Thr Thr Thr Ala Leu Ala Thr Pro Ala
    290                 295                 300

Gly Cys Ser Ser Lys Gln Pro Thr Ala Asp Thr Glu Ala Ser Glu Gln
305                 310                 315                 320

Arg Ala Leu His Thr Val Gln Tyr Gly Leu Leu Lys Ile Leu Ser Arg
                325                 330                 335
```

-continued

```
Thr Leu Ala Ala Leu Arg His Phe Thr Pro Asp Val Cys Gln Ile Leu
            340                 345                 350

Leu Asp Gln Ser Leu Asp Leu Ala Glu Tyr Asn Phe Leu Phe Ala Leu
            355                 360                 365

Ser Phe Thr Thr Pro Thr Phe Asp Ser Glu Val Ala Pro Ser Phe Gly
    370                 375                 380

Thr Leu Leu Ala Thr Val Asn Val Ala Leu Asn Met Leu Gly Glu Leu
385                 390                 395                 400

Asp Lys Lys Glu Ser Leu Thr Gln Ala Val Gly Leu Ser Thr Gln
            405                 410                 415

Ala Glu Gly Thr Arg Thr Leu Lys Ser Leu Leu Met Phe Thr Met Glu
            420                 425                 430

Asn Cys Phe Tyr Leu Leu Ile Ser Gln Ala Val Arg Tyr Leu Arg Asp
            435                 440                 445

Pro Ala Val His Pro Arg Asp Lys Gln Arg Met Lys Gln Glu Leu Ser
    450                 455                 460

Ser Glu Leu Ser Thr Leu Leu Ser Ser Leu Ser Arg Tyr Phe Arg Arg
465                 470                 475                 480

Gly Ala Pro Ser Ser Pro Ala Ala Gly Val Leu Pro Ser Pro Gln Gly
                485                 490                 495

Lys Ala Thr Ser Leu Ser Lys Ala Ser Pro Glu Ser Gln Glu Pro Leu
            500                 505                 510

Ile Gln Leu Val Gln Ala Phe Val Arg His Val Gln Arg
            515                 520                 525

<210> SEQ ID NO 26
<211> LENGTH: 6
<212> TYPE: PRT
<213> ORGANISM: Homo sapiens

<400> SEQUENCE: 26

Ala Gly Gly Pro Cys Val
1               5
```